US012638441B1

(12) United States Patent
Balasubramanian et al.

(10) Patent No.: US 12,638,441 B1
(45) Date of Patent: May 26, 2026

(54) LINKER COMPOUNDS

(71) Applicant: CAMBRIDGE ENTERPRISE LIMITED, Cambridge (GB)

(72) Inventors: Shankar Balasubramanian, Cambridge (GB); Maximillian T. Lee, London (GB); Dario Bressan, Cambridge (GB); Gregory Hannon, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 981 days.

(21) Appl. No.: 17/779,869

(22) PCT Filed: Nov. 27, 2020

(86) PCT No.: PCT/GB2020/053065
§ 371 (c)(1),
(2) Date: May 25, 2022

(87) PCT Pub. No.: WO2021/105723
PCT Pub. Date: Jun. 3, 2021

(30) Foreign Application Priority Data

Nov. 28, 2019 (GB) ...................................... 1917388

(51) Int. Cl.
*G01N 33/543* (2006.01)
*G01N 33/533* (2006.01)

(52) U.S. Cl.
CPC ......... *G01N 33/543* (2013.01); *G01N 33/533* (2013.01); *G01N 2458/10* (2013.01)

(58) Field of Classification Search
CPC ............... G01N 33/543; G01N 33/533; G01N 2458/10
See application file for complete search history.

(56) References Cited

FOREIGN PATENT DOCUMENTS

| JP | S4714744 B1 | 5/1972 |
| JP | S62156167 A | 7/1987 |
| WO | WO-2021/105723 A1 | 6/2021 |

OTHER PUBLICATIONS

Lee, Maximillian TW, et al. "Enabling the controlled assembly of antibody conjugates with a loading of two modules without antibody engineering." Chemical science 8.3 (2017): 2056-2060. (Year: 2017).*
Abed et al., "Synthesis and Characterization of New Hexahydro-1,3,5-S-Triazines Derivatives from Benzo Caine," Australian Journal of Basic and Applied Sciences, 12(8): 30-32 (2018).
Gundermann et al., "Synthesis and chemiluminescence of copolymers of 5-amino-8-vinyl-phthalazine-1, 4(2H,3H)-dione with methyl methacrylate or styrene, and of $\alpha$, $\omega$-bis[5-amino-phthalazine-1,4 (2H,3H)-dion-]8-yl alkanes [=$\alpha$, $\omega$-bis(6-luminyl) alkanes]: Investigations on an intramolecular 'distance effect'," Journal of Bioluminescence and Chemiluminescence, 1(4): 201-213 (1987).

(Continued)

*Primary Examiner* — Bao-Thuy L Nguyen
*Assistant Examiner* — Christopher Evans
(74) *Attorney, Agent, or Firm* — Foley Hoag LLP; David P. Halstead; Alexander J. Chatterley

(57) ABSTRACT

This invention relates to a novel linker compound of formula (i) disclosed herein. The invention also relates to antibody conjugates. The invention relates to methods which utilise the compounds and conjugates disclosed herein.

20 Claims, 51 Drawing Sheets

Specification includes a Sequence Listing.

(56)                References Cited

OTHER PUBLICATIONS

International Search Report and Written Opinion for International Application No. PCT/GB2020/053065 dated Mar. 15, 2021.
Lee et al., "Enabling the controlled assembly of antibody conjugates with a loading of two modules without antibody engineering," Chemical Science, 8: 2056-2060 (2017).
Sato et al., "Tyrosine-Specific Chemical Modification with in Situ Hemin-Activated Luminol Derivatives," ACS Chemical Biology, 10(11): 2633-2640 (2015).

* cited by examiner i) Disulfide reduction
ii) Thiol-reactive DNA conjugate i) Amine-reactive DNA conjugate

Cysteine capped

Lysine modified

SPAAC-ready
handle

Polymerisable
acrylamide handle

Polymerisable
acrylamide handle

Cysteine-reactive
bridge bis-PD 1

Cysteine-reactive
bridge

M) Molecular weight marker.
1) Untreated MIgG.
2) MIgG-AF488.
3) Untreated MIgG w/ ISP.
4) MIgG-AF488 conjugate 5 w/ISP.
Left; under visible light w/ coomassie stain. Right; under UV light for AF488 visualisation.

1) Trastuzumab conjugated to 2 ONs *via* bis-PD 1; 2) Trastuzumab modified *via* lysines to have an OAR of 2.5; 3) Trastuzumab modified *via* cysteine capping to have an avaerage loading of 1.9.

Anti-α-smooth muscle actin [1A4] (SMA) with bis-PD 1 and ON sequence 1

```
                          SEQUENCE LISTING

<160> NUMBER OF SEQ ID NOS: 7

<210> SEQ ID NO 1
<211> LENGTH: 39
<212> TYPE: DNA
<213> ORGANISM: Artificial Sequence
<220> FEATURE:
<223> OTHER INFORMATION: ON sequence 1

<400> SEQUENCE: 1
tttttgatcc gattggaacc gtcccaagcg ttgcgctag                          39

<210> SEQ ID NO 2
<211> LENGTH: 39
<212> TYPE: DNA
<213> ORGANISM: Artificial Sequence
<220> FEATURE:
<223> OTHER INFORMATION: ON sequence 2

<400> SEQUENCE: 2
tttttgctat cgttcgttcg aggccagagc attcgctag                          39

<210> SEQ ID NO 3
<211> LENGTH: 60
<212> TYPE: DNA
<213> ORGANISM: Artificial Sequence
<220> FEATURE:
<223> OTHER INFORMATION: Histone H3 (D1h2) XP(R) associated ON
<220> FEATURE:
<221> NAME/KEY: misc_feature
```

-continued

```
<222> LOCATION: (1)..(1)
<223> OTHER INFORMATION: /5AzideN/

<400> SEQUENCE: 3
agaggcggcc aatacaagcc gggatgtatt gaaggaggat agaggcggcc aatacaagcc          60

<210> SEQ ID NO 4
<211> LENGTH: 60
<212> TYPE: DNA
<213> ORGANISM: Artificial Sequence
<220> FEATURE:
<223> OTHER INFORMATION: Cleaved Caspase-3 associated ON
<220> FEATURE:
<221> NAME/KEY: misc_feature
<222> LOCATION: (1)..(1)
<223> OTHER INFORMATION: /5AzideN/

<400> SEQUENCE: 4
agaggcggcc aatacaagcc agagtgagta gtagtggagt agaggcggcc aatacaagcc          60

<210> SEQ ID NO 5
<211> LENGTH: 60
<212> TYPE: DNA
<213> ORGANISM: Artificial Sequence
<220> FEATURE:
<223> OTHER INFORMATION: Anti-CD44 associated ON
<220> FEATURE:
<221> NAME/KEY: misc_feature
<222> LOCATION: (1)..(1)
<223> OTHER INFORMATION: /5AzideN/

<400> SEQUENCE: 5
agaggcggcc aatacaagcc tgtgatggaa gttagagggt agaggcggcc aatacaagcc          60

<210> SEQ ID NO 6
<211> LENGTH: 60
<212> TYPE: DNA
<213> ORGANISM: Artificial Sequence
<220> FEATURE:
<223> OTHER INFORMATION: Anti-DNA/RNA G-quadruplex (BG4) associated ON
<220> FEATURE:
<221> NAME/KEY: misc_feature
<222> LOCATION: (1)..(1)
<223> OTHER INFORMATION: /5AzideN/

<400> SEQUENCE: 6
agaggcggcc aatacaagcc aggttaggtt gagaatagga agaggcggcc aatacaagcc          60

<210> SEQ ID NO 7
<211> LENGTH: 60
<212> TYPE: DNA
<213> ORGANISM: Artificial Sequence
<220> FEATURE:
<223> OTHER INFORMATION: Anti-CD31 associated ON
<220> FEATURE:
<221> NAME/KEY: misc_feature
<222> LOCATION: (1)..(1)
<223> OTHER INFORMATION: /5AzideN/

<400> SEQUENCE: 7
agaggcggcc aatacaagcc gatgatgtag tagtaagggt agaggcggcc aatacaagcc          60
```

LINKER COMPOUNDS

GOVERNMENT SUPPORT

This invention was made with government support under 7U01MH106035-02 awarded by the National Institutes of Health. The government has certain rights in the invention.

This application is a U.S. National Stage filing under 35 U.S.C. § 371 of PCT Application No. PCT/GB20/53065, filed Nov. 27, 2020, which claims the benefit of priority to United Kingdom Patent Application No. 1917388.9, filed on Nov. 28, 2019. The contents of the International Patent Application are incorporated herein by reference in their entirety.

This invention relates to novel linker compounds. The linker compounds of the invention are capable of covalently linking a protein or peptide probe (e.g. an antibody) to a payload. The present invention also relates to conjugates formed when a protein or peptide probe is covalently linked to a payload by a linker compound of the invention and to particular applications of the linker compound and conjugates of the invention.

BACKGROUND

In recent years, the need to combine orthogonal modalities of molecular recognition has been increasing. This has been most evident in the case of protein—DNA conjugation. Specifically, antibody-oligonucleotide conjugates (AOCs) have seen a large amount of interest owing to their unique ability to combine high-precision molecular recognition with an orthogonal readout mode (e.g. hybridisation, ligation etc.). AOCs have enabled several technologies that gather proteomic data via a DNA-based readout (e.g. iPCR, DNA-PAINT, PLA, CITE-seq etc.).[1-4] The ability to amplify oligonucleotide (ON) payloads make AOC-based detection technologies extremely sensitive compared with techniques that use traditional methods of amplification i.e. with a secondary antibody (Ab). Furthermore, the degree to which multiplexing can be achieved is much higher than with conventional means; i.e. multiplexing is only limited by the length of attached ON sequences. Owing to the growing interest of ONs as therapeutic agents, they have seen combination with therapeutic Abs to improve their in vivo targeting and ability to tolerate physiological conditions.[5,6]

The chemistry used to conjugate ONs to Abs remains limited to a handful of methods. The mainstays of ON conjugation are either; through reaction of one of the ca. 50 accessible lysine residues on the surface of an Ab with either an activated ester or aldehyde-functionalised ON; or through interchain disulfide reduction followed by capping of the newly reduced cysteines with an ON functionalised with a moiety targeting a single thiol group (e.g. maleimide).[7] Due to the highly charged nature and high mass of ON payloads, and the potential for over modification to disrupt native Ab function, typically the desired ON to Ab ratio (OAR) for most applications is between 1-3. OARs within this range appear to provide an optimal trade-off between Ab binding capability and desired ON function.[8-12]

Lysine-based conjugation using activated ester linkers is an inherently non-targeted approach that results in a heterogenous mixture of products. Moreover, reaction with aldehyde-modified linkers as part of a reductive-amination strategy necessitates the use of non-selective and harsh reducing agents. The issue of non-homogenous product generation has been somewhat mitigated through the use of aptamers and other guiding moieties to control the number of conjugated ONs and limit them to reaction within a smaller region of the Ab.[13,14] However, the guiding moieties are specific to certain antibody subtypes or epitopes and, therefore, lack universal applicability.

Cysteine-conjugation of ONs via interchain disulfide reduction and capping represents an improvement in both homogeneity of products and site-selectivity, when compared to lysine modification. However, the number of accessible thiols following Ab reduction is far greater than the desired loading of ONs (8 for IgG1, 12 for IgG2 etc.). The OAR has to be controlled via either partial reduction of the accessible disulfide network or partial reaction of a completely reduced Ab; neither method results in a homogenous selection of products. Moreover, Abs that have been modified via interchain disulfide reduction and capping have been shown to have reduced stability and functionality when compared their native or re-bridged counterparts.[15]

Until now, the acquisition of spatially resolved proteomic and transcriptomic data from the same sample (i.e. a tissue section) has been extremely difficult. The state-of-the-art for the multiplexed imaging of protein species, includes cyclic staining and de-staining using regular antibodies (4i)[25], oligonucleotide conjugated antibodies (CODEX)[26] and imaging mass cytometry (IMC). CODEX relies on antibodies conjugated with ON using traditional lysine modification or cysteine capping techniques. IMC involves conjugation of metal isotopes to Abs, with which, tissues are subsequently stained. The conjugate-stained tissue then undergoes high-resolution laser ablation, allowing the isotope labels, and the antigen to which the conjugates were bound, to be detected by mass spectrometry.[16] While this technique serves well to gather high resolution proteomic data, it is inherently destructive, making downstream gathering of other data (i.e. transcript mapping) impossible.

There are now several techniques available that can achieve highly multiplexed visualisation of transcripts within tissue that enable the mapping of 1000+ genes in a single experiment. Namely, multiplexed error-robust fluorescence in situ hybridisation (MERFISH); and more recently, similar results were achieved with spatially-resolved transcript amplicon readout mapping (STARmap).[17, 18] However, both of these techniques necessitate the broad-spectrum removal of protein species from samples in order to reduce the incidence of non-specific binding of readout probes, and a resulting low signal-to-noise ratio. To anchor transcripts in place, a bridging reagent is used to attach mRNAs (i.e through their poly-adenosine 3' end) or hybridization probes to a hydrogel cast over the tissue samples, following this, treatment with proteinase K and other clearing reagents removes all proteins and lipids from the tissue section, allowing the anchored transcripts to be visualised by FISH. This process precludes downstream retrieval of protein expression data from the same sample.

However, there remains a hitherto unmet need for a chemically robust, site-selective and efficient way of installing a controlled and limited number of ONs on to Abs that does not rely on engineering or a protein-specific targeting strategy.

Expansion microscopy is a technique that can be used to provide physical magnification within a biological specimen. By covalently anchoring specific labels within the specimen directly to an expandable polymer network, labelled constituents spaced closer than optical diffraction limit can be isotropically separated and optically resolved[27]. There is a further need for new labelled probes that can be used for expansion microscopy applications.

The present invention was derived with the foregoing in mind.

SUMMARY OF INVENTION

In a first aspect, there is provided a compound of formula (I) as defined herein, or a salt thereof.

In a further aspect, there is provided a conjugate comprising a protein or peptide probe having at least one di-sulphide bond and a compound of formula I wherein the protein or peptide probe is covalently bound to the compound of formula I.

Suitably, the protein or peptide probe has two or more di-sulphide bonds. More suitably, the protein or peptide probe is selected from an antibody (including antibody fragments and single chain antibodies), a nanobody, or any other ligand-specific protein (e.g. streptavidin, SNAP, HALO) that has at least one accessible disulphide bridge linkage that can react with a pyridazinedione group of the compound of formula (I).

In a particular aspect, there is provided an antibody bound to the compound of formula (I) as defined herein, or a salt thereof.

In another aspect, there is provided a payload bound to a compound of formula (I) as defined herein, or a salt thereof.

Suitably, the payload is selected from the group consisting of an oligonucleotide, a pharmacologically active agent (e.g. a drug or biologic), a fluorophore, a bioluminescent group, a radio-isotope or radio-labelled moiety, a polymer (e.g. PEG), a dendrimer, a peptide or a lipid.

In a further aspect, there is provided a conjugate comprising a protein or peptide probe having at least one di-sulphide bond and a payload; wherein the protein or peptide probe is connected to the payload by a compound of formula (I).

In a further aspect, there is provided a conjugate obtainable by, obtained by or directly obtained by reacting a compound of formula (I) with a protein or peptide probe having at least one disulphide bond and a payload as defined herein, wherein the protein or peptide probe and the payload react with, and covalently bind to, the compound of formula I.

In a further aspect, there is provided a method of making a conjugate as defined herein, the method comprising reacting a compound for formula (I), or a salt thereof, with a protein or peptide probe having at least one disulphide bond and a payload as defined herein wherein the compound of formula (I) forms a linker binding the protein or peptide probe to the payload.

In a further aspect, there is provided a method of detecting a biological target molecule (e.g. protein molecules, including proteins bearing specific post-translational modifications, nucleic acid molecules, carbohydrate molecules, or any other biological target for which a specific protein binder could be produced) in a biological sample, the method comprising:

(i) incubating the biological sample with a conjugate of the invention and allowing the protein or peptide probe moiety of the conjugate to bind to the biological target of interest;

(ii) removing unbound conjugate; and (iii) assaying for the presence of the conjugate within the sample;

wherein the presence of the conjugate within the sample indicates that the biological target molecule is present in the sample.

Suitably, the presence of the conjugate in the sample is detected by detecting the presence of a detectable payload present in the conjugate of the invention.

In a further aspect, there is provided a method of detecting a biological target molecule (e.g. protein molecules, including proteins bearing specific post-translational modifications, nucleic acid molecules, carbohydrate molecules, or any other biological target for which a specific protein binder could be produced) in a patient, the method comprising:

(i) administering a conjugate of the invention to a patient and allowing the protein or peptide probe moiety of the conjugate to bind to the protein of interest; and (ii) assaying for the presence of the conjugate within the sample;

wherein the presence of the conjugate within the sample indicates that the biological target of interest is present in the patient.

According to a further aspect of the invention there is provided a method of detecting and locating biological target molecules and native nucleic acid molecules of interest in a biological sample, the method comprising:

incubating the biological sample with a conjugate of the invention, to allow binding of the protein or peptide probe moiety of the conjugate with the biological target molecule of interest;

removing unbound conjugate;

contacting the biological sample with a monomeric solution;

polymerising the monomeric solution to produce a polymer matrix that is bound to the biological sample and to the at least one polymerizable group ($PG_a$) present on the conjugate;

digesting proteins within the biological sample;

assaying for the presence of the payload moiety within the polymer matrix; and detecting the presence of a native nucleic acid present in the polymer matrix by a fluorescence in-situ hybridisation technique; wherein the presence of conjugate in the polymer matrix indicates that the protein of interest was present in the biological sample and the location of the conjugates in the polymer matrix indicates the location of the protein of interest within the biological sample; and wherein the location of the native nucleic acid molecules in the polymer matrix indicates the location of the native nucleic acid molecules in the biological sample.

In a further aspect of the invention there is provided a method of detecting a biological target molecule of interest in a biological sample by expansion microscopy, the method comprising:

incubating the biological sample with a conjugate of the invention, which comprises a visualisable label and at least one polymerizable group ($PG_a$), to allow binding of the conjugate with the protein of interest;

optionally removing unbound conjugate;

contacting the biological sample with a monomeric solution capable for forming an expandable hydrogel polymer matrix;

polymerising the monomeric solution to produce an expandable hydrogel polymer matrix, wherein the conjugate that is bound to the biological target in the sample is incorporated into the expandable hydrogel polymer matrix via the polymerizable group;

hydrating the polymer matrix such that it expands; and performing microscopy to detect the presence of the visualisable detection moieties within the sample.

In another aspect, there is provided a kit of parts comprising a protein or peptide probe and a compound of formula I as defined herein.

BRIEF DESCRIPTION OF THE DRAWINGS

Embodiments of the invention are further described hereinafter with reference to the accompanying drawings, in which:

FIGS. 11 to 26 show NMR spectra for synthesised compounds.

FIG. 29: A) UV-vis trace of trastuzumab modified with bis-PD 1 showing an OAR of 2.0 (inset) SDS-PAGE of M) molecular weight marker; 1) unmodified trastuzumab; 2) trastuzumab modified with bis-PD 1 OAR 2.0; shown stained with Coomassie blue (left) and GelRed (Right) B) Raw MS of unmodified trastuzumab.

FIG. 30: A) Deconvoluted MS of unmodified trastuzumab. B) Raw MS of trastuzumab modified with bis-PD 1 OAR 2.0.

Figure 31:
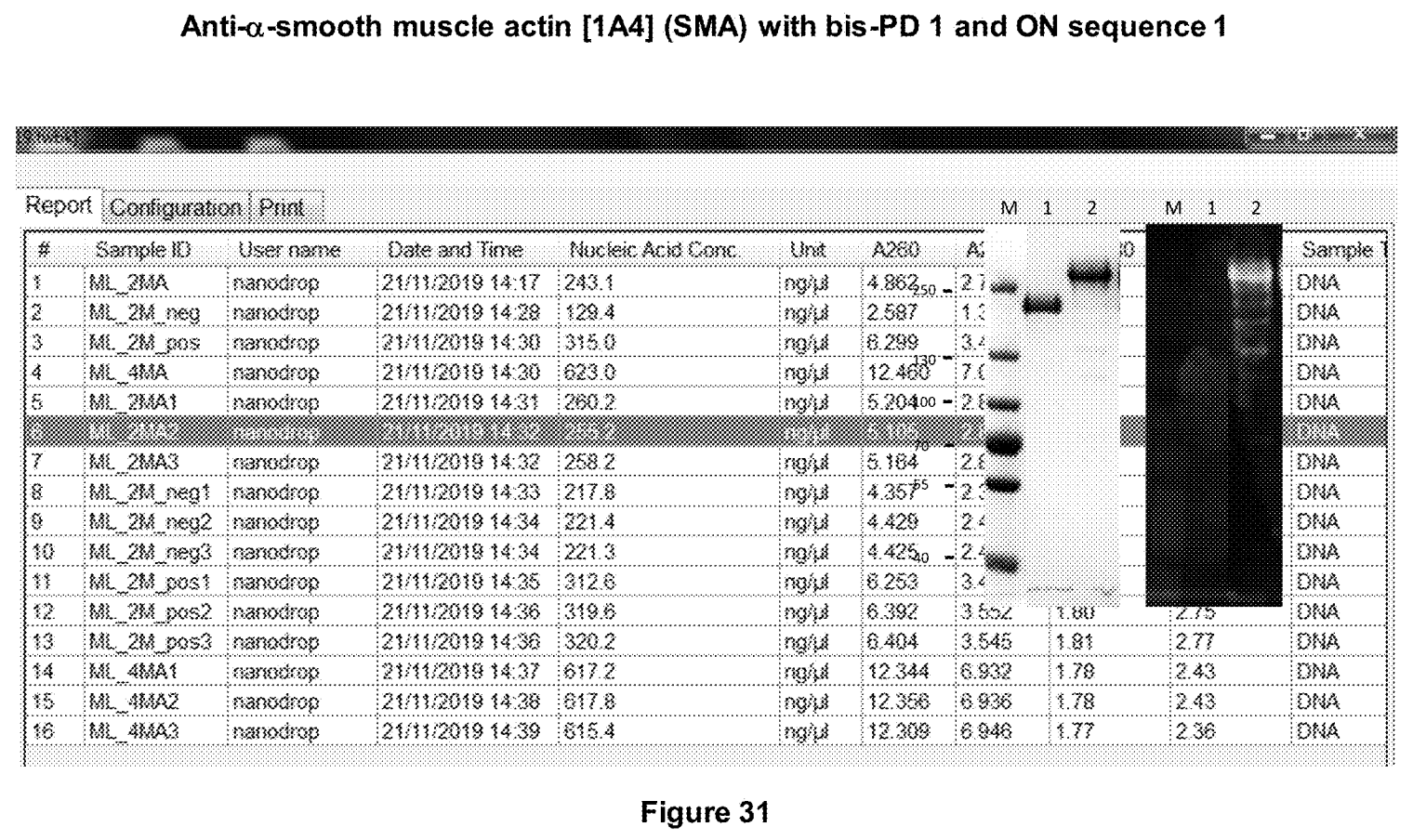

FIG. 31 shows UV-vis trace of SMA modified with bis-PD 1 showing an OAR of 2.0 (inset)) SDS-PAGE of M) molecular weight marker; 1) unmodified SMA; 2) SMA modified with bis-PD 1 OAR 2.0, shown stained with Coomassie blue (left) and GelRed (Right). (Anti-α-smooth muscle actin [1A4] (SMA) with bis-PD 1 and ON sequence 1)

7
8 against unmodified trastuzumab, an OAR 1.7 AOC of trastuzumab made via lysine modification and an OAR 1.7 AOC of trastuzumab made via cysteine capping.

Figure 35:
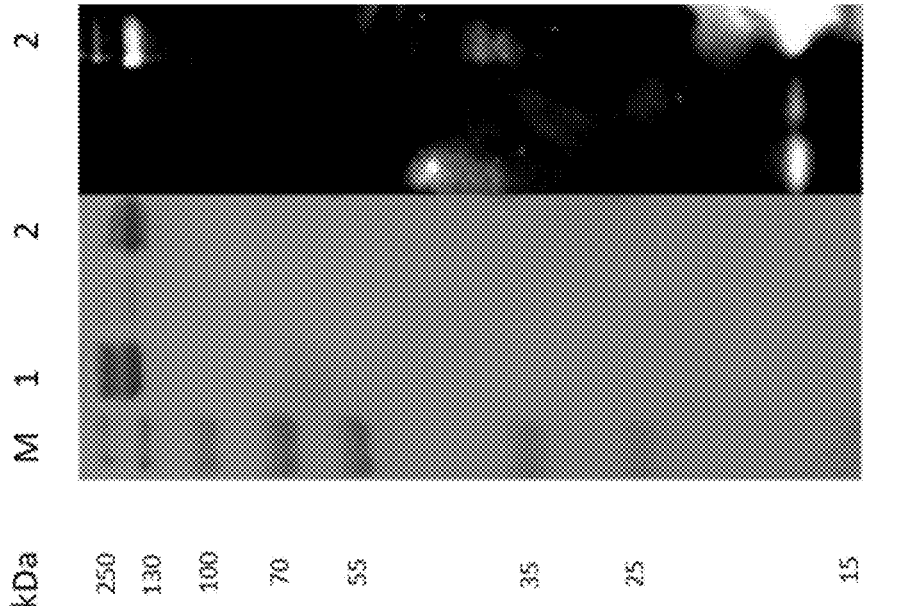

FIG. 35 shows: SDS-PAGE of Histone H3 conjugation to ON 1. M) molecular weight marker; 1) unmodified Histone H3; 2) Histone H3 modified with ON bis-PD 1 shown stained with Coomassie blue (left) and GelRed (Right). OAR≈2.3. Conditions: 2.0 μl (30 eq.) of TCEP.HCl, 16 h.

Figure 36:
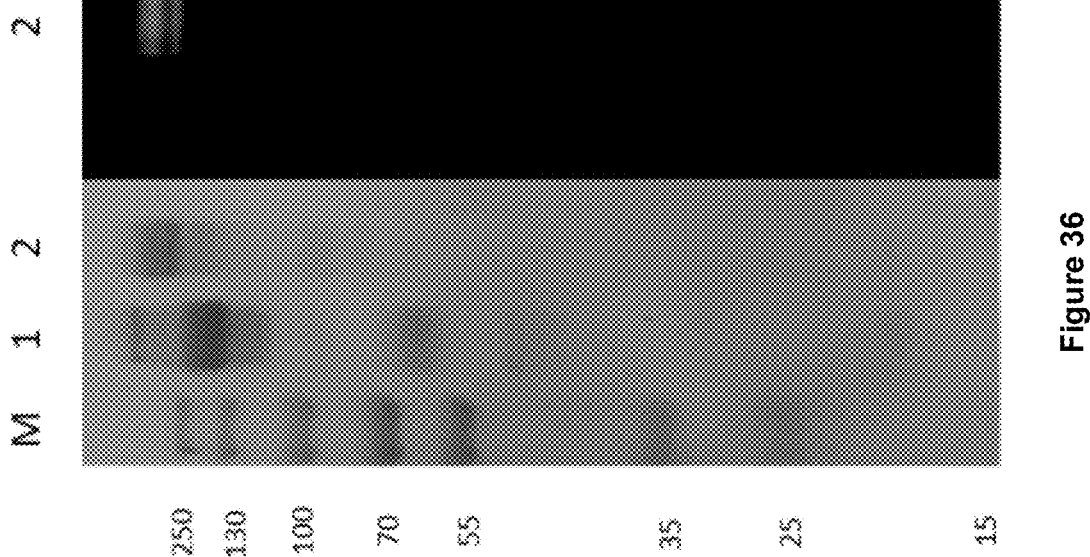

FIG. 36 shows: SDS-PAGE of Cleaved Caspase 3 conjugation to ON 3. M) molecular weight marker; 1) unmodified Cleaved Caspase 3; 2) Cleaved caspase 3 modified with ON bis-PD 3 shown stained with Coomassie blue (left) and GelRed (Right). OAR=1.9. Conditions: 2.0 μl (30 eq.) of TCEP.HCl, 16 h.

Figure 37:
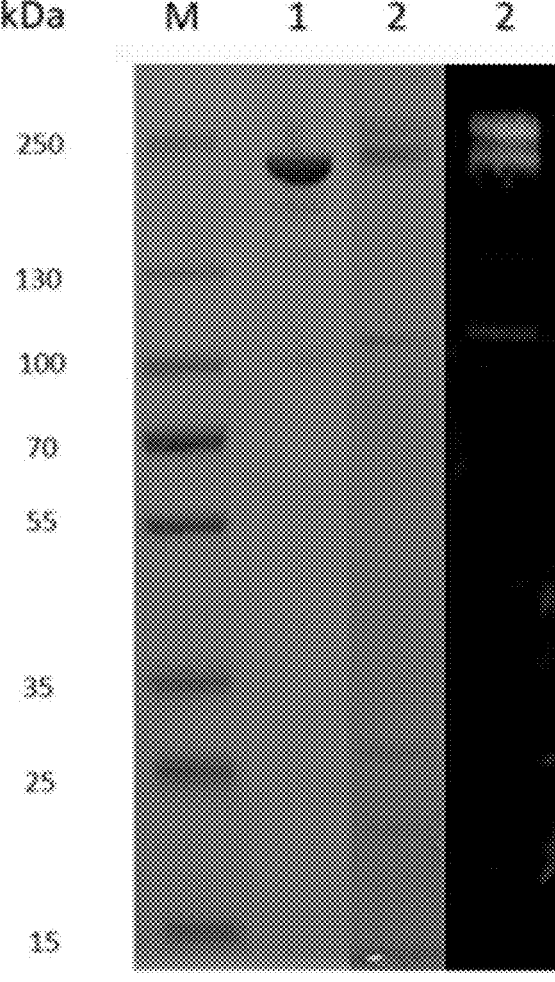

FIG. 37 shows: SDS-PAGE of Anti-CD44 conjugation to ON 4. M) molecular weight marker; 1) unmodified Anti-CD44; 2) Anti-CD44 modified with ON bis-PD 4 shown stained with Coomassie blue (left) and GelRed (Right). OAR=2.3. Conditions: 4.0 μl (60 eq.) of TCEP.HCl, 8 h.

Figure 38:
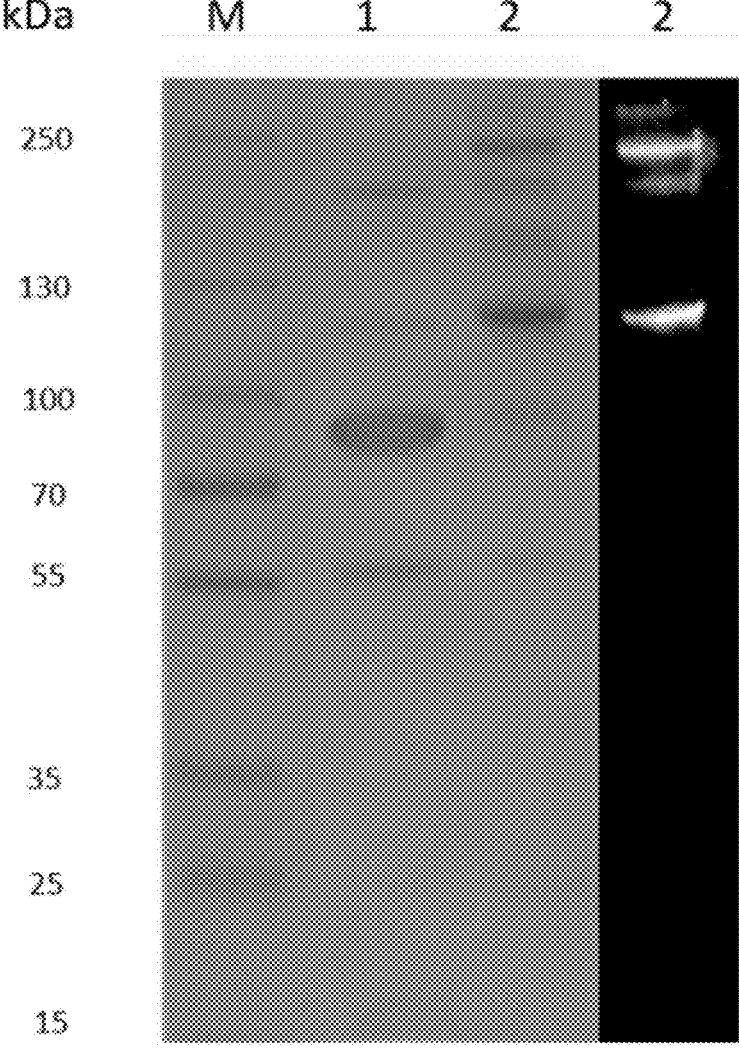

FIG. 38 shows: SDS-PAGE of BG4 conjugation to ON 8. M) molecular weight marker; 1) unmodified BG4; 2) BG4 modified with ON bis-PD 8 shown stained with Coomassie blue (left) and GelRed (Right). OAR=2 (BG4 native as received is heterogeneous, hence a resulting heterogeneous mixture of conjugate species). Conditions: 4.0 μl (60 eq.) of TCEP.HCl, 8 h.

Figure 39:
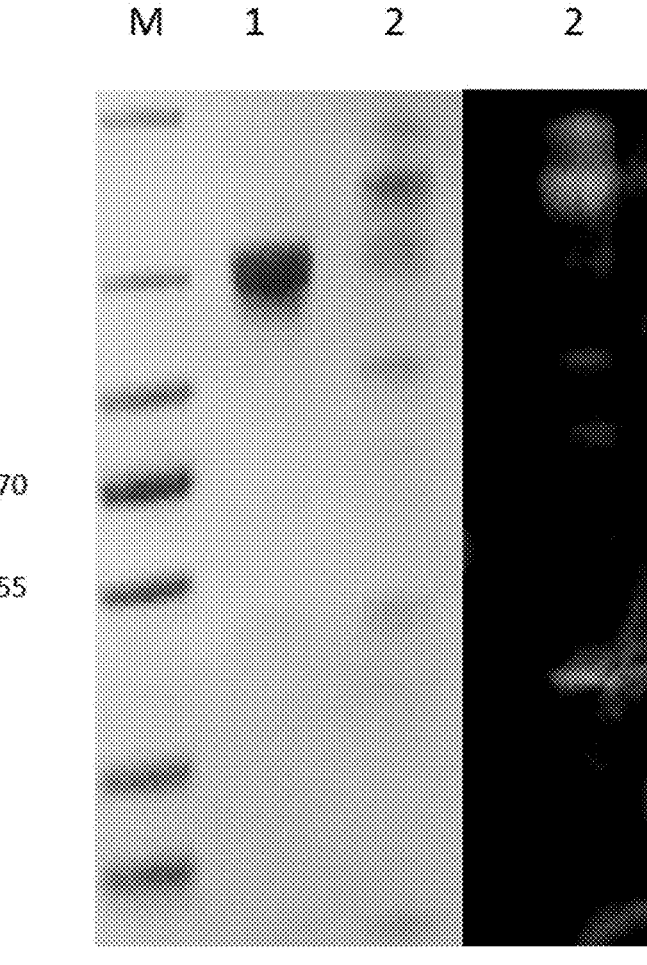

FIG. 39 shows: SDS-PAGE of Anti CD-31 conjugation to ON 14. M) molecular weight marker; 1) unmodified Anti CD-31; 2) Anti CD-31 modified with ON bis-PD 14 shown stained with Coomassie blue (left) and GelRed (Right). OAR=2.1. Conditions: 4.0 μl (60 eq.) of TCEP.HCl, 8 h.

Figure 40:
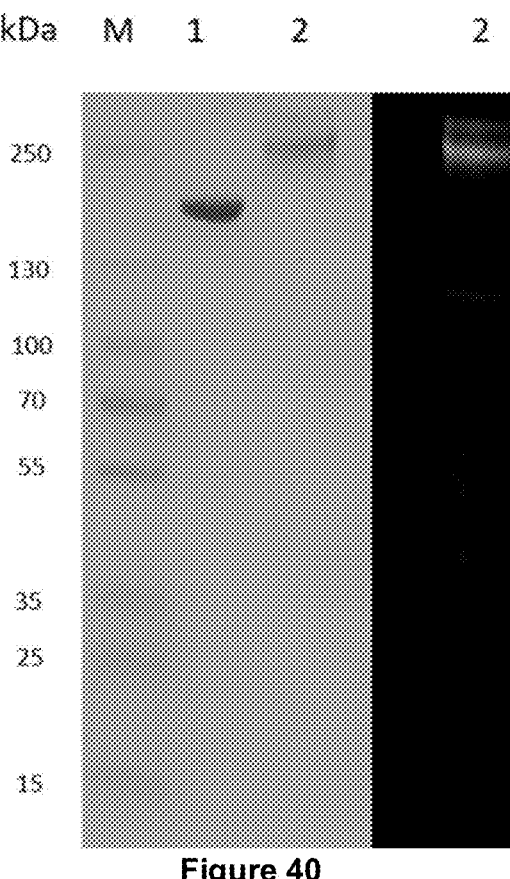

FIG. 40 shows: SDS-PAGE of Anti CD-31 conjugation to ON 14. M) molecular weight marker; 1) unmodified Anti CD-31; 2) Anti CD-31 modified with ON bis-PD 14 shown stained with Coomassie blue (left) and GelRed (Right). OAR=2.0. Conditions: 2.0 μl (30 eq.) of TCEP.HCl, 8 h.

Figure 41:
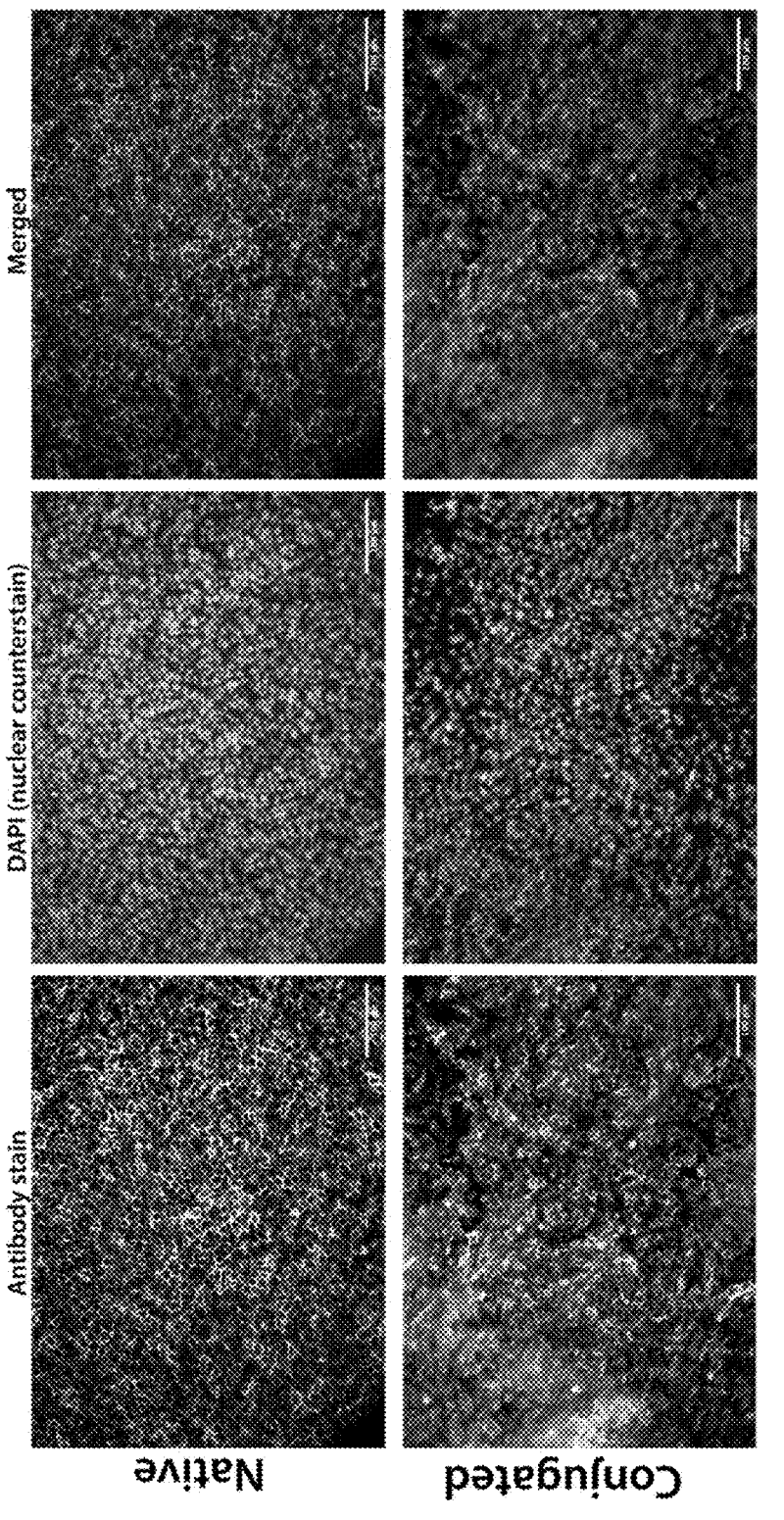

FIG. 41 shows: CD44/ON 4-immunohistochemistry staining comparing native antibodies with oligonucleotide-conjugated antibodies. Top row: immunohistochemistry staining of 4T1-derived tumour using native antibody Bottom row: same immunostaining using oligo-conjugated antibody. Staining pattern is unchanged (representative images shown).

Figure 42:
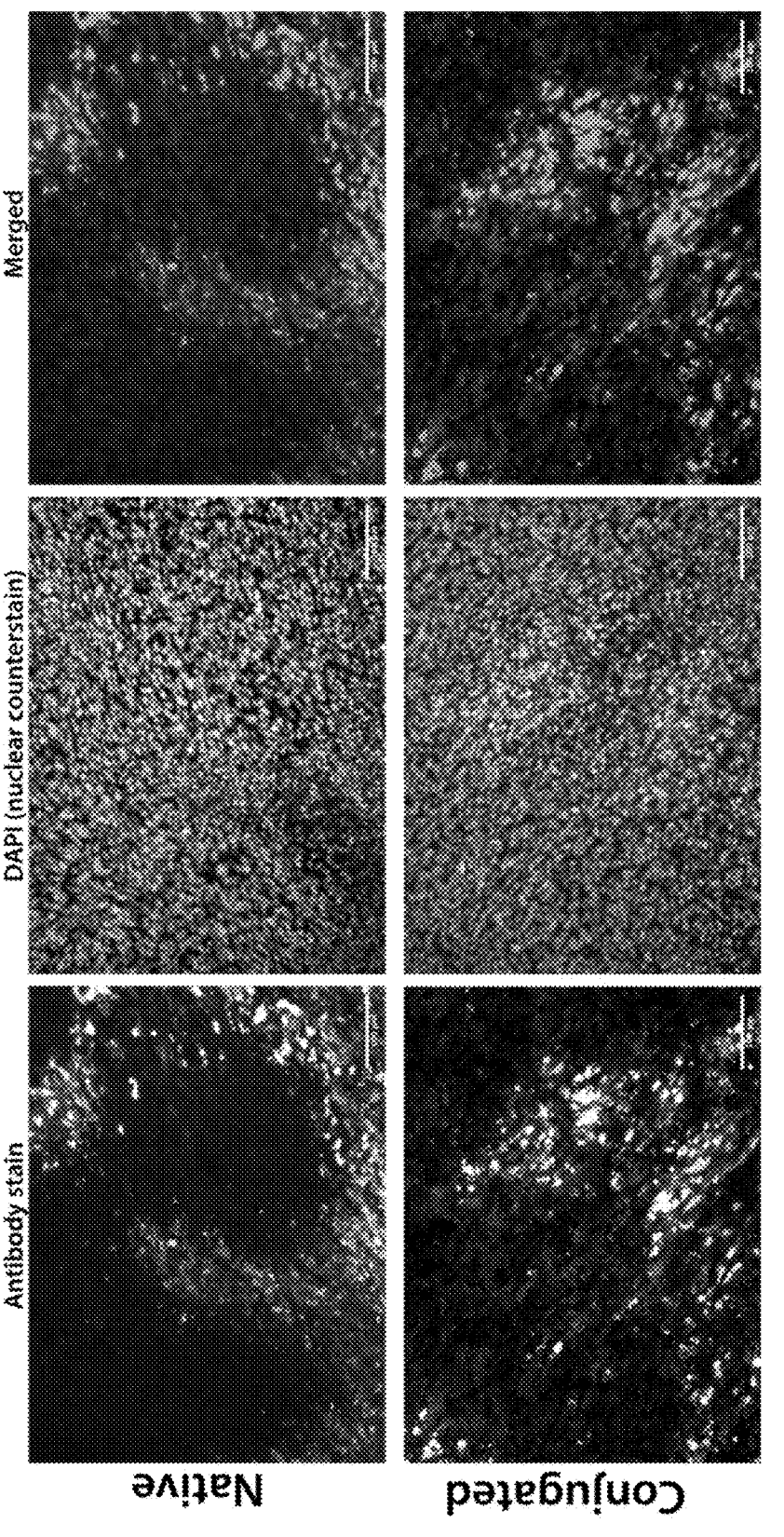

FIG. 42 shows: Cleaved Caspase 3/ON 3-immunohistochemistry staining comparing native antibodies with oligonucleotide-conjugated antibodies. Top row: immunohistochemistry staining of 4T1-derived tumour using native antibody Bottom row: same immunostaining using oligo-conjugated antibody. Staining pattern is unchanged (representative images shown).

Figure 43:
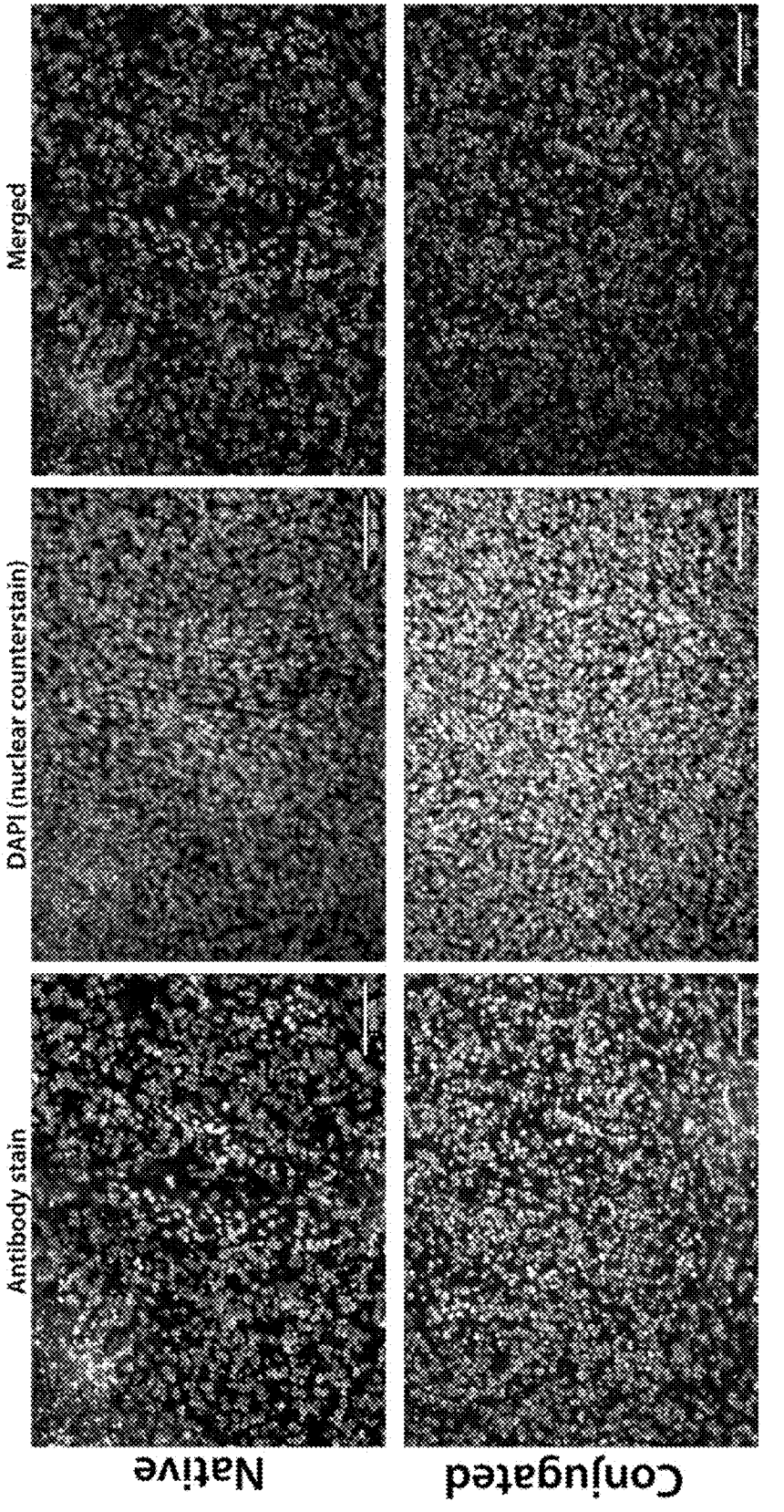

FIG. 43 shows: Histone H3/ON 1-immunohistochemistry staining comparing native antibodies with oligonucleotide-conjugated antibodies. Top row: immunohistochemistry staining of 4T1-derived tumour using native antibody Bottom row: same immunostaining using oligo-conjugated antibody. Staining pattern is unchanged (representative images shown).

Figure 44:
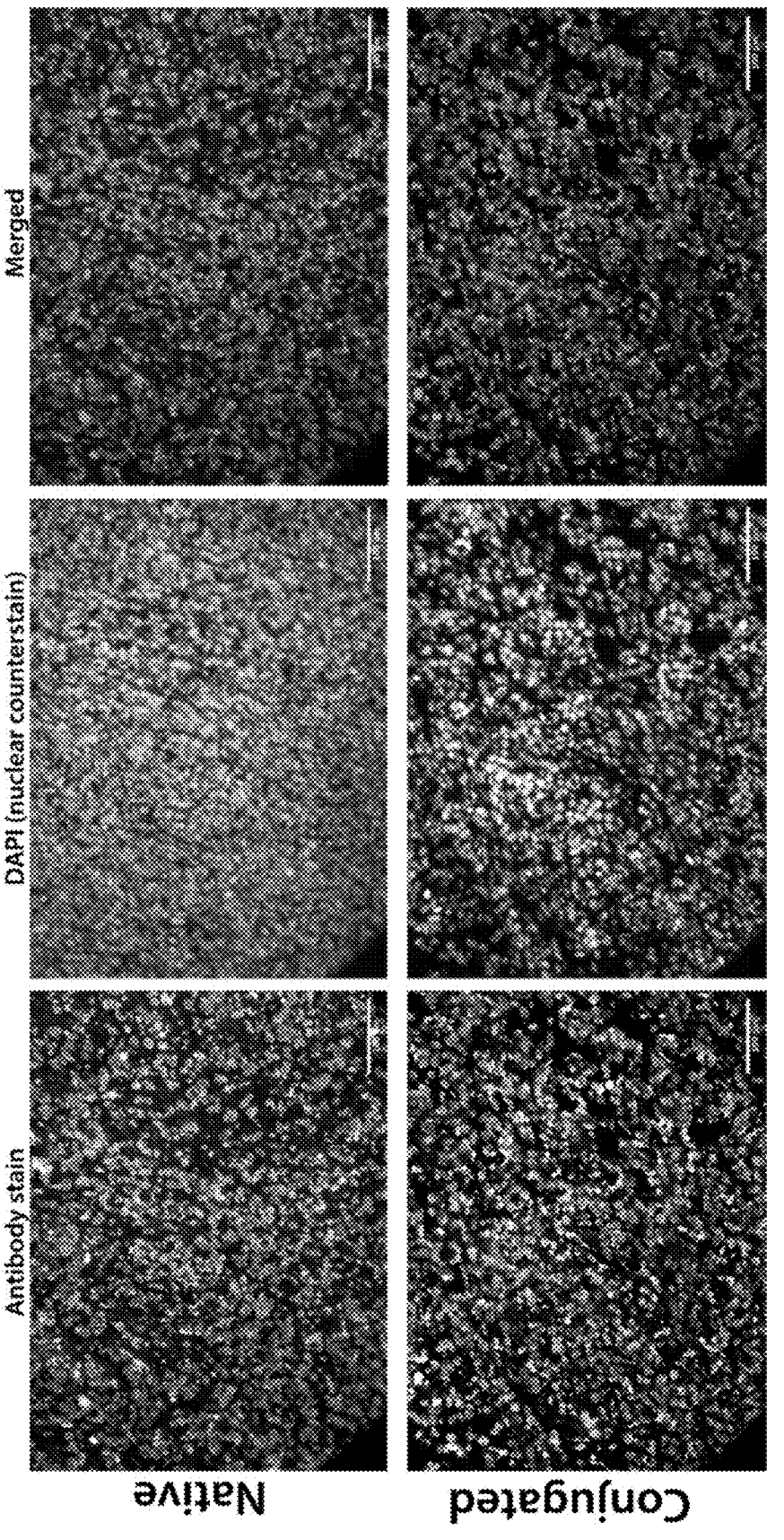

FIG. 44 shows: BG4/ON 8-immunohistochemistry staining comparing native antibodies with oligonucleotide-conjugated antibodies. Top row: immunohistochemistry staining of 4T1-derived tumour using native antibody. Bottom row: same immunostaining using oligo-conjugated antibody. Staining pattern is unchanged (representative images shown).

Figure 45:
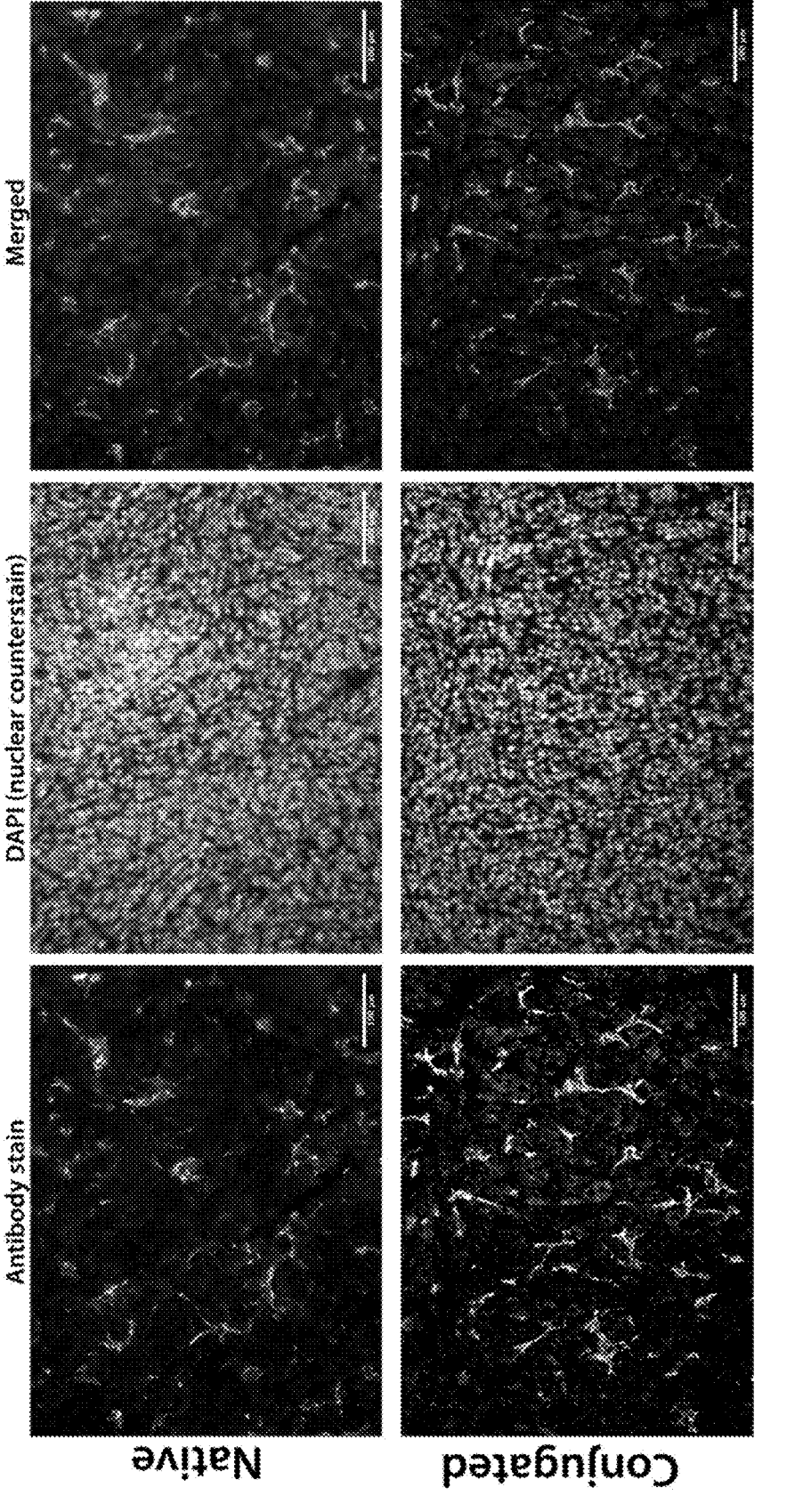

FIG. 45 shows: CD 31/ON 14-immunohistochemistry staining comparing native antibodies with oligonucleotide-conjugated antibodies. Top row: immunohistochemistry staining of 4T1-derived tumour using native antibody. Bottom row: same immunostaining using oligo-conjugated antibody. Staining pattern is unchanged (representative images shown)

Figure 46:
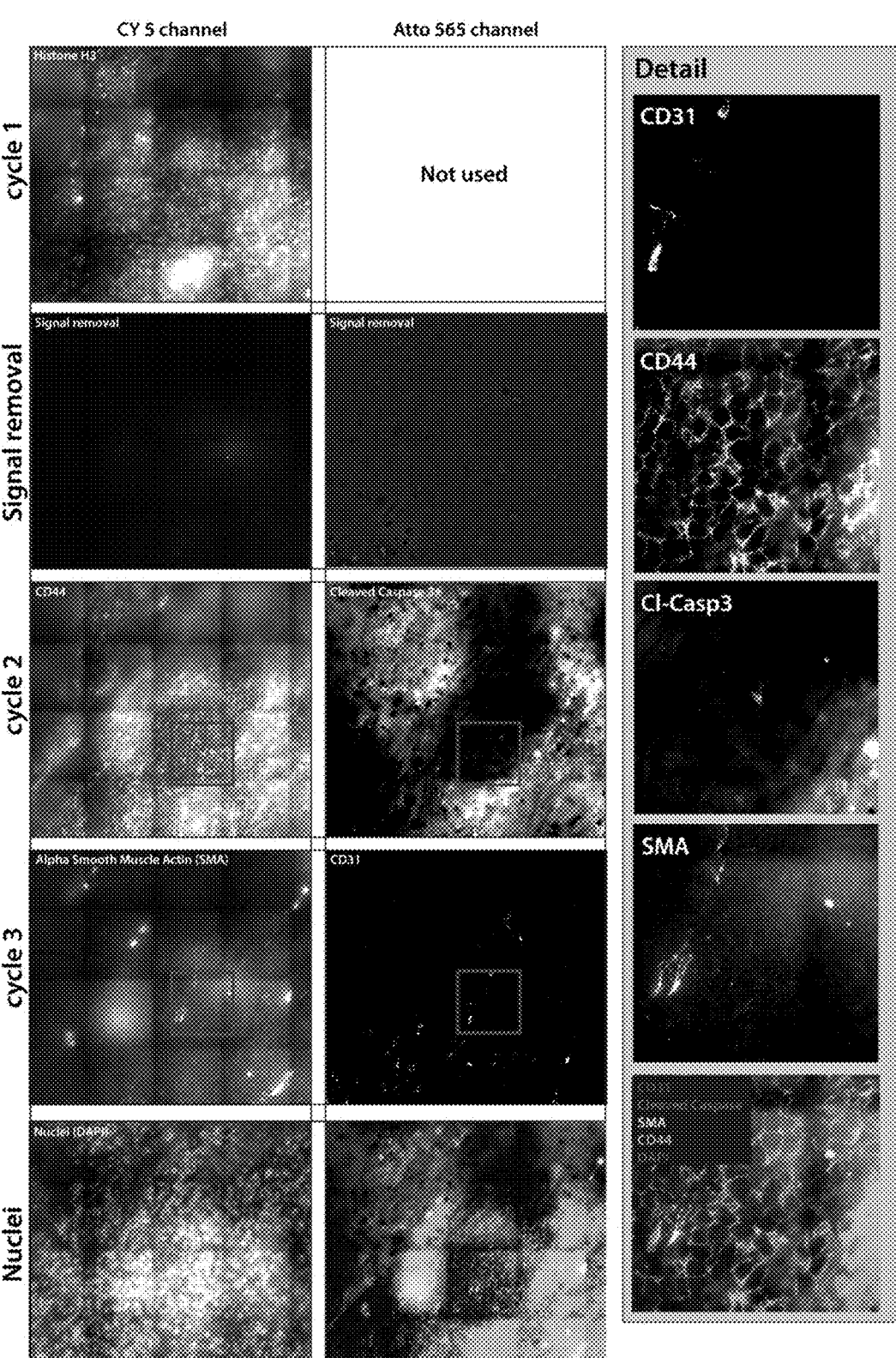

FIG. 46 shows: proFISH staining experiment including 5 antibodies over 4 imaging cycles. Each row represents one imaging cycle, with the second row corresponding to the "resetting" of the fluorescent signal produced by fluorophore cleavage. The insert in the right shows a detail of the imaged area (indicated by the highlighted square).

DETAILED DESCRIPTION

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The term "biorthogonal handle" refers to a moiety capable of reacting with, and covalently coupling to a payload as defined herein (e.g. an oligonucleotide).

The term "polymerizable group" refers to a group which is suitable for a polymerization reaction, such as, for example, free-radical or ionic chain polymerization, poly-addition or polycondensation, or for a polymer-analogous reaction, for example addition or condensation onto a main polymer chain. Particular preference is given to groups containing a C═C double bond, especially acrylamide, methacrylamide, acrylate or methacrylate groups.

The term "protein or peptide probe" refers to any protein or peptide-based probe molecule that is capable of binding to a biological target molecule. Suitably, the protein or peptide probe has at least one accessible disulphide bridge linkage which can be used to covalently link the probe to the pyridazinedione groups of the compound of formula (I) in a process known as disulphide rebridging.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Linker Compounds

In a first aspect, there is provided a compound according to formula (I), or a salt thereof:

(I)

wherein:

$Z_1$ and $Z_2$ are each independently selected from hydrogen, (1-6C)alkyl or a group:

$-L_a\text{-}PG_a$ wherein $L_a$ is (2-10C)alkylene and $PG_a$ is a polymerisable group;

with the proviso that at least one of $Z_1$ or $Z_2$ is a group $-L_a\text{-}PG_a$;

$R_1$, $R_2$, $R_3$ and $R_4$ are each independently selected from —Br, —Cl, —I, or a group of formula A:

A wherein $R_5$ is —$CO_2H$, —$CO_2Me$, —$NO_2$ or —CN, or a group of formula B:

—O—$S(O)_2$—$R_6$ wherein $R_6$ is selected from (1-6C)alkyl or phenyl optionally substituted with methyl;

$L_1$ is (1-5C)alkylene or —$[CH_2CH_2O]_{1\text{-}16}$—$[CH_2]_{2\text{-}5}$—;

$Q_1$ is absent or selected from:

(i) —$C(O)NR_a$—;

(ii) —$NR_aC(O)$—;

(iii)

(iv)

(v) —C(O)O—;

(vi) —OC(O)—;

wherein $R_a$ is selected from hydrogen or methyl;

$L_2$ is (1-5C)alkylene;

$P_1$ is a polymeric moiety having the formula:

-[Monomer A]$_a$- wherein a is 1 to 16;

Monomer A is selected from:

(i) —$OCH_2CH_2$—;

(ii)

(iii)

$P_2$ is a polymeric moiety having the formula:

-[Monomer B]$_b$— wherein b is 2 to 16;

Monomer B is selected from:

(i) —$CH_2CH_2O$—;

(ii)

(iii)

$L_3$ is absent or (1-5C)alkylene;

$Q_2$ is absent or selected from:

(i) —$C(O)NR_b$—;

(ii) —$NR_bC(O)$—;

(iii)

(iv)

(v) —OC(O)—;

(vi) —C(O)O—;

wherein $R_b$ is selected from hydrogen or methyl;

$L_a$ is (1-5C)alkylene;

$P_3$ is a polymeric moiety having the formula:

-[Monomer C]$_c$— wherein
  c is 1 to 16;
  Monomer C is selected from:
    (i) —CH$_2$CH$_2$O—;

(ii)

—CH$_2$—CH—

(iii)

C(O)CH$_3$;

—CH$_2$—CH$_2$—N—

L$_5$ is (1-5C)alkylene;
Q$_3$ is absent or selected from:
  (i) —C(O)NR$_c$—;
  (ii) —NR$_c$C(O)—;

(iii)

;

(iv)

;

(v) —C(O)—;
(vi) —C(O)O—;
(vii) —OC(O)—; or
(vii) —O—C(O)NR$_c$—;
(x) —NR$_c$C(O)—O—;
(x) —NR$_c$—;
(x) —O—;
(xii) —NR$_c$C(O)NR$_c$—;
(xiii) —S—;
(xiv) —S(O)—;
(xv) —S(O)$_2$—;
(xvi) —S(O)$_2$NR$_c$—;
(xvii) —NR$_c$S(O)$_2$—;
  wherein R$_c$ is selected from hydrogen or methyl;
P$_4$ is absent or a polymeric moiety having the formula:

-[Monomer D]$_d$- wherein
  d is 1 to 16;
  Monomer D is selected from:
    (i) —CH$_2$CH$_2$O—;

(ii)

—CH$_2$—CH—

(iii)

C(O)CH$_3$;

—CH$_2$—CH$_2$—N—

L$_5$ is (1-5C)alkylene;
Q$_4$ is a group of the formula:

-Q$_{4a}$-L$_7$-Q$_{4b}$- wherein Que is selected from:
    (i) —C(O)NR$_d$—;
    (ii) —NR$_d$C(O)—;

(iii)

;

(iv)

;

(v) —C(O)—;
(vi) —C(O)O—;
(vi) —OC(O)—; or
(vii) —O—C(O)NR$_d$—;
(viii) —NR$_d$C(O)—O—;
(x) —NR$_d$—;
(xi) —O—;
(xii) —NR$_d$C(O)NR$_d$—;
(xiii) —S—;
(xiv) —S(O)—;
(xv) —S(O)$_2$—;
(xvi) —S(O)$_2$NR$_d$—; or
(xvii) —NR$_d$S(O)$_2$—;
  wherein R$_d$ is selected from hydrogen or methyl;
L$_7$ is absent or (1-5C)alkylene;
Q$_{4b}$ is absent when L$_7$ is absent or, when L$_7$ is a
  (1-5C)alkylene, Q$_{4b}$ is absent or selected from:
    (i) —C(O)NR$_e$—;
    (ii) —NR$_e$C(O)—;

(iii)

;

(iv)

;

(v) —C(O)—;
(vi) —C(O)O—;
(vii) —OC(O)—; or
(viii) —O—C(O)NR$_e$—;
(ix) —NR$_r$C(O)—O—;
(x) —NR$_r$—;
(xi) —O—;
(xii) —NR$_e$C(O)NR$_e$—;
(xiii) —S—;
(xiv) —S(O)$_2$—;
(xv) —S(O)$_2$—;
(xvi) —S(O)$_2$NR$_e$—;
(xvii) —NR$_e$S(O)$_2$—;

wherein $R_e$ is selected from hydrogen or methyl; and R is a biorthogonal handle.

Suitably, the compound of formula I is water soluble. By water soluble, we mean that the compound will dissolve in water at room temperature and pressure.

Particular compounds of the invention include, for example, compounds of the formula (I), or pharmaceutically acceptable salts and/or solvates thereof, wherein, unless otherwise stated, each of $Z_1$, $Z_2$, $L_a$, $PG_a$, $R_1$, $R_2$, $R_3$, $R_4$, $R_5$, $R_6$, $L_1$, $Q_1$, $L_2$, $P_1$, a, Monomer A, $P_2$, b, Monomer B, $L_3$, $Q_2$, $L_4$, $P_3$, Monomer C, c, $L_5$, $Q_3$, $P_4$, d, Monomer D, $L_5$, $Q_4$, $Q_4a$, $L_6$, $Q_{4b}$, R and any associated substituent groups has any of the meanings defined hereinbefore or in any of paragraphs (1) to (70) hereinafter:—

(1) Both of $Z_1$ and $Z_2$ are a group:

-$L_a$-$PG_a$ wherein $L_a$ is (2-10C)alkylene and $PG_a$ is a polymerisable group;

(2) One of $Z_1$ and $Z_2$ is hydrogen or (1-6C)alkyl and the other is a group:

-$L_a$-$PG_a$ wherein $L_a$ is (2-10C)alkylene and $PG_a$ is a polymerisable group;

(3) Each $L_a$ group present is independently (3-10C)alkylene;

(4) Each $L_a$ group present is independently (3-6C)alkylene;

(5) Each $L_a$ group present is independently (3-4C)alkylene, e.g. propylene;

(6) Each $PG_a$ group present is independently selected from:
    (i) —$(CH_2)_{0-4}$—$NR_{PG1}$—$C(O)$—$(CH_2)_{0-4}$—$C(R_{PG2})$=$CR_{PG3}R_{PG4}$, wherein $R_{PG1}$, $R_{PG2}$, $R_{PG3}$ and $R_{PG4}$ are H or (1-2C)alkyl; or
    (ii) —$(CH_2)_{0-4}$—O—$C(O)$—$(CH_2)_{0-4}$—$C(R_{PG5})$=$CR_{PG6}R_{PG7}$, wherein $R_{PG5}$, $R_{PG6}$ and $R_{PG7}$ are H or (1-2C)alkyl;

(7) Each $PG_a$ group present is independently selected from
    (i) —$(CH_2)_{0-4}$—$NR_{PG1}$—$C(O)$—$(CH_2)_{0-4}$—$C(R_{PG2})$=$CR_{PG3}R_{PG4}$, wherein $R_{PG1}$, $R_{PG2}$, $R_{PG3}$ and $R_{PG4}$ are H or methyl; or
    (ii) —$(CH_2)_{0-4}$—O—$C(O)$—$(CH_2)_{0-4}$—$C(R_{PG5})$=$CR_{PG6}R_{PG7}$, wherein $R_{PG5}$, $R_{PG6}$ and $R_{PG7}$ are H or methyl.

(8) Each $PG_a$ group present is independently selected from
    (i) —$NR_{PG1}$—$C(O)$—$C(R_{PG2})$=$CR_{PG3}R_{PG4}$, wherein $R_{PG1}$, $R_{PG2}$, RPGs and $R_{PG4}$ are H or methyl; or
    (ii) —O—$C(O)$—$C(R_{PG5})$=$CR_{PG6}R_{PG7}$, wherein $R_{PG5}$, $R_{PG6}$ and $R_{PG7}$ are H or methyl.

(9) Each $PG_a$ group present is independently selected from
    —$NR_{PG1}$—$C(O)$—$C(R_{PG2})$=$CR_{PG3}R_{PG4}$, wherein $R_{PG1}$, $R_{PG2}$, RPGs and $R_{PG4}$ are H; or
    —O—$C(O)$—$C(R_{PG5})$=$CR_{PG6}R_{PG7}$, wherein $R_{PG5}$, $R_{PG6}$ and $R_{PG7}$ are H.

(10) Each $PG_a$ group present is —NH—$C(O)$—CH=$CH_2$.

(11) Each $L_a$ group present is independently (2-6C)alkylene (e.g. propylene) and $PG_a$ is-NHC(O)—CH=$CH_2$.

(12) $R_1$, $R_2$, $R_3$ and $R_4$ are each independently selected from —Br, —Cl, —I, or a group of formula A:

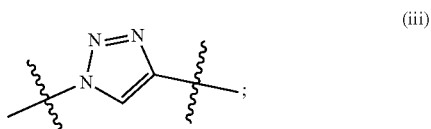

A wherein $R_5$ is —$CO_2H$, —$CO_2Me$, —$NO_2$ or —CN;
(13) $R_1$, $R_2$, $R_3$ and $R_4$ are each Br or Cl;
(14) $R_1$, $R_2$, $R_3$ and $R_4$ are each Br;
(15) $L_1$ is (2-5C)alkylene or —$[CH_2CH_2O]_{1-8}$—$[CH_2]_{2-5}$—;
(16) $L_1$ is (2-5C)alkylene or —$[CH_2CH_2O]_{1-4}$—$[CH_2]_{2-5}$—
(17) $L_1$ is (2-5C)alkylene;
(18) $L_1$ is (2-3C)alkylene;
(19) $L_1$ is (2C)alkylene;
(20) $Q_1$ is absent or selected from:
    (i) —$C(O)NR_a$—;
    (ii) —$NR_aC(O)$—;

(iii)

(iv)

(v) —$C(O)O$—;
    wherein $R_a$ is selected from hydrogen or methyl;
(21) $Q_1$ is absent or selected from:
    (i) —$C(O)NR_a$—;
    (ii) —$NR_aC(O)$—;

(iii)

(iv)

wherein $R_a$ is selected from hydrogen or methyl.
(22) $Q_1$ is selected from:
    (i) —$C(O)NR_a$—;
    (ii) —$NR_aC(O)$—;
    wherein $R_a$ is selected from hydrogen or methyl.
(23) $Q_1$ is —$C(O)NH$—.
(24) $L_2$ is (2-5C)alkylene;
(25) $L_2$ is (2-3C)alkylene;
(26) $L_2$ is (2C)alkylene;
(27) Integer a is 2 to 12;
(28) Integer a is 2 to 8, or 2 to 6, or 2 to 4, or 2 or 3;

15

(29) Integer a is 2 or 3;

(30) Monomer A is selected from:

(i) —OCH$_2$CH$_2$—; or (ii)

—CH—CH$_2$— ; (with N-substituted pyrrolidinone (=O) group)

(31) Monomer A is —OCH$_2$CH$_2$—;

(32) Integer b is 2 to 10;

(33) Integer b is 2 to 8, or 2 to 6, or 2 to 4, or 2 or 3;

(34) Integer b is 2 or 3;

(35) Monomer B is selected from:

(i) —CH$_2$CH$_2$O—; or (ii)

—CH$_2$—CH— ; (with N-substituted pyrrolidinone (=O) group)

(36) Monomer B is —CH$_2$CH$_2$O—;

(37) L$_3$ is (1-3C)alkylene (e.g. ethylene);

(38) Q$_2$ is absent or selected from:

(i) —C(O)NR$_a$—;

(ii) —NR$_a$C(O)—;

(iii) (1,2,3-triazole, N-linked at N1, linked at C4);

(iv) (1,2,3-triazole, C-linked at C4, linked at N1);

(v) —C(O)O—;

wherein R$_a$ is selected from hydrogen or methyl;

(39) Q$_2$ is absent or selected from:

(i) —C(O)NR$_a$—;

—NR$_a$C(O)—;

(iii) (1,2,3-triazole, N-linked);

(iv) (1,2,3-triazole, C-linked);

16 wherein R$_a$ is selected from hydrogen or methyl.

(40) Q$_2$ is selected from:

(i) —C(O)NR$_a$—;

(ii) —NR$_a$C(O)—;

wherein R$_a$ is selected from hydrogen or methyl.

(41) Q$_2$ is —NHC(O)—.

(42) L$_4$ is (2-5C)alkylene;

(43) L$_4$ is (2-3C)alkylene;

(44) L$_4$ is (2C)alkylene;

(45) c is 1 to 16;

(46) c is 1 to 12;

(47) c is 2 to 8;

(48) Monomer C is selected from:

(i) —CH$_2$CH$_2$O—; or (ii)

—CH$_2$—CH— ; (with N-substituted pyrrolidinone (=O) group)

(49) Monomer C is —CH$_2$CH$_2$O—;

(50) L$_5$ is (2-5C)alkylene;

(51) L$_5$ is (2-3C)alkylene;

(52) L$_5$ is (2C)alkylene;

(53) Q$_3$ is absent or selected from:

(i) —C(O)NR$_c$—;

(ii) —NR$_c$C(O)—;

(iii) (1,2,3-triazole, N-linked);

(iv) (1,2,3-triazole, C-linked);

(v) —C(O)—;

(vi) —C(O)O—.

(54) Q$_3$ is absent or —C(O)NR$_c$—;

(55) P$_4$ is absent or a polymeric moiety having the formula:

-[Monomer D]$_d$- wherein d is 1 to 12; and Monomer D is i) —CH$_2$CH$_2$O—;

ii)

—CH$_2$—CH— ; (with N-substituted pyrrolidinone (=O) group)

iii)

—CH$_2$—CH$_2$—N— (with C(O)CH$_3$ substituent on N)

(56) P$_4$ is a polymeric moiety having the formula:

-[Monomer D]$_d$- wherein d is 1 to 12; and

Monomer D is —$CH_2CH_2O$—;

(57) $P_4$ is a polymeric moiety having the formula:

-[Monomer D]$_d$- wherein d is 2 to 6; and

Monomer D is —$CH_2CH_2O$—;

(58) $L_6$ is (2-5C)alkylene;

(59) $L_6$ is (2-3C)alkylene;

(60) $L_6$ is (2C)alkylene;

(61) $Q_4$ is a group of the formula:

-$Q_{4a}$-$L_7$-$Q_{4b}$- wherein $Q_{4a}$ is selected from:

(i) —C(O)NR$_d$;

(ii) —NR$_d$C(O)—;

(iii)

(iv)

(v) —C(O)—;

(vi) —C(O)O—;

(vi) —OC(O)—; or (vii) —O—C(O)NR$_d$;

(ix) —NR$_d$C(O)—O—;

(x) —NR$_d$;

(xi) —O—;

(xii) —NR$_d$C(O)NR$_d$—;

wherein R$_d$ is selected from hydrogen or methyl;

L$_7$ is absent or (1-5C)alkylene;

$Q_{4b}$ is absent when L$_7$ is absent or, when L, is a (1-5C) alkylene, $Q_{4b}$ is absent or selected from:

(i) —C(O)NR$_e$—;

(ii) —NR$_e$C(O)—;

(iii)

(iv)

(v) —C(O)—;

(vi) —C(O)O—;

(vii) —OC(O); or (viii) —O—C(O)NR$_e$—;

(ix) —NR$_e$C(O)—O—;

(x) —NR$_e$—;

(xi) —O—;

(xii) —NR$_e$C(O)NR$_e$—;

wherein R$_e$ is selected from hydrogen or methyl; and

(62) $Q_4$ is a group of the formula:

-$Q_{4a}$-$L_7$-$Q_{4b}$- wherein $Q_{4a}$ is selected from:

(i) —C(O)NR$_d$—;

(ii) —NR$_d$C(O)—;

(iii)

(iv)

(v) —C(O)—;

(vi) —C(O)O—;

(vii) —OC(O)—; or (viii) —NR$_d$C(O)—O—;

(ix) —NR$_d$—;

(x) —O—;

wherein R$_a$ is selected from hydrogen or methyl;

L$_7$ is absent or (1-5C)alkylene;

$Q_{4b}$ is absent when L$_7$ is absent or, when L$_7$ is a (1-5C)alkylene, $Q_{4b}$ is absent or selected from:

(i) —C(O)NR$_e$—;

(ii) —NR$_e$C(O)—;

(iii)

(iv)

(v) —C(O)—;

(vi) —C(O)O—;

(vii) —OC(O); or (vi) —O—C(O)NR$_e$—;

(ix) —NR$_e$C(O)—O—;

(x) —NR$_e$—;

(xi) —O—;

(xii) —NR$_e$C(O)NR$_e$—;

wherein R$_e$ is selected from hydrogen or methyl;

(63) $Q_4$ is a group of the formula:

-$Q_{4a}$-$L_7$-$Q_{4b}$- wherein Qua is selected from:

(i) —C(O)NR$_d$—;

(ii) —NR$_d$C(O)—;

(iii) —C(O)—;

(v) —C(O)O—;

(vi) —OC(O)—;

(vii) —NR$_d$C(O)—O—;

(vii) —NR$_d$—;

(viii) —O—;

wherein $R_a$ is selected from hydrogen or methyl;
$L_7$ is absent or (1-5C)alkylene;
$Q_{4b}$ is absent when $L_7$ is absent or, when $L_7$ is a (1-5C)alkylene, $Q_{4b}$ is absent or selected from:
(i) —C(O)—;
(ii) —NR$_e$C(O)—O—;
wherein $R_e$ is selected from hydrogen or methyl;
(64) $Q_4$ is a group of the formula:

$$-Q_{4a}\text{-}L_7\text{-}Q_{4b}\text{-}$$

wherein Qua is selected from:
(i) —C(O)NR$_d$—;
(ii) —NR$_d$C(O)—;

(iii)

; or (iv)

;

(v) —NR$_d$C(O)—O—;
wherein R$_d$ is selected from hydrogen or methyl; and $L_7$ is absent or methylene and $Q_{4b}$ is absent.
(65) $Q_4$ is —NHC(O)—O—CH$_2$—;
(66) R is a group with the structure:

(67) R is a group with the structure:

;

(68) $Q_4$-R forms a group with the structure:

,

21

-continued

(69) $Q_4$-R forms a group with the structure:

(70) $Q_4$-R forms a group with the structure

Suitably, $Z_1$ and $Z_2$ are as defined in any one of paragraphs (1) to (2) above, and most suitably paragraph (1).

Suitably, $L_a$ is as defined in any one of paragraphs (3) to (5) above, and most suitably paragraph (5).

Suitably, $PG_a$ is as defined in any one of paragraphs (6) to (10) above, and most suitably paragraph (10).

Suitably, $R_1$, $R_2$, $R_3$ and $R_4$ are as defined in any one of paragraphs (12) to (14) above, and most suitably paragraph (14).

Suitably, $L_1$ is as defined in any one of paragraphs (15) to (19) above, and most suitably paragraph (19).

Suitably, $Q_1$ is as defined in any one of paragraphs (20) to (23) above, and most suitably paragraph (23).

Suitably, $L_2$ is as defined in any one of paragraphs (24) to (26) above, and most suitably paragraph (26).

Suitably, a is as defined in any one of paragraphs (27) to (29) above, and most suitably paragraph (29).

Suitably, Monomer A is as defined in any one of paragraphs (30) or (31) above, and most suitably paragraph (31).

Suitably, b is as defined in any one of paragraphs (32) to (34) above, and most suitably paragraph (34).

Suitably, Monomer B is as defined in any one of paragraphs (35) or (36) above, and most suitably paragraph (36).

Suitably, $L_3$ is as defined in paragraph (37) above.

Suitably, $Q_2$ is as defined in any one of paragraphs (38) to (41) above, and most suitably paragraph (41).

Suitably, $L_4$ is as defined in any one of paragraphs (42) to (44) above, and most suitably paragraph (44).

Suitably, c is as defined in any one of paragraphs (45) to (47) above, and most suitably paragraph (47).

Suitably, Monomer C is as defined in any one of paragraphs (48) or (49) above, and most suitably paragraph (49).

Suitably, $Q_3$ is as defined in any one of paragraphs (53) or (54) above, and most suitably paragraph (54).

Suitably, $P_4$ is as defined in any one of paragraphs (55) to (57) above, and most suitably paragraph (57).

Suitably, $L_6$ is as defined in any one of paragraphs (58) to (60) above, and most suitably paragraph (60).

Suitably, $Q_4$ is as defined in any one of paragraphs (61) to (65) above, and most suitably paragraph (65).

Suitably, R is as defined in any one of paragraphs (66) or (67) above, and most suitably paragraph (67).

Suitably, $Q_4$-R is as defined in any one of paragraphs (68) to (70) above, and most suitably paragraph (70).

Particular compounds of the invention are compounds of formula I in which:

(i) $Z_1$ and $Z_2$ are as defined in paragraph (1) or (2) above;

(ii) $L_a$ is as defined in any one of paragraphs (3) to (5) above;

(iii) $PG_a$ is as defined in any one of paragraphs (6) to (10) above;

(iv) $R_1$, $R_2$, $R_3$ and $R_4$ are as defined in any one of paragraphs (12) to (14) above;

(v) $L_1$ is as defined in any one of paragraphs (15) to (19) above;

(vi) $Q_1$ is as defined in any one of paragraphs (20) to (23) above;

(vii) $L_2$ is as defined in any one of paragraphs (24) to (26) above;

(viii) a is as defined in any one of paragraphs (27) to (29) above;

(ix) Monomer A is as defined in any one of paragraphs (30) or (31) above;

(x) b is as defined in any one of paragraphs (32) to (34) above;

(xi) Monomer B is as defined in any one of paragraphs (35) or (36) above;

(xii) $L_3$ is as defined in paragraph (37) above;

(xiii) $Q_2$ is as defined in any one of paragraphs (38) to (41) above;

(xiv) $L_4$ is as defined in any one of paragraphs (42) to (44) above;

(xv) c is as defined in any one of paragraphs (45) to (47) above;

(xvi) Monomer C is as defined in any one of paragraphs (48) or (49) above;

(xvii) $Q_3$ is as defined in any one of paragraphs (53) or (54) above;

(xviii) $P_4$ is as defined in any one of paragraphs (55) to (57) above;

(xix) $L_6$ is as defined in any one of paragraphs (58) to (60) above;

(xx) $Q_4$ is as defined in any one of paragraphs (61) to (65) above and R is as defined in any one of paragraphs (66) or (67) above; or $Q_4$-R is as defined in any one of paragraphs (68) to (70) above.

Particular compounds of the invention are compounds of formula I in which:

(i) $Z_1$ and $Z_2$ are as defined in paragraph (1) above;

(ii) $L_a$ is as defined in paragraph (5) above;

(iii) $PG_a$ is as defined in paragraph (10) above;

(iv) $R_1$, $R_2$, $R_3$ and $R_4$ are as defined in paragraph (14) above;

(v) $L_1$ is as defined in paragraph (19) above;

(vi) $Q_1$ is as defined in paragraph (23) above;

(vii) $L_2$ is as defined in paragraph (26) above;

(viii) a is as defined in paragraph (29) above;

(ix) Monomer A is as defined in paragraph (31) above;

(x) b is as defined in paragraph (34) above;

(xi) Monomer B is as defined in paragraph (36) above;

(xii) $L_3$ is as defined in paragraph (37) above;

(xiii) $Q_2$ is as defined in paragraph (41);

(xiv) $L_4$ is as defined in paragraph (44);

(xv) c is as defined in paragraph (47);

(xvi) Monomer C is as defined in paragraph (49);

(xvii) Suitably, $Q_3$ is as defined in paragraph (54);

(xviii) $P_4$ is as defined in paragraph (57);

(xix) $L_6$ is as defined in paragraph (60);

(xx) $Q_4$ is as defined in paragraph (65), R is as defined in paragraph (67) or $Q_4$-R is as defined in paragraph (70).

A particular compound of the invention is:

(referred to herein as bis-PD1 or compound 1) or a salt thereof.

Conjugates

In the conjugates of the invention, the compound of formula I suitably has one of the structures shown below:

In a further aspect, there is provided a conjugate formed by reacting a protein or peptide probe having at least one di-sulphide bond with a compound of formula I, wherein the or wherein $Z_1$, $Z_2$, $R_3$, $R_4$, $L_1$, $Q_1$, $L_2$, $P_1$, $P_2$, $L_3$, $Q_2$, $L_4$, $P_3$, $L_5$, $Q_3$, $P_4$, $L_6$, $Q_4$, and R and any associated substituent groups have any of the meanings defined hereinbefore, and wherein bonds 1, 2, 3 and 4 show the points of attachment to the disulphide bonds of the protein or peptide probe and bond 5 shows the point of attachment to the payload of the conjugate.

In one aspect, the present invention provides a conjugate comprising a protein or peptide probe having at least one di-sulphide bond that is covalently bound to a compound of formula I.

In a further aspect, there is provided a conjugate comprising a protein or peptide probe having at least one di-sulphide bond and a compound of formula I wherein the protein or peptide probe is covalently bound to the compound of formula I.

compound of formula I is covalently bound to the protein or peptide probe by the reaction of the at least one disulphide bond with a pyridazinedione group of the compound of formula (I).

The protein or peptide probe will suitably be connected to the pyridazinedione groups of the compound of formula (I). The reaction of the pyridazinedione groups of the compound of formula (I) with the disulphide bonds of the protein or peptide probe is known in the art as disulphide re-bridging.

Suitably, the protein or peptide probe has two or more (e.g. 4, 6 or 8) di-sulphide bonds capable of reacting with the two pyridazinedione groups of the compound of formula (I), thereby providing two points of attachment between the protein or peptide probe and the compound of formula I.

Suitably, the distance between the two pyridazinedione groups present in the compound of formula (I) is selected so as to enable the compound of formula I to react with, and bind to, two disulphide linkages present within the protein or peptide probe.

In an embodiment, the protein or peptide probe is selected from an antibody (including a monoclonal antibody, a poly-clonal antibody, or an antigen-binding fragment of a mono-clonal or polyclonal antibody (e.g. a nanobody or a single-chain antibody)), or any other ligand-specific protein (e.g. streptavidin, SNAP-tag, HALO-tag) that has at least one accessible disulphide bridge linkage that can react with a pyridazinedione group of the compound of formula (I).

In an embodiment, the protein or peptide probe is an antibody or nanobody.

In a particular embodiment, the protein or peptide probe is an antibody.

In a particular aspect, there is provided an antibody bound to the compound of formula (I) as defined herein, or a salt thereof. As indicated above, the antibody will suitably be connected to the pyridazinedione groups of the compound of formula (I) by disulfide re-bridging.

In another aspect, there is provided a payload bound to a compound of formula (I) as defined herein, or a salt thereof.

In a further aspect, there is provided a conjugate com-prising a payload and a compound of formula I wherein the payload is covalently bound to the compound of formula I.

The payload is suitably bound to the biorthogonal handle (R) of the compound for formula I defined herein.

In a further aspect, there is provided a conjugate formed by reacting a payload with a compound of formula I, wherein the compound of formula I is covalently bound to the payload by the reaction of the biorthogonal handle of the compound of formula (I).

Suitably, the payload is selected from the group consisting of an oligonucleotide, a pharmacologically active agent (e.g. a drug or biologic), a fluorophore, a bioluminescent group, a radio-isotope or radio-labelled moiety, a polymer (e.g. PEG), a dendrimer, a peptide or a lipid.

In a particular embodiment, the payload is a detection moiety that enables the conjugate to be detected by any suitable technique known in the art.

The detection moiety may be a fluorophore, a chro-mophore or chomogenic moiety (for example a chromogenic enzyme such as horseradish peroxidase), a bioluminescent molecule, a radionucleotide or radio-labelled moiety, an oligonucleotide, a biomolecule, a molecular sensor, a pro-tein, a peptide, a polymer, a dendrimer, or a lipid.

A suitable detection moiety for use in a conjugate as defined herein may be selected from the group consisting of: an indirectly visualisable detection moiety; and a directly visualisable detection moiety.

A directly visualisable detection moiety is a moiety, which may be a biological molecule (such as an oligonucleotide), that is bound to a visually detectable label. The visually detectable label may be selected from the group consisting of: a fluorophore; a chromophore; and a chromogenic moi-ety (for example a chromogenic enzyme such as horseradish peroxidase).

In the case that the detection moiety is a visualisable detection moiety, assaying for the detection moieties may be performed by microscopy. For example, fluorescence microscopy may be used in the case that the detection moiety is a fluorophore. Alternatively, light microscopy may be used in the case that the detection moiety is a chro-mophore, or a chromogenic moiety (for example a chro-mogenic enzyme).

An indirectly visualisable detection moiety may be detected by means of its interaction with a secondary detection moiety. Merely by way of example, an indirectly visualisable detection moiety may comprise an oligonucle-otide. A suitable secondary detection moiety may comprise a labelled nucleic acid sequence that is able to hybridise with the oligonucleotide. The label of the secondary detection moiety may be selected from the group consisting of: a fluorophore; a chromophore; and a chromogenic moiety (for example a chromogenic enzyme).

The detection moiety may be an oligonucleotide. Thus, the conjugate may be an protein or peptide probe-oligo-nucleotide conjugate, wherein the probe is connected to at least one oligonucleotide via the compound of formula (I). The probe may be connected to one or two oligonucleotides. The probe may be connected to two of the same oligonucle-otide. The probe may be connected to two different oligo-nucleotides. In a particular embodiment, the payload is an oligonucleotide.

In a further aspect, there is provided a conjugate com-prising a protein or peptide probe having at least one di-sulphide bond and a payload; wherein the protein or peptide probe is connected to the payload by a compound of formula (I).

In a further aspect, there is provided a conjugate com-prising a protein or peptide probe having at least one di-sulphide bond linked to a payload by a compound of formula I that is covalently bound to the protein or peptide probe and the payload.

As indicated above, the protein or peptide probe will suitably be connected to the pyridazinedione groups of the compound of formula (I) by disulfide re-bridging and the payload will be linked to the biorthogonal handle (R) of the compound of formula I.

In a further aspect, there is provided a conjugate formed by reacting a protein or peptide probe having at least one di-sulphide bond and a payload with a compound of formula I, wherein the compound of formula I is covalently bound to the protein or peptide probe by the reaction of the at least one covalent disulphide bond with a pyridazinedione group of the compound of formula (I) and the payload is bound to the compound of formula I by a reaction of a functional group on the payload with the biorthogonal handle R of the compound of formula I.

The conjugates may comprise one compound of formula I and one payload connected to a single protein or peptide probe. In other cases, the conjugates may comprise two or more compounds of formula I and two or more payloads connected to a single protein or peptide probe. In such cases, the protein or peptide probe suitably comprises two or more disulphide bridges. In a particular embodiment, the conju-gates defined herein may comprise different first and second payloads, which may be the same or different, attached to a single protein or peptide probe.

In an embodiment, the payload is a pharmacologically active agent. Suitably, the pharmacologically active moiety is a drug or biologic. In an embodiment, the pharmacologi-cally-active moiety is a therapeutic oligonucleotide. In an aspect, the present invention provides a conjugate as defined herein, or a salt thereof, wherein the payload is a pharma-cologically active agent, for use in therapy.

In an embodiment, the protein or peptide probe is an antibody and the payload a detection moiety as defined herein. The antibody-detection moiety conjugate may com-prise different first and second detection moieties attached to a single probe.

The detection moiety will be bound to the antibody via the compound of formula (I). The antibody will be connected to the pyridazinedione groups of the compound of formula (I)

by disulfide re-bridging. The detection moiety will be connected to the biorthogonal handle group R, of the compound of formula (I).

Depending on the type of antibody, the number of detection moieties bound to the antibody will be fixed. Typically, the antibody will be able to bind to two compounds of formula (I), meaning two detection moieties can be accommodated. Certain larger antibodies may be able to accommodate more than two (e.g. 3, 4 or 5) detection moieties.

In a further aspect, there is provided a conjugate obtainable by, obtained by or directly obtained by reacting a compound of formula (I) with a protein or peptide probe having at least one disulphide bond and a payload as defined herein, wherein the protein or peptide probe and the payload react with, and covalently bind to, the compound of formula I.

In a further aspect, there is provided a method of making a conjugate as defined herein, the method comprising reacting a compound for formula (I), or a salt thereof, with a protein or peptide probe having at least one disulphide bond and a payload as defined herein wherein the compound of formula (I) forms a linker binding the protein or peptide probe to the payload.

Suitably, the covalent linking of the payload (e.g. oligonucleotide) to the compound of formula (I) is facilitated by incubating the detection moiety and the compound of formula (I), or a conjugate of the compound of formula (I) and a protein or peptide probe under conditions whereby the payload is covalently bound to the compound of formula (I) by reacting with the biorthogonal handle R of the compound of formula (I).

Methods of the Invention

In a further aspect, there is provided a method of detecting a biological target molecule of interest in a biological sample, the method comprising:

incubating the biological sample with a protein or peptide probe-detection moiety conjugate of the invention, to allow binding of the protein or peptide probe with the biological target molecule of interest;

removing unbound protein or peptide probe-detection moiety conjugates; and.

assaying for the presence of the detection moieties within the sample wherein the presence of detection moieties within the sample indicates that the biological target molecule of interest is present in the sample.

Assaying for the detection moieties within the biological sample may be performed using a quantitative method, to allow quantification of the protein of interest within the sample.

The biological sample may be a tissue section.

Suitably the protein or peptide probe is selected from the group consisting of: an antibody, and a ligand-specific probe.

Suitably the protein or peptide probe is an antibody. Suitable the protein or peptide probe is an antibody specific for the biological target molecule of interest.

An antibody utilised herein may be a monoclonal antibody, a polyclonal antibody, or an antigen-binding fragment of a monoclonal or polyclonal antibody. An antigen-binding fragment of an antibody may be selected from the group consisting of: a nanobody; and a single-chain antibody.

A ligand-specific probe utilised herein may be a ligand-specific protein. A ligand-specific protein may be selected from the group consisting of: a HALO-tag protein; a SNAP-tag protein; and a streptavidin protein.

Suitably the biological target molecule of interest is selected from the group consisting of: a protein; a protein modification; and a carbohydrate. Suitably the biological target molecule of interest is a protein.

In the case that the biological target molecule of interest is a protein modification, the protein or peptide probe is suitably able to distinguish proteins comprising the protein modification from those proteins that do not comprise the protein modification.

Suitably unbound protein or peptide probe-detection moiety conjugates are removed by washing.

Since bound protein or peptide probe-detection moiety conjugates are localised to the site at which a biological target molecule of interest occurs, methods in accordance with this embodiment of the invention may be used to determine localisation of a biological target molecule of interest in a biological sample.

An protein or peptide probe-detection moiety conjugate for use in a method of the invention may comprise different first and second detection moieties. Methods in accordance with this embodiment facilitate multiplex assays for the presence of detection moieties within the sample.

Suitably a detection method in accordance with the invention may comprise incubating the biological sample with a plurality of protein or peptide probe-detection moiety conjugates specific for a plurality of different biological target molecules. Suitably the plurality of protein or peptide probe-detection moiety conjugates may comprise protein or peptide probe-detection moiety conjugates with specificity for between 30 and 100 different proteins. The plurality of protein or peptide probe-detection moiety conjugates may be provided in the form of a mixture, or by means of sequential incubation. Suitably protein or peptide probe-detection moiety conjugates with specificity for a particular biological target molecule are conjugated to a detection moiety that is distinguishable from the detection moiety conjugated with protein or peptide probe-detection moiety conjugates specific for different particular biological target molecules. Suitably the detection moiety is an oligonucleotide with a sequence that can be distinguished from the sequence of oligonucleotide detection moieties conjugated to protein or peptide probe-detection conjugates having specificity for other particular biological target molecules.

In a suitable embodiment of a method of the invention, such as a method described in the preceding paragraph, multiplexed detection may be effected by performing sequential rounds of fluorescence in-situ hybridization using secondary oligonucleotide probes conjugated with a secondary detection moiety, such as a fluorophore. Suitably the secondary oligonucleotide probes are able to specifically hybridise with the oligonucleotide detection moieties of the protein or peptide probe-detection moiety conjugates. Such secondary oligonucleotide probes may be sequentially incubated on the sample such that they are able to hybridise with the oligonucleotide detection moiety of the protein or peptide probe-detection moiety conjugates. Unbound secondary oligonucleotide probes may then be removed, and the presence of the secondary detection moieties (such as fluorophores) detected within the sample. Suitably the location of the secondary detection moieties in the sample may be recorded. Hybridised secondary oligonucleotide probes may then be removed by de-hydridisation, for instance by stripping using a formamide-containing buffer. The preceding steps may then be repeated, in order to achieve a desired series of sequential incubations.

Alternatively, or additionally, detection methods of the invention may comprise incubating the sample sequentially with a mixture comprising a plurality of protein or peptide probes that are conjugated to directly detectable detection moieties (such as fluorophores) via chemically cleavable linkers. Each mixture of conjugated probes may be selected to enable the simultaneous detection of all the probes. Suitably this may be achieved by selecting detection moieties that can be detected in a manner that allows them to be distinguished from one another (for example by selecting a plurality of fluorophores that may be detected using different fluorescence channels). A plurality of rounds of probe binding and detection of the bound detection moieties may be performed over time. Suitably each round of probe binding allows detection of a subset of the entire target panel. After each incubation and detection (such as imaging of fluorophore detection moieties), the detection moieties are removed by cleavage of the chemically cleavable linkers. This allows the signal to be re-set between rounds of incubation and binding, and thus enables detection of the following mixture of probes with which the sample is incubated.

A wide variety of detection techniques may be used to allow detection of antibody-detection moiety conjugates employing indirectly visualisable detection moieties. Merely by way of example, antibody-detection moiety complexes are suitable for detection by fluorescence in-situ hybridisation (FISH) techniques, or nucleic acid sequencing techniques (such as in-situ sequencing techniques, or by single-cell and spatial DNA or RNA sequencing techniques). The skilled person will recognise a number of different FISH and DNA or RNA sequencing techniques that may be employed in the methods of the invention. FISH and in-situ sequencing techniques include, but are not limited to, those selected from the group consisting of: multiplexed error-robust fluorescence in-situ hybridisation (merFISH); sequential FISH (seqFISH), starMAP, FISSEQ, SABER, BARISTA-Seq, in-situ sequencing (ISS) or single molecule fluorescence in-situ hybridisation (smFISH); single-cell and sequencing and detection techniques include, but are not limited to, spatial transcriptomics, CITE-seq, SlideSeq, or HDST.

The FISH, in situ sequencing and single-cell and spatial sequencing techniques described above are particularly useful technique for the investigation of nucleic acid distribution within biological samples such as cells. These procedure allows hundreds to thousands of different nucleic acid (primarily RNA) species to be identified, counted, and localised within a single sample.

However, prior to the present disclosure it has not been possible to gain the benefits of techniques such as the ones above described in a method that also allows the detection and localisation of a protein (or proteins) of interest within the same sample in which nucleic acids are being investigated.

According to a further aspect of the invention there is provided a method of detecting and locating protein molecules and native nucleic acid molecules of interest in a biological sample, the method comprising:

incubating the biological sample with a protein or peptide probe-detection moiety (e.g. oligonucleotide) conjugate of the invention comprising a polymerizable group $(PG_a)$, to allow binding of the protein or peptide probe with the protein of interest;

removing unbound protein or peptide probe-oligonucleotide conjugates;

contacting the biological sample with a monomeric solution;

polymerising the monomeric solution to produce a polymer matrix that is bound to the biological sample and to the at least polymerizable group $(PG_a)$ of the protein or peptide probe-oligonucleotide conjugate;

digesting proteins within the biological sample;

assaying for the presence of the oligonucleotide within the polymer matrix; and detecting the presence of a native nucleic acid present in the polymer matrix by a fluorescence in-situ hybridisation technique; wherein the presence of oligonucleotides in the polymer matrix indicates that the protein of interest was present in the biological sample and the location of the oligonucleotides in the polymer matrix indicates the location of the protein of interest within the biological sample; and wherein the location of the native nucleic acid molecules in the polymer matrix indicates the location of the native nucleic acid molecules in the biological sample.

The monomeric solution may be an acrylamide or acrylate solution. Thus, the polymer matrix may be polyacrylamide or polyacrylate. Suitably, the monomers are acrylamide monomers that form a polyacrylamide hydrogel incorporating at least one polymerisable group $PG_a$ present on the compound of formula (I). For the purpose of understanding this aspect of the invention, "native" nucleic acid molecules should be considered to be those nucleic acid molecules (such as mRNA transcripts) present in a biological sample of interest prior to introduction of the non-native nucleic acid molecules of the oligonucleotides.

Detection of the oligonucleotides and native nucleic acid molecules may be performed using a quantitative method, to allow quantification of the protein of interest and native nucleic acid molecules within the sample.

Both native and non-native nucleic acid molecules may be detected by a fluorescence in-situ hybridisation technique, by an in-situ sequencing technique, or by a single-cell or spatial sequencing technique. Merely by way of example, the fluorescence in-situ hybridisation technique may be selected from the group consisting of: multiplexed error-robust fluorescence in-situ hybridisation (merFISH); sequential FISH (seqFISH), starMAP, FISSEQ, SABER, BARISTA-Seq, in-situ sequencing (ISS) or single molecule fluorescence in-situ hybridisation (smFISH); the single-cell or spatial sequencing techniques can be selected from the group consisting of: spatial transcriptomics, CITE-seq, SlideSeq, or HDST Since the oligonucleotides originally incorporated in the antibody-oligonucleotide conjugates of the invention and the native nucleic acid molecules are effectively immobilised in the polymer (e.g. polyacrylamide or polyacrylate) matrix, their location in this matrix indicates the original location within the biological sample of the protein of interest and native nucleic acids. Prior to the present disclosure no methods existed that allowed both RNA-measurement and protein measurement techniques to be practiced in respect of the same biological samples using a fluorescence in situ hybridization, in-situ sequencing or single-cell/spatial sequencing readout. The methods of the present invention allow identification, localisation and quantification of both proteins of interest and native nucleic acid molecules of interest.

Proteins within the biological sample may be digested by any suitable technique known to those skilled in the art. Merely by way of example, proteins within the biological sample may be digested by treatment with broad spectrum proteinase K.

As set out above, methods in accordance with this aspect of the invention are also suitable for use in microscopy techniques. The ability to incorporate polymerizable groups in the protein or peptide probe-detection moiety conjugates of the invention makes them particularly suitable for use in techniques such as expansion microscopy.

Indeed, in a further aspect of the invention there is provided a method of detecting a protein of interest in a biological sample by expansion microscopy, the method comprising:

incubating the biological sample with an protein or peptide probe-detection moiety conjugate of the invention, which comprises a visualisable label and at least one polymerizable group ($PG_a$), to allow binding of the antibody with the protein of interest;

removing unbound protein or peptide probe-detection moiety conjugates;

contacting the biological sample with a monomeric solution capable for forming an expandable hydrogel polymer matrix;

polymerising the monomeric solution to produce an expandable hydrogel polymer matrix, wherein the protein or peptide probe-detection moiety conjugate that is bound to the biological sample is incorporated into the expandable hydrogel polymer matrix via the polymerizable group;

hydrating the polymer matrix such that it expands; and performing microscopy to detect the presence of the visualisable detection moieties within the sample.

Expansion microscopy techniques enable biological samples to be imaged at much higher resolution than can otherwise be achieved using conventional microscopy methods (as opposed to super-resolution microscopy methods). Expansion microscopy is much cheaper than techniques using super-resolution microscopes.

The compounds of Formula I make it simple to produce protein or peptide probe-detection moiety conjugates that also incorporate a polymerizable group, such as an acrylamide group. Such conjugates are particularly well suited to use in expansion microscopy techniques, since the polymerizable groups (e.g. acrylamide moieties) are able to become incorporated in an acrylate hydrogel polymer matrix that is used to expand the biological sample.

In another aspect, there is provided a kit of parts comprising a protein or peptide probe and a compound as defined herein. The kit may further comprise one or more of an oligonucleotide, a biomolecule, a fluorophore, a molecular sensor, a protein, a peptide or a drug.

EXPERIMENTAL

Example 1

Controlled Loading of Encoded Oligonucleotides onto Antibodies Enables Tandem Spatially Resolved Transcriptomic and Proteomic Visualisation A bis-pyridazinedione-based linker, bis-PD1 or compound 1, can be used to install exactly 2 ONs onto a broad range of IgG species, via a tethered functional disulfide re-bridging approach. Moreover, the utility of a compound of the invention in the context of a novel technique for the gathering of spatially-resolved proteomic and transcriptomic data is exemplified.

Figure 1:
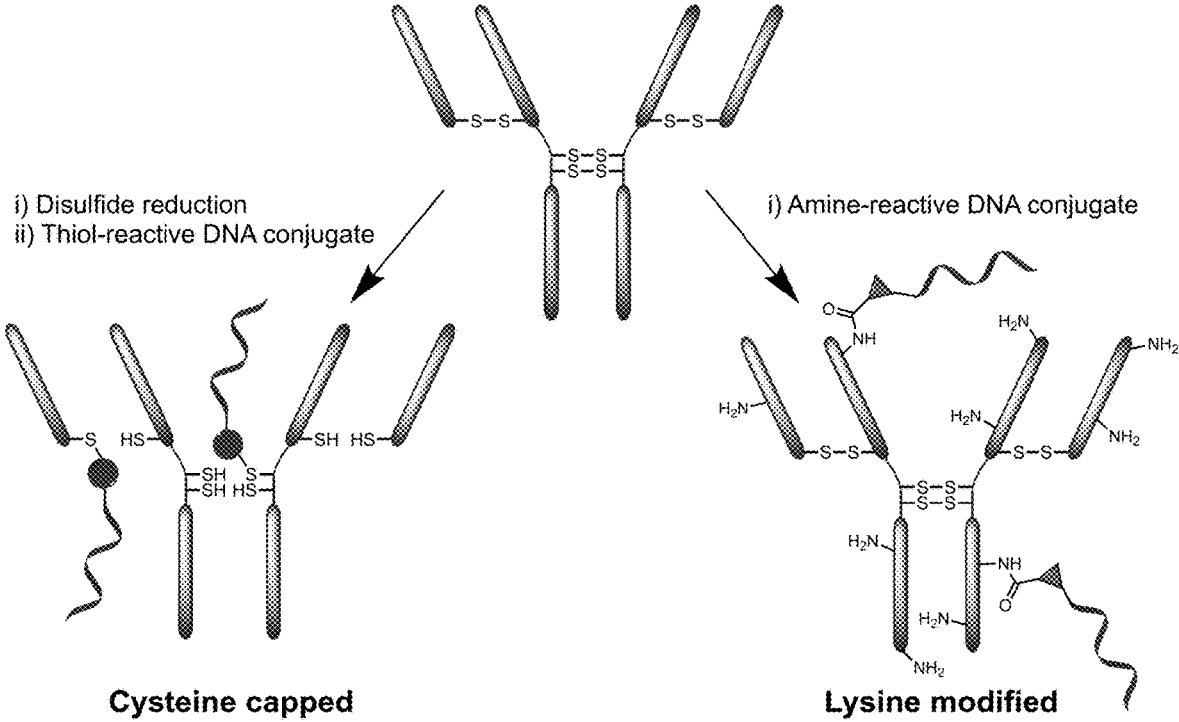
FIG. 1 shows the current field of AOC synthesis relies mainly on modification of Abs via surface lysine residues or through capping of reduced inter-chain disulfide bonds. Both methods provide little control with respect to ON loading and can have significant effects on Ab stability and activity.

Herein, there is presented a novel technique that allows multiple proteins species to be visualised via a FISH readout, which, when used in conjunction with MERFISH, develops high resolution maps of both RNA and protein species of interest. This was achieved through the site-selective dual-functionalisation of mAbs using bis-PD 1; the resulting conjugates can hold two encoded ONs, attached via the biorthogonal handle present on-PD 1, and four polymerisable acrylamide moieties each. The conjugates are then used to stain tissue sections from patient-derived xenografts (PDX) in order to localise the ON payloads around the antigen of interest. Following staining, a polyacrylamide gel is cast over the entire sample; during this process the acrylamide moieties on the conjugates become covalently attached to the newly formed hydrogel network. The samples then undergo broad spectrum proteinase-K digestion, removing all protein species from the gel matrix, and leaving behind the encoded ON bound covalently in place where the antigen was previously located. The location of the protein species in question can then be revealed via hybridisation with fluorescently-labelled probes complementary to the now immobilised oligonucleotides (FIG. 1). This technique has been named ProFISH.

Results

Functionalisation of Antibodies

Bis-PD 1 was designed with a view to being able to 'tie up' the disulfide network of any IgG in such a way that there is a theoretical upper limit to the OAR that is equal to half the number of accessible disulfide bonds; i.e. for an IgG1 with four accessible disulfide bonds, two ONs can be conjugated etc. Each molecule of bis-PD 1 featured four cysteine-reactive points located at the 4- and 5-positions on the dibromopyridazinedione (Di-Br PDs) rings, meaning each molecule can react with a 'pair' of disulfide bonds. Functional disulfide re-bridging is a technique by which the interchain disulfide bonds connecting the heavy and light chains of an Ab are first reduced and then stapled by a moiety bearing a chemical handle. This process site-selectively functionalises the Ab whilst, simultaneously, restoring the structural integrity and conformational stability offered by the original interchain bonds. Pyridazinedione-based re-bridging moieties were chosen, owing to their strong precedent of use as linkers in the construction of antibody-drug conjugates.[19-22]

The two Di-Br PDs are tethered via a flexible polyethylene glycol (PEG) linker, whose length was chosen so that the molecules could bridge the gap between any two accessible disulfide bonds (based on an intact IgG1 crystal structure PBD ref: 1IGY).[23] Precedented use of tethered linkers to create antibody-drug conjugates with large hydrophobic payloads suggested that the conjugation strategy would not restrict the conformational freedom of the Abs.[22] In the centre of the tethering linker, a tertiary amide provided a link to another PEG chain connecting a strained alkyne (bicyclo[6.1.0]nonyne, BCN) moiety to act as a biorthogonal handle, through which, an azide-functionalised ON could be attached. This second PEG chain was installed to extrude the binding point of the ON from the surface of the Ab as much as possible without compromising the conjugates' usefulness as accurate imaging tools. If the bound ON was too distal from the Ab the maximum resolution of the technique could suffer as a result, however, we had seen in previous experiments that the maximum OAR achievable is limited when chemical handles are too close to the protein's surface. This was theorised to be due to steric crowding and electrostatic repulsion between the negatively charged phosphate backbone of successive ONs.

Synthesis of Bis-PD 1

The di-Br PD disulfide-stapling moieties were synthesised according to previously reported, well optimised conditions (see synthesis section for details).[24] The acid-bearing di-Br PDs were prepared for reaction with the core PEG-based scaffold via activation to the NHS-ester-bearing analogue 2.

Reaction of bis-N-Boc PEG linker 3 with hetero-bifunctional (acid/NHS ester) PEG 4 gave the Boc-protected core scaffold 5, which underwent amine-deprotection and subsequent coupling with two molecules of NHS-ester PD 2. The resulting acid-bearing bis-PD scaffold 6 underwent conversion to an activated NHS-ester, which was immediately reacted with the commercially available BCN—NH₂, to give the final product bis-di-Br PD 1 (Scheme 1).

Conjugation to Abs

The encoded ON payloads could be conjugated to bis-PD 1 before or after installation onto the Abs. In this case it was decided to attach the ONs to bis-PD 1 prior to conjugation to the Abs, as this minimised the number of purification steps the conjugates were subjected to.

Figure 6:
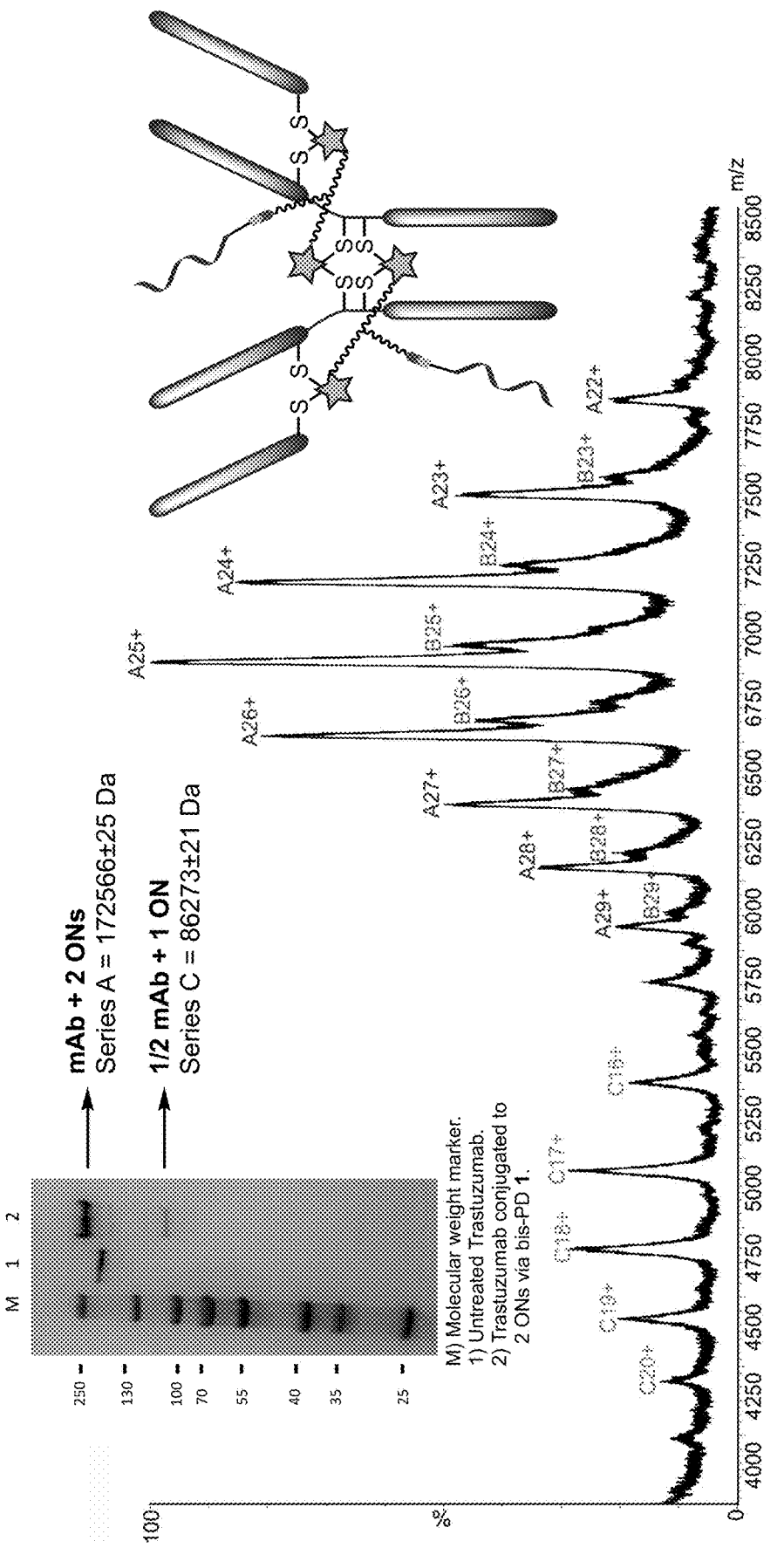
FIG. 6 shows (Main) Raw mass spectrum of clinically approved mAb Trastuzumab conjugated to exactly two ONs via bis-PD-1. Series A corresponds to the predominant desired species, mAb+2 ONs; Series B corresponds to Trastuzumab glycoform GOF/GOF resulting from incomplete PNGase F deglycosylation; Series C corresponds to the fragment, ½ mAb+1 ON. (Inset) An SDS-PAGE of the same sample; M) Molecular weight marker; 1) Unmodified Trastuzumab; 2) Trastuzumab conjugated to exactly two ONs via bis-PD 1. The ½ mAb fragment is significantly enriched by MS, owing to more facile ionisation and detection due to its smaller size; by densitometry analysis of the inset SDS-PAGE, the mAb+2 ON species accounts for >95%.

The selected ONs were 40 nt in length (ca. 12 kDa); this length ensured sufficient specificity between different Abs, as the higher the degree of multiplexing desired, the higher the number of orthogonal readout sequences required. The ON payloads contained an azide moiety at the 5' end, allowing a rapid strain-promoted azide-alkyne cycloaddition reaction with the strained alkyne BCN group on bis-PD 1 (Scheme 2). Following this, the conjugation-ready ONs were reacted with their previously assigned mAbs. Due to the compatibility of both bis-PD 1 and the attached ON with tris-(carboxyethyl)-phosphine (TCEP), the reducing agent most commonly employed to reduce interchain disulfide bonds, the final ON-Ab conjugation step proceeds as a 'one-pot' reaction requiring minimal purification. The selected mAbs were incubated with the bis-PD-bound ONs and TCEP for 8 hours at 4° C. For the well characterised mAb trastuzumab, a full suite of physical characterisation was carried out to establish an exact OAR of 2.0. Native mass spectrometry was carried out on showing a mass increase corresponding to exactly two bis-PD 1-ON conjugates (FIG. 6). To the best of our knowledge this is the first time a mass spectrum of an AOC of this size has been obtained to such a high degree of accuracy. MS of AOCs is typically non-trivial owing to the unique conditions needed to ensure ionisation of DNA and protein species; DNA is typically ionised and detected as a negative ion, whereas protein undergoes positive ionisation more readily. Moreover, the homogeneity of the sample can be independently validated via SDS-PAGE by reference against mAbs loaded on the same gel with an average loading of 2.0, as mAb species with different OARs undergo sufficiently distinct migration. The presence of DNA on a conjugate can be also be shown via a two-stage gel staining protocol; initially, gels can be stained and imaged using GelRed to indicate the presence of DNA, a follow up stain with Coomassie blue reveals the presence of protein; if the two sets of bands are congruent, the species containing both DNA and protein can be elucidated.

Figure 2:
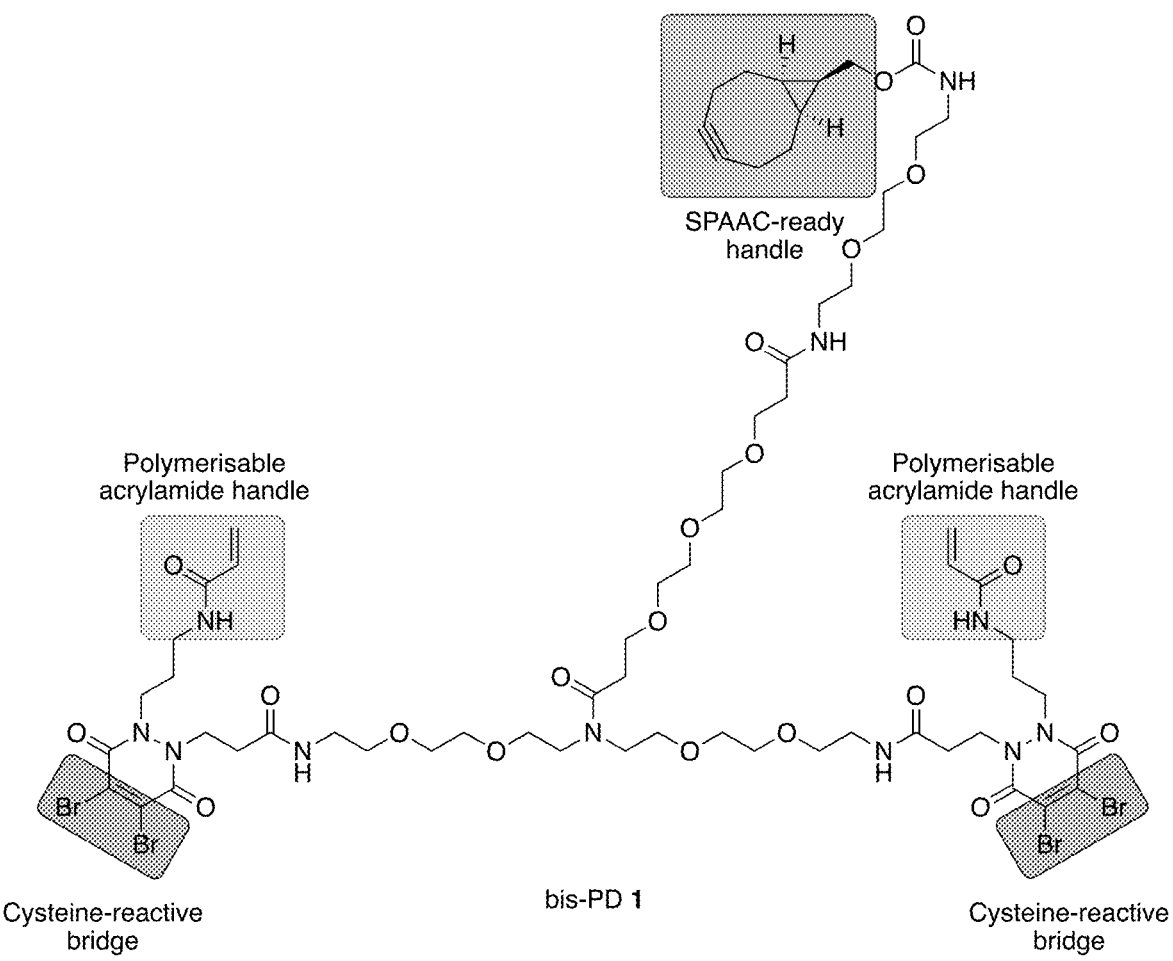
FIG. 2 shows structure of bis-pyridazinedione (PD) linker 1; containing 4 cysteine reactive centres (2 at each PD moiety), 2 polymerisable acrylamide moieties and 1 strain-promoted azide-alkyne cycloaddition-ready (SPAAC) biorthogonal handle. Each linker is capable of 'tying up' one pair of disulfide bonds, therefore, limiting the total number of chemically accessible handles to be equal to half the total number of accessible disulfide bonds.
Figure 3:
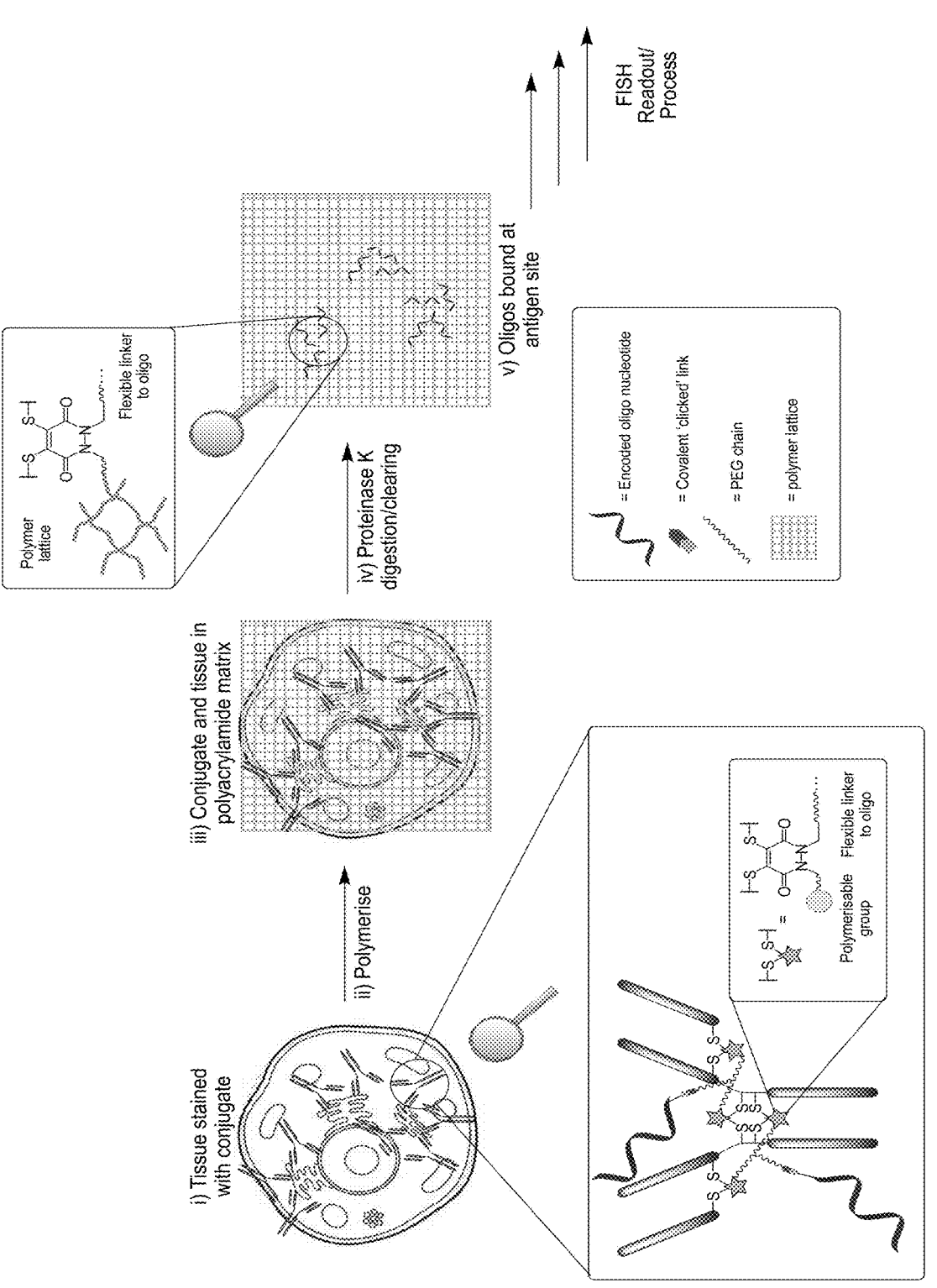
FIG. 3 shows the ProFISH workflow; samples are stained with dual functionalised Abs; carrying both an encoded oligo nucleotide and a polymerisable moiety; the entire sample undergoes radical chain reaction polymerisation reaction; the sample then undergoes broad spectrum protein digestion leaving the encoded oligonucleotides bound covalently in place at the site of the antigen, allowing its location to be elucidated via a FISH readout.
Figure 4:
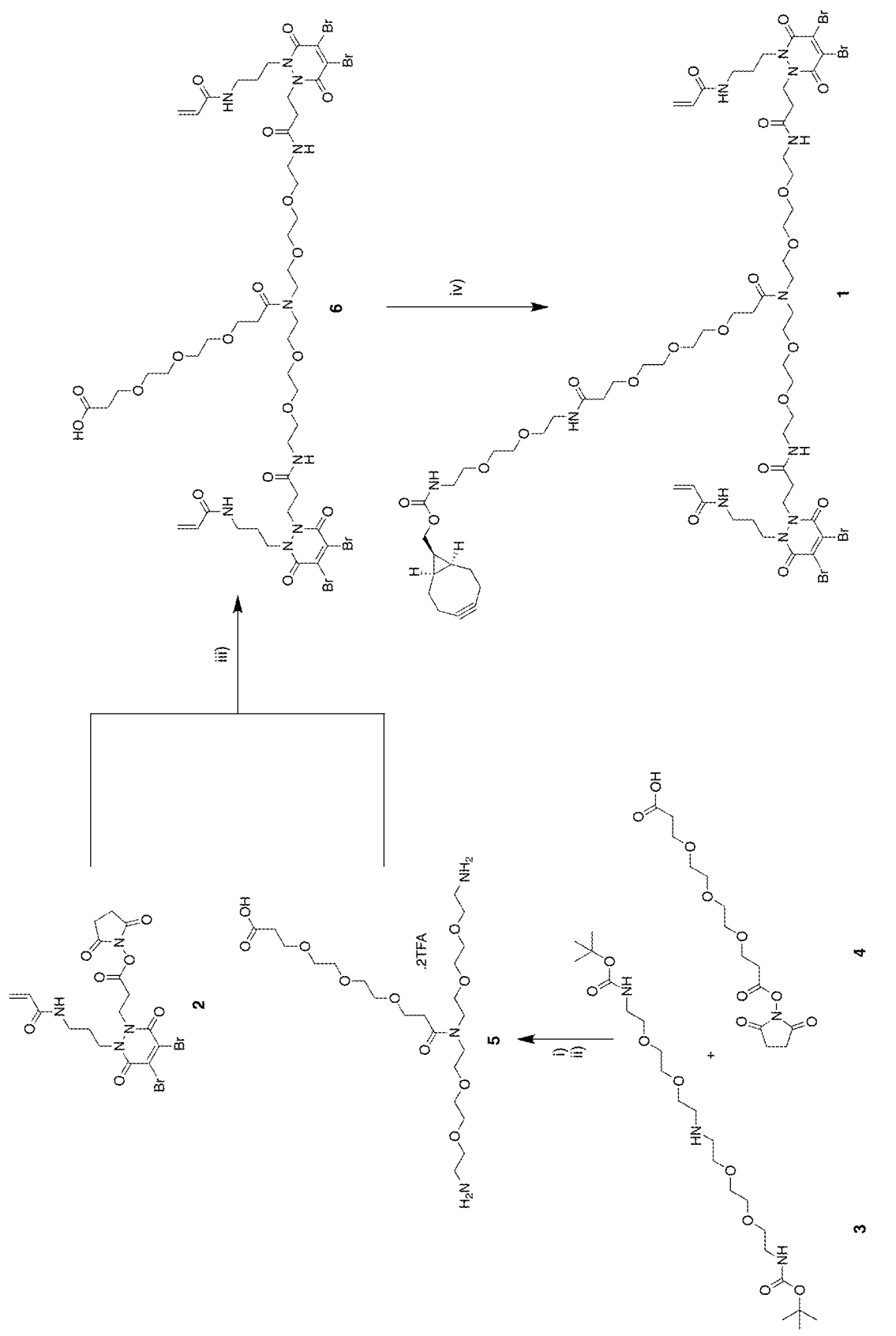
FIG. 4 shows scheme 1: i) Et₃N, DCM, 21° C.; ii) 50/50 TFA/DCM, 21° C.; iii) Et₃N, MeCN, 21° C.; iv) BCN—NH₂, DCC, NHS, 21° C.
Figure 5:
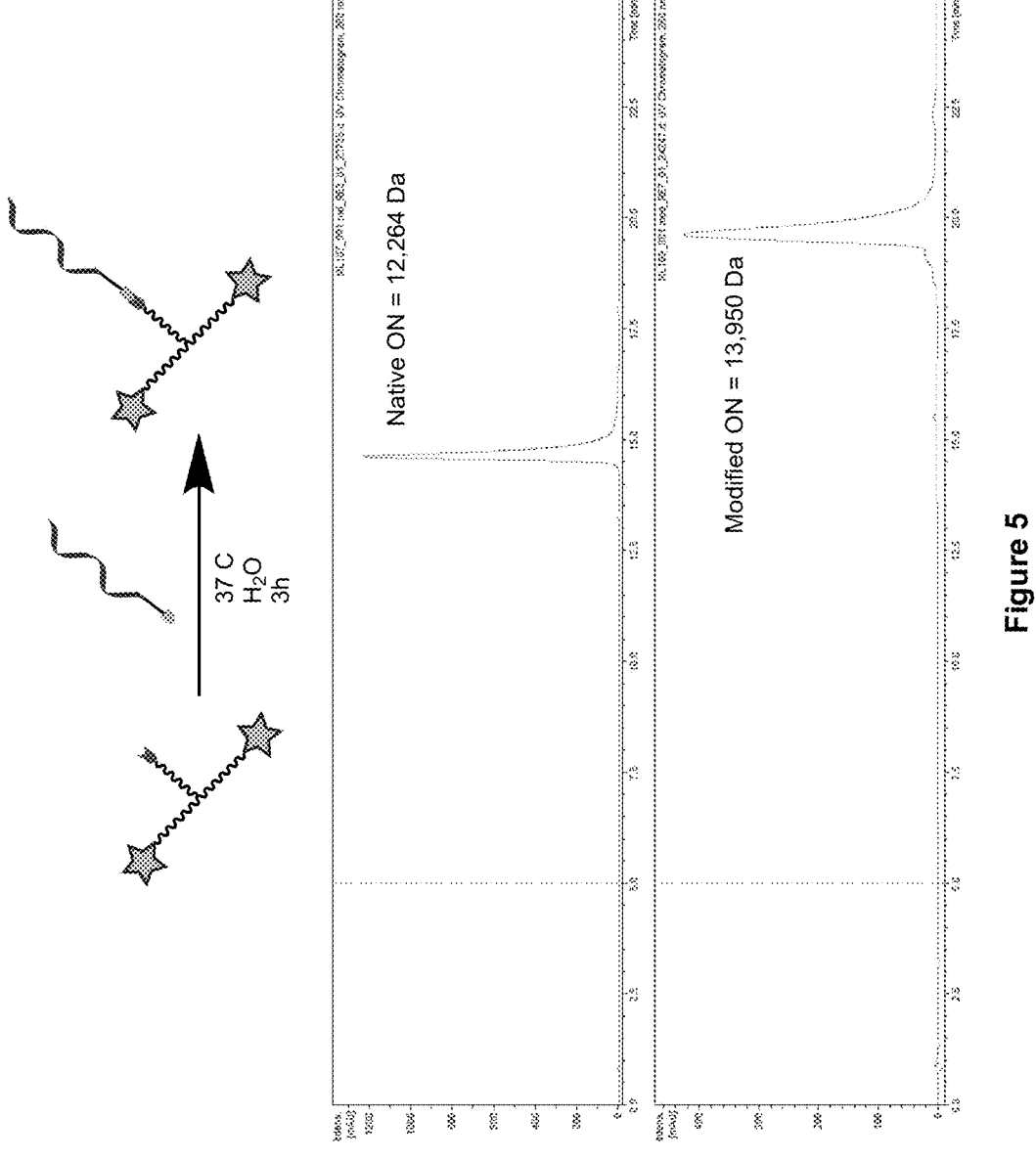
FIG. 5 (top) shows scheme 2: i) Bis-PD 1, ON-Azide, H₂O, 37° C.; (middle) LC-MS trace of unmodified ON-azide; (bottom) LC-MS trace of ON modified with bis-PD 1

Scheme 1 (FIG. 2) shows the general reaction scheme for functionalisation of mAbs with bis-PD 1-ON constructs and (lower left) characterisation by SDS-PAGE.

Testing In Situ Polymerisation

Figure 7:
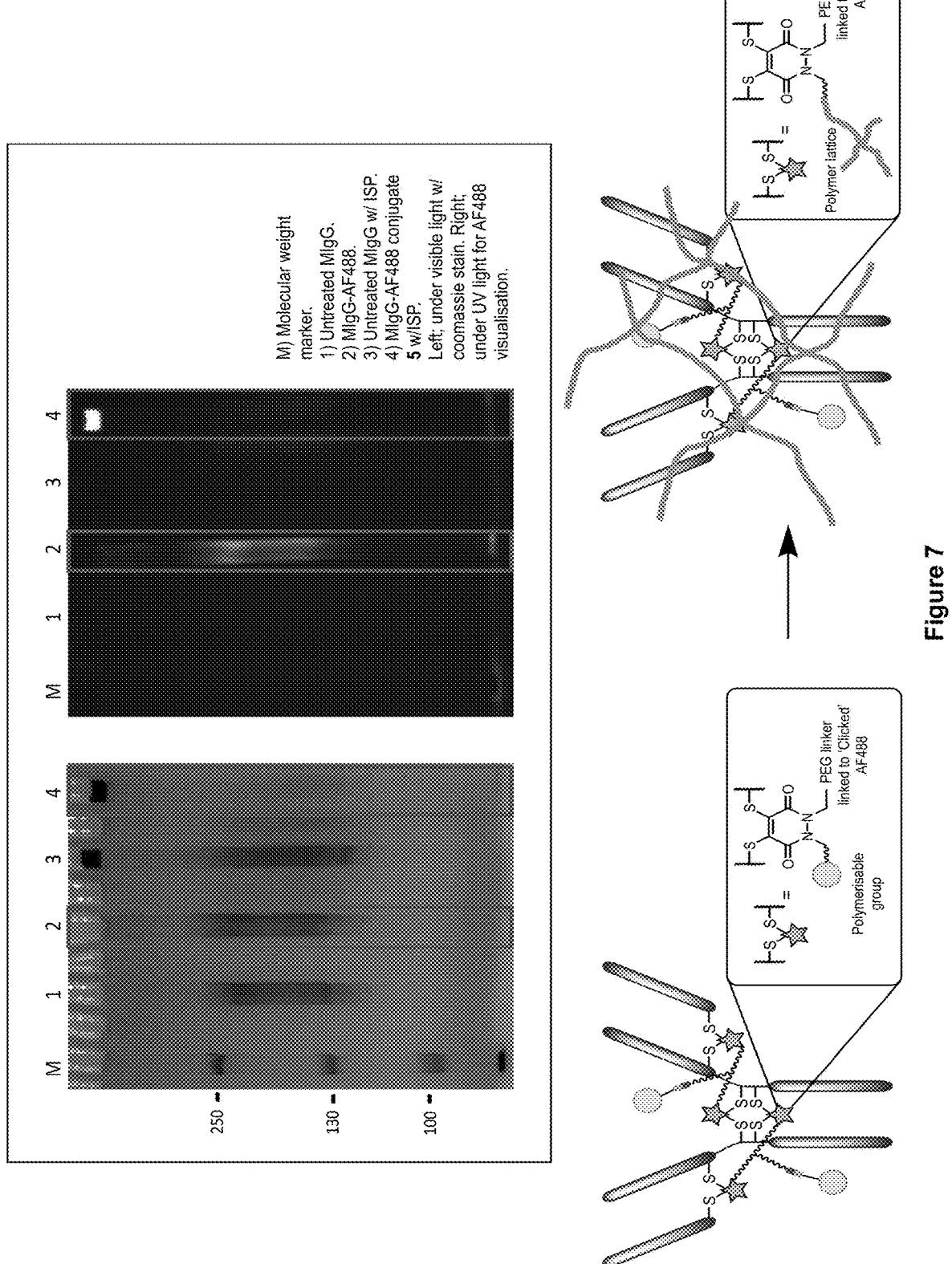
FIG. 7 shows Scheme 3: Functionalisation and polymerisation of PD 1-functionalised MIgG. Inset; SDS-PAGE showing in situ polymerisation of MIgG-AF488 conjugate; following polymerisation the conjugate is covalently bound at the top of the gel (lane 4), both the unconjugated Ab that had undergone polymerising conditions (lane 3) and non-polymerised conjugate (lane 2) moved down the gel.

Before application to tissue was attempted, it was prudent to ensure that the polymerisable functionality of bis-PD 1 had been preserved following conjugation. As the polymerisable acrylamide moieties on bis-PD 1 are also susceptible to Michael addition, it was necessary to appraise whether they had reacted with the newly liberated thiols rather than at the desired 4- and 5-positions on the di-Br PD rings. An experiment was designed in which a bis-PD 1-conjugated bulk mouse IgG (MIgG), 'clicked' to AlexaFluor 488 azide (AF488) for visualisation, was run alongside its native counterpart on an SDS-PAGE; MIgG was chosen as it contains a mixture of IgG subtypes and clones. Once loaded in the wells of a pre-cast polyacrylamide gel, the samples were subjected to polymerisation conditions and then run as per a typical SDS-PAGE. Gratifyingly, the acrylamide-bearing MIgG-AF488 conjugates became immobilised at the top of the gel and were unable to progress down the gel despite the electrical current, where as their native counterparts were seen to move down the gel as expected. This demonstrated that the acrylamide moieties had not been perturbed by the conjugation reaction and that the conjugates had successfully been covalently anchored in place (Scheme 3-FIG. 7).

Comparison of Conjugation Strategies

In order to assess the effects of different conjugation techniques on both homogeneity of products and antigen binding, both a lysine-modified and a cysteine-capped conjugate of trastuzumab were synthesised with a target OAR of 2.0 (see ESI for details).

Figure 8:
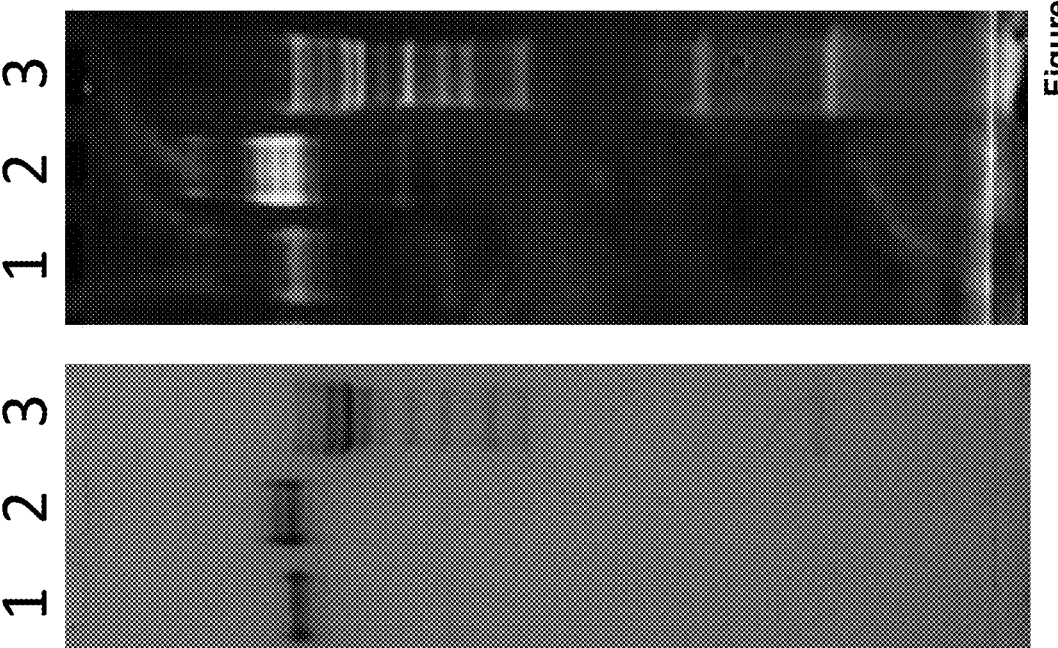
FIG. 8 shows SDS-PAGE of trastuzumab AOCs prepared through different conjugation strategies to demonstrate difference in product homogeneity. The same gel stained with Coomassie blue (left), to indicate the presence of protein, and GelRed (right), to indicate the presence of DNA. 1) Trastuzumab conjugated to 2 ONs via bis-PD 1; 2) Trastuzumab modified via lysines to have an OAR of 2.5; 3) Trastuzumab modified via cysteine capping to have an average loading of 1.9.
Figure 9:
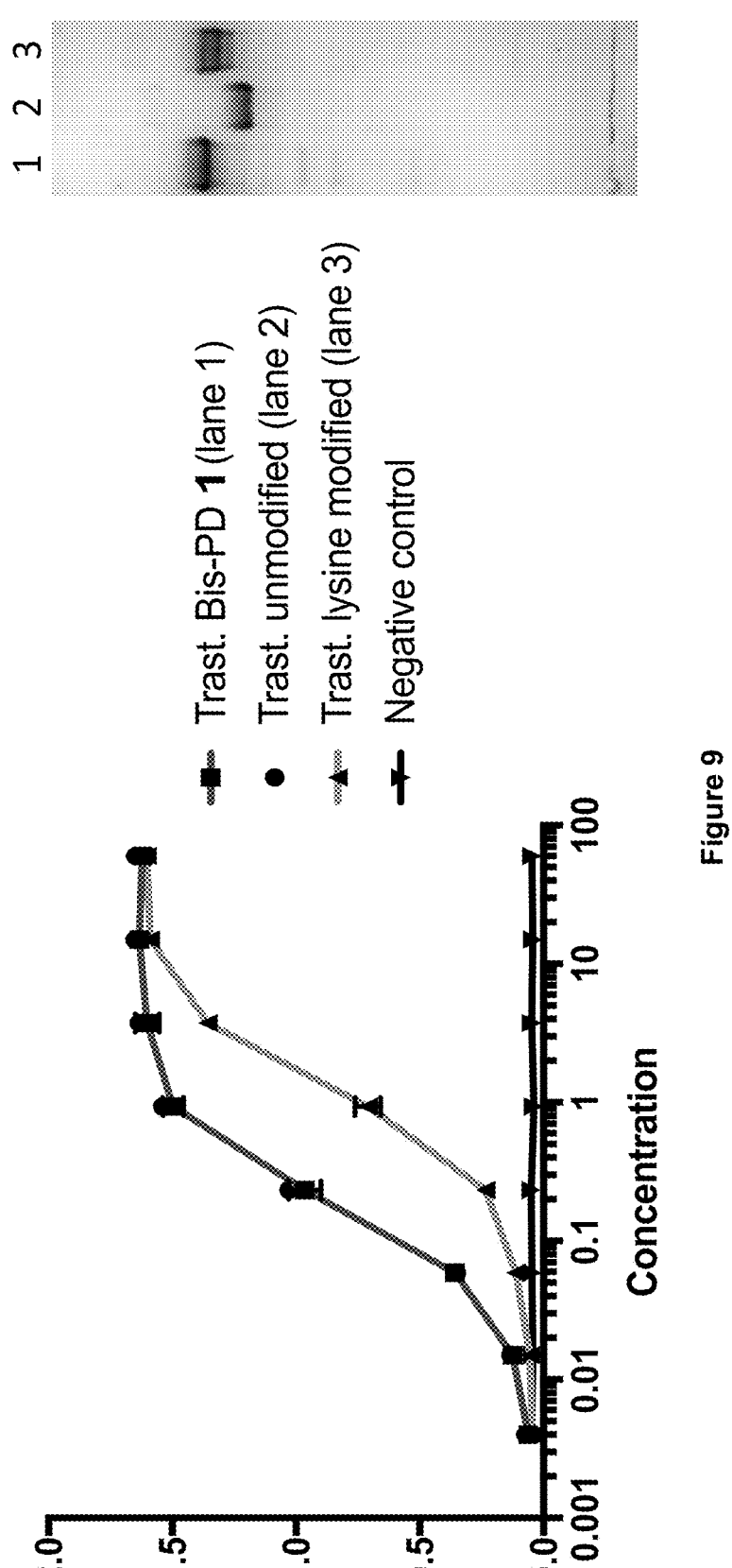
FIG. 9: (Left) ELISA of trastuzumab AOCs prepared via disulfide re-bridging with bis-PD 1 with an of OAR 2.0 (lane 1, SDS-PAGE on right); unmodified trastuzumab (lane 2); lysine-modified trastuzumab with an OAR of 1.7 (lane 3). A significant decrease in binding capability was observed following modification trastuzumab via lysine modification to a similar OAR as that achieved through use of bis-PD 1.

Disulfide re-bridging with bis-PD 1 offered significant improvements in homogeneity over lysine modified and cysteine capping techniques, as assessed by SDS-PAGE. The lysine-modified analogue gave a distribution of intact mAb products corresponding to OARs 0-3, with an average of 1.7-2.5 depending on batch, whereas the cysteine-capped analogue gave a wide array of products corresponding to various combinations of fragments with different loadings of ONs, but with an average overall OAR of 1.9. In comparison, the disulfide re-bridged analogue gave a single band, whose loading was independently validated by MS. In each case, the presence of DNA was confirmed by staining with GelRed (FIG. 8).

Application to Tissue

Two mAbs, previously validated for use in IMC, were chosen to serve as proof of concept examples for application to tissue sections. The two mAbs were anti-alpha smooth muscle actin [1A4] (SMA) and anti-E-cadherin [E-36] (E-Cad) for the structural information they provide within tumour sections. SMA is used as a stain for smooth muscle cells, found in blood vessels and other parenchymal tissues, that provides clear presentation of secondary structures, whereas E-Cad serves well as a membrane marker, which presents cell boundaries and improves segmentation of transcriptomic data. SMA and E-Cad were conjugated with ONs with orthogonal readout sequences via bis-PD 1.

Figure 10:
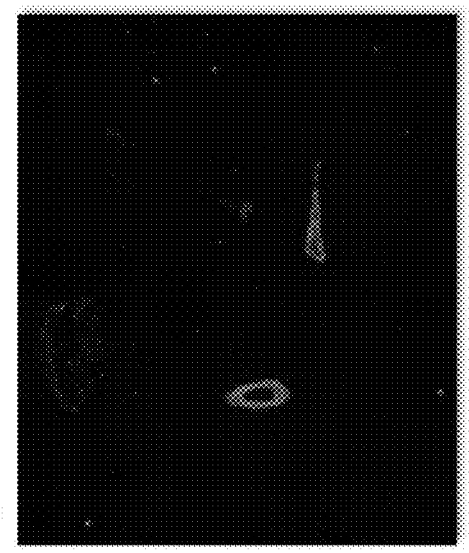
FIG. 10A) DAPI staining of tissue section (PDX cell line); B) the same section stained with SMA-ON conjugate and validated by conventional immunofluorescence; C) the same sample following proteinase K digestion and hybridisation with fluorescently labelled complementary readout probe—the same blood vessel features highlighted by the IF were present following digestion, showing covalent anchoring of the oligonucleotides from the parent conjugate to the gel matrix.
Figure 10:
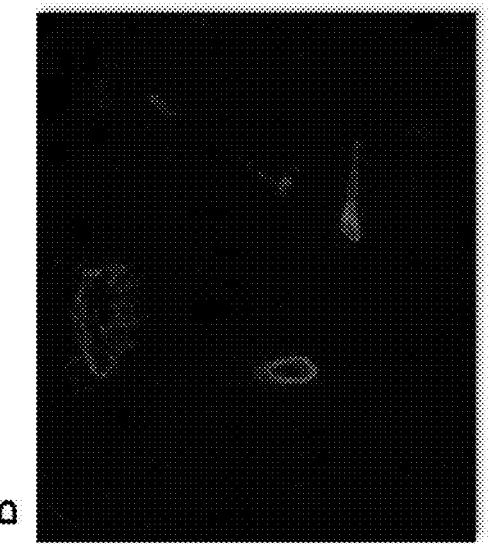
Figure 10:
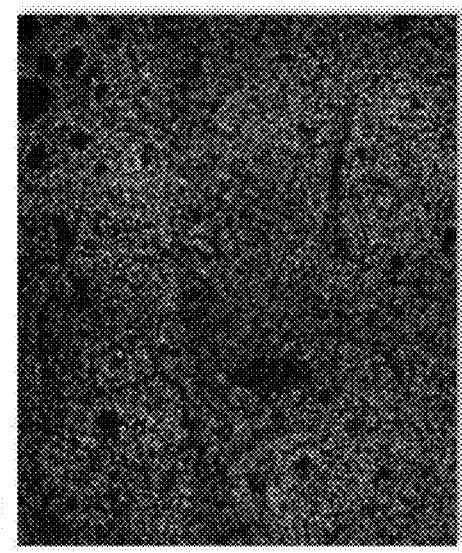

The conjugates of SMA and E-Cad were tested separately to see if their activity had been retained following modification; initially this was done via standard immunofluorescence (IF) staining in tissue; i.e. through the use of fluorescently labelled secondary Ab rather than through hybridisation. When compared with IF staining of their native counterparts, the conjugates showed no appreciable loss in specificity. Following this, the conjugate-stained tissue samples were cast in a polyacrylamide gel and treated with conditions for broad spectrum removal of protein species; leaving behind only a gel matrix with the respective oligonucleotides bound covalently in place. The locations of the oligonucleotides were then recorded through hybridisation with fluorescently labelled readout probes. Gratifyingly, for both conjugates, the images derived from conventional IF were congruent with those derived from the ProFISH readout (FIG. 10). This showed that the encoded ON payloads were still anchored in place at the site of the desired antigen, even following the clearing of all protein species.

To demonstrate the broad applicability of bis-PD 1 to multiple Ab subtypes and the multiplexing ability of the ProFISH technique. ON functionalisation was applied to a panel of 16 Abs chosen to map various antigens of interest relevant gathering. Moreover, due to having a FISH based readout, the ProFISH experiment was run in tandem with MERFISH/STARmap (incl. the mapping of transcripts x, y and z) on the same sample to produce a compiled spatially resolved map of both RNA and protein species from the same sample. In order to demonstrate the advantages of a DNA-based readout method, in situ amplification of conjugated ONs was carried out to deliver an 10× fold increase in brightness. The conjugated ONs were readily susceptible to specific amplification of nucleic acids via intramolecular ligation, or SNAIL, as used in the aforementioned transcript mapping technique, STARmap. SNAIL-based amplification is especially amenable to OAC probes as it only requires 5-nt long barcode sequences and prevents the need to conjugate excessively long ON payloads to Abs whilst still ensuring a high multiplexing ability.

Discussion

Bis-PD 1 offers the ability to functionalise a broad range of Abs with ONs in a site-selective and controlled fashion. The ability to reliably install a limited number of ONs onto various Ab scaffolds without the use of protein engineering stands to significantly improve the field of AOC synthesis. Any degree of error in OAR is significantly increased if conjugates are subjected to DNA amplification. Moreover, if Abs have been modified in a stochastic manner, i.e. via lysine modification or cysteine capping, an average loading of 2 can be achieved but there can be a significant amount of both OAR 0 and OAR 4 present. Given that Abs with OAR 0 are unable to be read via hybridisation, and that those with OAR >3.0 can lose antigen specificity, relying on an average loading significantly reduces the number of viable species for any given non-homogenously modified Ab. Our method of modification with bis-PD 1 not only ensures correct ON loading, but also allows dual functionalisation of Ab scaffolds owing to the ability of PD-based re-bridging agents to bear two N-linked orthogonal functionalities, in this case a branched PEG leading to the SPAAC-ready BCN handle and a terminal acrylamide moiety. Moreover, the 'tying up' of the accessible disulfide network reduces the incidence of non-native disulfide re-bridging, and subsequent fragmentation into the Abs' sub domains. This is a common issue in the field of Ab modification that is difficult to avoid with conventional disulfide re-bridging technologies and unavoidable when employing cysteine capping strategies. Furthermore, PD-based reagents, even when installed on Abs, have excellent tolerance towards a broad range of physiological conditions. While this technology has been demonstrated in an analytical application, OACs generated through the presented method have potential for therapeutic applications; the chemistry could be readily applied to therapeutic ON payloads (anti-sense ONs, siRNA, miRNA etc.).

ProFISH grants the ability to gather spatially resolved multiplexed proteomic data alongside multiplexed transcriptomic data. Moreover, it does so in such a way that the location of all mRNA and protein species of interest can be elucidated through a single FISH-based readout. This technique provides a significant increase in the amount of data that is able to be gathered from a single tissue section. Furthermore, this effect is significantly amplified when using multiple cross sections of a piece of tissue to build up a 3D map of both RNA and protein species. Until recently, due to the inherent incompatibility of the data retrieval techniques for the two sets of information, the best possible resolution achievable was using alternating tissue sections being used to extract alternating sets of data, i.e. one layer being used to map transcriptomic data, the next to map proteomic data.

REFERENCES

1. Sano, T., Smith, C. L. & Cantor, C. R. Immuno-PCR: very sensitive antigen detection by means of specific antibody-DNA conjugates. *Science* (80-.). 258, 120 LP-122 (1992).
2. Schnitzbauer, J., Strauss, M. T., Schlichthaerle, T., Schueder, F. & Jungmann, R. Super-resolution microscopy with DNA-PAINT. *Nat. Protoc.* 12, 1198 (2017).
3. Gullberg, M. et al. Cytokine detection by antibody-based proximity ligation. *Proc. Natl. Acad. Sci. U.S.A.* 101, 8420 LP-8424 (2004).
4. Stoeckius, M. et al. Simultaneous epitope and transcriptome measurement in single cells. *Nat. Methods* 14, 865 (2017).
5. Levin, A. A. Targeting Therapeutic Oligonucleotides. *N. Engl. J. Med.* 376, 86-88 (2017).
6. Levin, A. A. Treating Disease at the RNA Level with Oligonucleotides. *N. Engl. J. Med.* 380, 57-70 (2019).
7. Dovgan, I., Koniev, O., Kolodych, S. & Wagner, A. Antibody—Oligonucleotide Conjugates as Therapeutic, Imaging, and Detection Agents. *Bioconjug. Chem.* (2019). doi:10.1021/acs.bioconjchem.9b00306
8. Stiller, C. et al. Fast and Efficient Fc-Specific Photoaffinity Labeling To Produce Antibody-DNA Conjugates. *Bioconjug. Chem.* 30, 2790-2798 (2019).
9. Kazane, S. A. et al. Site-specific DNA-antibody conjugates for specific and sensitive immuno-PCR. *Proc. Natl. Acad. Sci.* 109, 3731 LP-3736 (2012).
10. Khoshnejad, M. et al. Molecular engineering of antibodies for site-specific covalent conjugation using CRISPR/Cas9. *Sci. Rep.* 8, 1760 (2018).
11. Rosen, C. B. et al. Template-directed covalent conjugation of DNA to native antibodies, transferrin and other metal-binding proteins. *Nat. Chem.* 6, 804-809 (2014).
12. Tran, T. N. N. et al. A Universal DNA-Based Protein Detection System. *J. Am. Chem. Soc.* 135, 14008-14011 (2013).
13. Skovsgaard, M. B., Mortensen, M. R., Palmfeldt, J. & Gothelf, K. V. Aptamer-Directed Conjugation of DNA to Therapeutic Antibodies. *Bioconjug. Chem.* 30, 2127-2135 (2019).
14. Nielsen, T. B. et al. Peptide-Directed DNA-Templated Protein Labelling for The Assembly of a Pseudo-IgM. *Angew. Chemie* 131, 9166-9170 (2019).
15. Bahou, C. et al. Disulfide Modified IgG1: An Investigation of Biophysical Profile and Clinically Relevant Fc Interactions. *Bioconjug. Chem.* 30, 1048-1054 (2019).
16. Giesen, C. et al. Highly multiplexed imaging of tumor tissues with subcellular resolution by mass cytometry. *Nat. Methods* 11, 417 (2014).
17. Chen, K. H., Boettiger, A. N., Moffitt, J. R., Wang, S. & Zhuang, X. Spatially resolved, highly multiplexed RNA profiling in single cells. *Science* (80-.). 348, (2015).
18. Wang, X. et al. Three-dimensional intact-tissue sequencing of single-cell transcriptional states. *Science* (80-.). (2018).
19. Chudasama, V., Maruani, A. & Caddick, S. Recent advances in the construction of antibody-drug conjugates. *Nat Chem* 8, 114-119 (2016).

20. Maruani, A. et al. A plug-and-play approach to antibody-based therapeutics via a chemoselective dual click strategy. *Nat. Commun.* 6, 6645-6654 (2015).

21. Lee, M. T. W., Maruani, A., Baker, J., Caddick, S. & Chudasama, V. Next-generation disulfide stapling: Reduction and functional re-bridging all in one. *Chem. Sci.* 7, 799-802 (2016).

22. Lee, M. T. W. et al. Enabling the controlled assembly of antibody conjugates with a loading of two modules without antibody engineering. *Chem. Sci.* 8, (2017).

23. Harris, L. J., Skaletsky, E. & McPherson, A. Crystallographic structure of an intact IgG1 monoclonal antibodyl. *J. Mol. Biol.* 275, 861-872 (1998).

24. Bahou, C. et al. Highly homogeneous antibody modification through optimisation of the synthesis and conjugation of functionalised dibromopyridazinediones. *Org. Biomol. Chem.* 16, 1359-1366 (2018).

25. G. Gut et al; Multiplexed protein maps link subcellular organization to cellular states, *Science.* 2018 Aug. 3; 361 (6401).

26. Y. Goltsev et al, Deep Profiling of Mouse Splenic Architecture with CODEX Multiplexed Imaging; *Cell.* 2018 Aug. 9; 174 (4): 968-981.

27. F. Chen et al; *Optical imaging. Expansion microscopy.* Science. 2015 January 30; 347 (6221): 543-8.

Detailed Synthesis

All reagents were purchased from Aldrich, AlfaAesar or Tebu-Bio and were used as received. Where described below petrol refers to petroleum ether (40-60° C.). All reactions were monitored by thin-layer chromatography (TLC) on pre-coated SIL G/UV254 silica gel plates (254 µm) purchased from VWR. Flash chromatographic purifications were carried out using CombiFlash Rf (Teledyne Isco) with RediSepRf columns. 1H and 13C NMR spectra were recorded at ambient temperature using an internal deuterium lock on Bruker DPX (400 MHz; $^1$H-$^{13}$C DUL probe), Bruker Avance III HD (400 MHz; Smart probe), Bruker Avance III HD (500 MHz; Smart probe) and Bruker Avance III HD (500 MHz; DCH Cryoprobe). The chemical shifts (δ) for 1H and 13C are quoted relative to residual signals of the solvent on the ppm scale. 1H NMR peaks are reported as singlet (s), doublet (d), triplet (t), quartet (q), pentuplet (p), doublet of doublets (dd), m (multiplet) and br (broad). Coupling constants (J values) are reported in Hertz (Hz) and are H—H coupling constants unless otherwise stated. Signal multiplicities in 13C NMR were determined using the distortionless enhancement by phase transfer (DEPT) spectral editing technique. Infrared spectra were obtained on a Perkin Elmer Spectrum 100 FTIR Spectrometer operating in ATR mode with frequencies given in reciprocal centimetres (cm$^{-1}$). Liquid chromatography-mass spectrometry (LC-MS) of small molecules were measured on a Bruker amaZon X Ion Trap MS, with Kinetex C18 column (Phenomenex, 50×2.1 mm, 2.6 µm); high resolution mass spectrometry was performed on a Waters Xevo G2-S QToF. Oligonucleotides (ONs) were ordered from IDT; oligo-azide and oligo-NH$_2$ refer to IDT custom oligos synthesised to feature and azide (—N$_3$) or amine (—NH$_2$) at the 5' end, respectively.

LC-MS Analysis of Oligonucleotides (ONs)

LC-MS of oligonucleotides was performed on a Bruker amaZon X system, using a XTerra™ MS C18 column (2.1×50 mm, 2.5 µm particle size), with 100 mM 1,1,1,3,3, 3-hexafluoro-2-propanol; 10 mM Et$_3$N (solvent A) and MeOH (solvent B) at a flow-rate of 0.2 mL/min. The column was pre-equilibrated at 15% B for 10 min and followed by a gradual increase to 20% B over a duration of 25 min. Reaction conversion was calculated by integration of UV signals of the starting material and product(s) at 260 nm. Identity of the product(s) was confirmed by ESI-MS with negative polarity in ultra-scan mode. Data was acquired between 1000-2800 m/z.

Synthesis of N-(3-bromopropyl) acrylamide[1]

Figure 11:
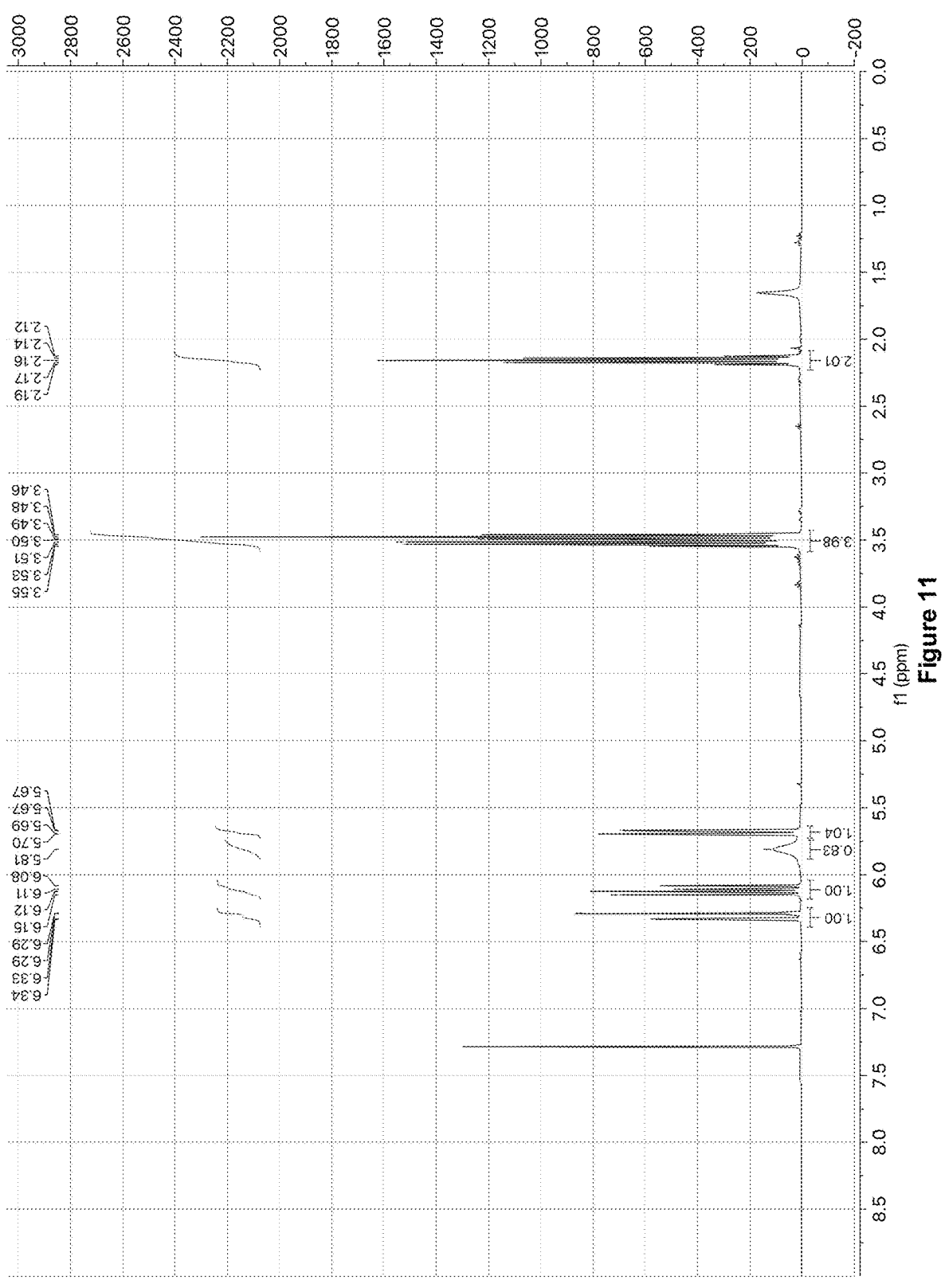
Figure 12:
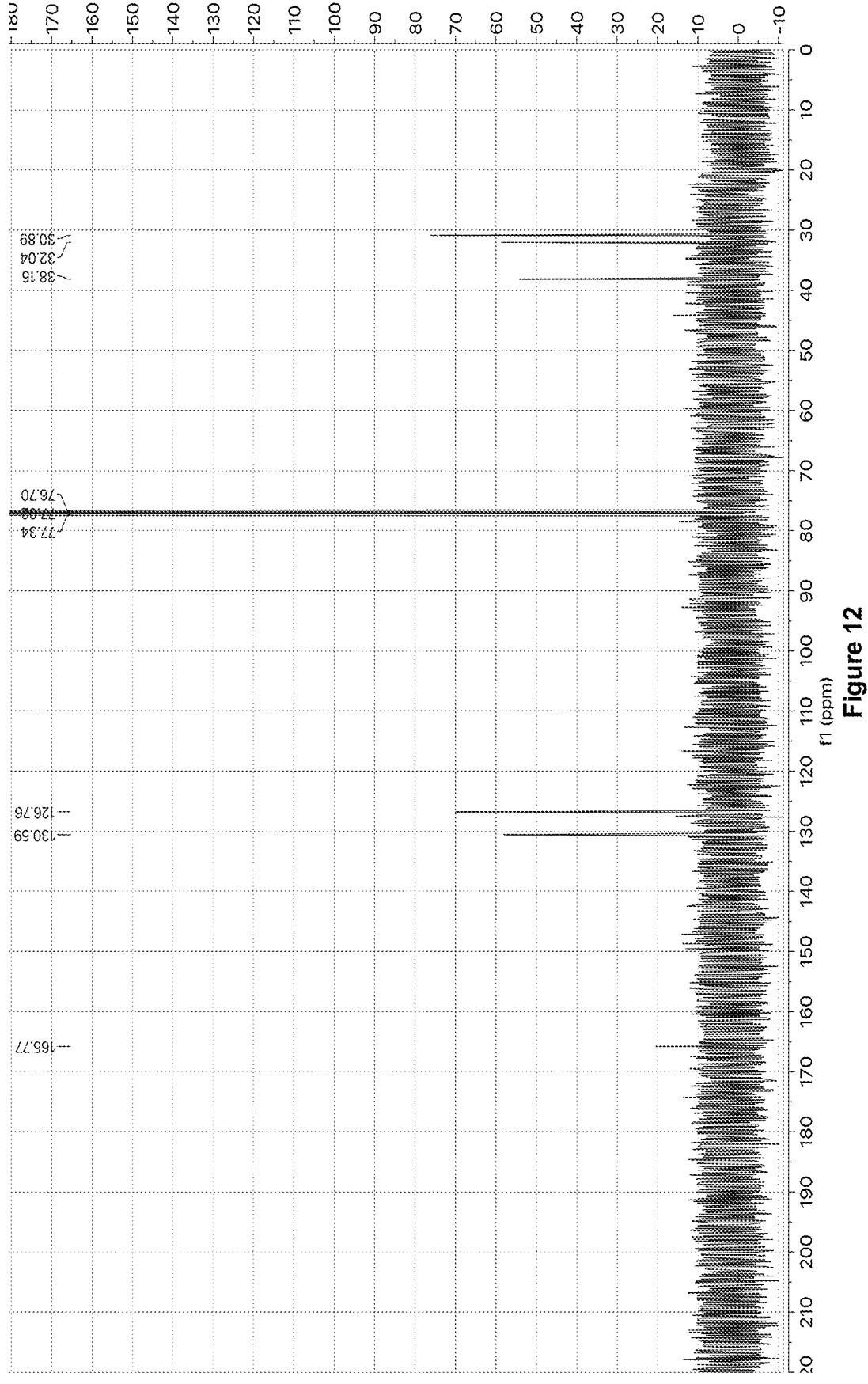

To a solution of 3-bromopropylamine hydrobromide (10.0 g, 45.6 mmol) and triethylamine (15.9 mL, 50.7 mmol) in H$_2$O (100 mL) at 0° C. was slowly added acryloyl chloride (4.1 mL, 50.7 mmol), and the reaction was allowed to warm to 21° C. and stirred for 1 h. After this time the reaction was again cooled to 0° C. and adjusted to pH 7.0 with 6 M hydrochloric acid. The neutralised mixture was then extracted with EtOAC (4×50 mL), and the combined organic phases were washed with saturated NaHCO$_3$ aq. (2×50 mL), citric acid aq. (10%, 2×50 mL), and saturated NaCl aq. (2×50 mL). The organic phase was then dried (MgSO$_4$) and concentrated in vacuo to give N-(3-bromopropyl) acrylamide (5.5 g, 63%) as a pale yellow oil. $^1$H NMR (400 MHz, CDCl3) δ 6.31 (dd, J=17.0, 1.4 Hz, 1H), 6.11 (dd, J=17.0, 10.3 Hz, 1H), 5.81 (br. s, 1H), 5.68 (dd, J=10.3, 1.4 Hz, 1H), 3.52 (q, J=6.5 Hz, 2H), 3.48 (t, J=6.5 Hz, 2H), 2.16 (p, J=6.5 Hz, 2H); $^{13}$C NMR (100 MHz, CDCl3) δ 165.8 (C), 130.6 (CH), 126.8 (CH$_2$), 38.2 (CH$_2$), 32.0 (CH$_2$), 30.9 (CH$_2$); IR (thin film) 3381, 2941, 1731, 1671, 1617, 1538 cm$^{-1}$; LRMS (ES+) 192.15 (100, [M$^{79}$Br+H]$^+$); HRMS (ES+) calcd. for C$_6$H$_{11}$BrNO$^+$ [M$^{79}$Br+H]$^+$192.0019, observed 192.0016. Spectra shown in FIGS. 11 and 12.

Figure 13:
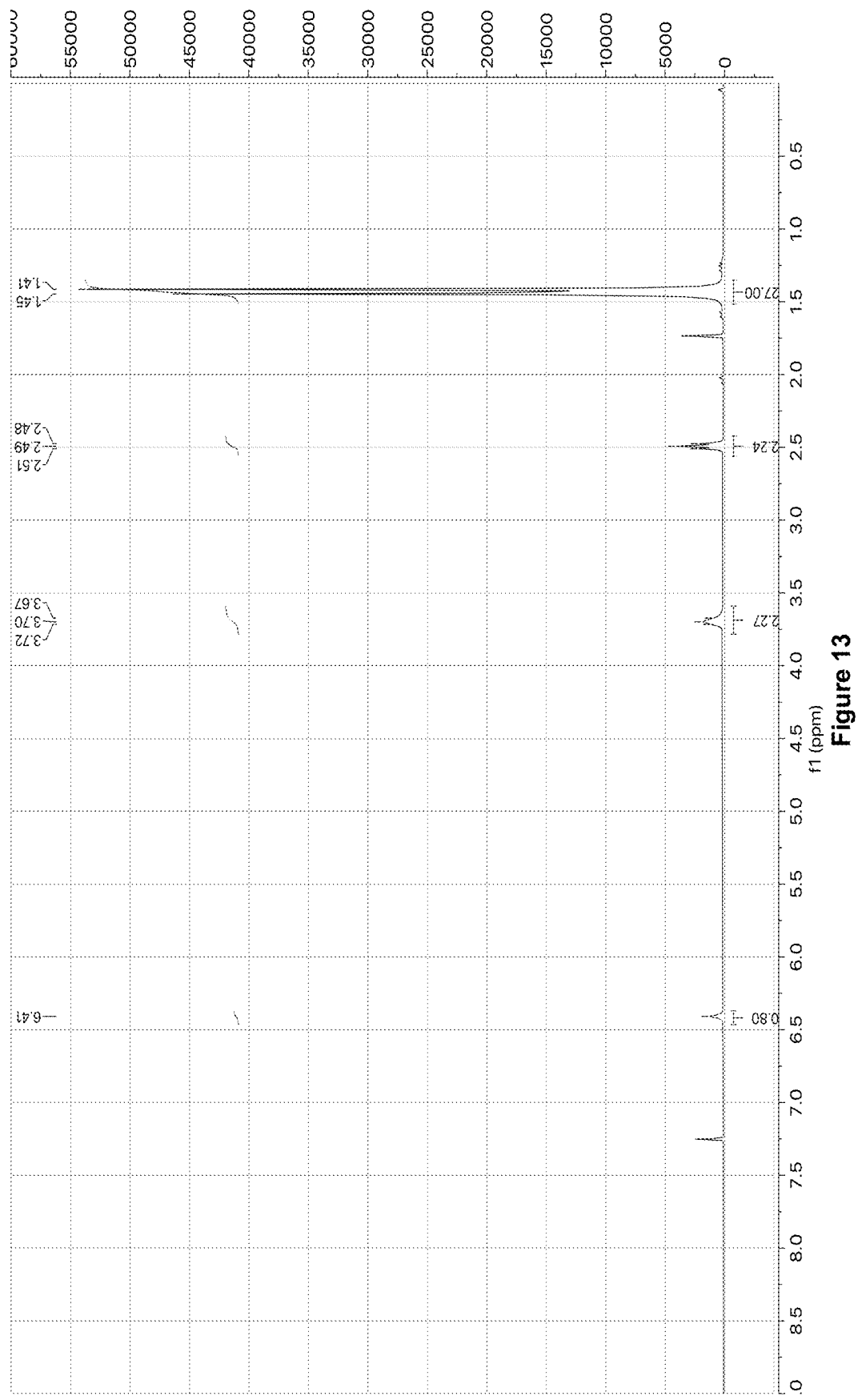
Figure 14:
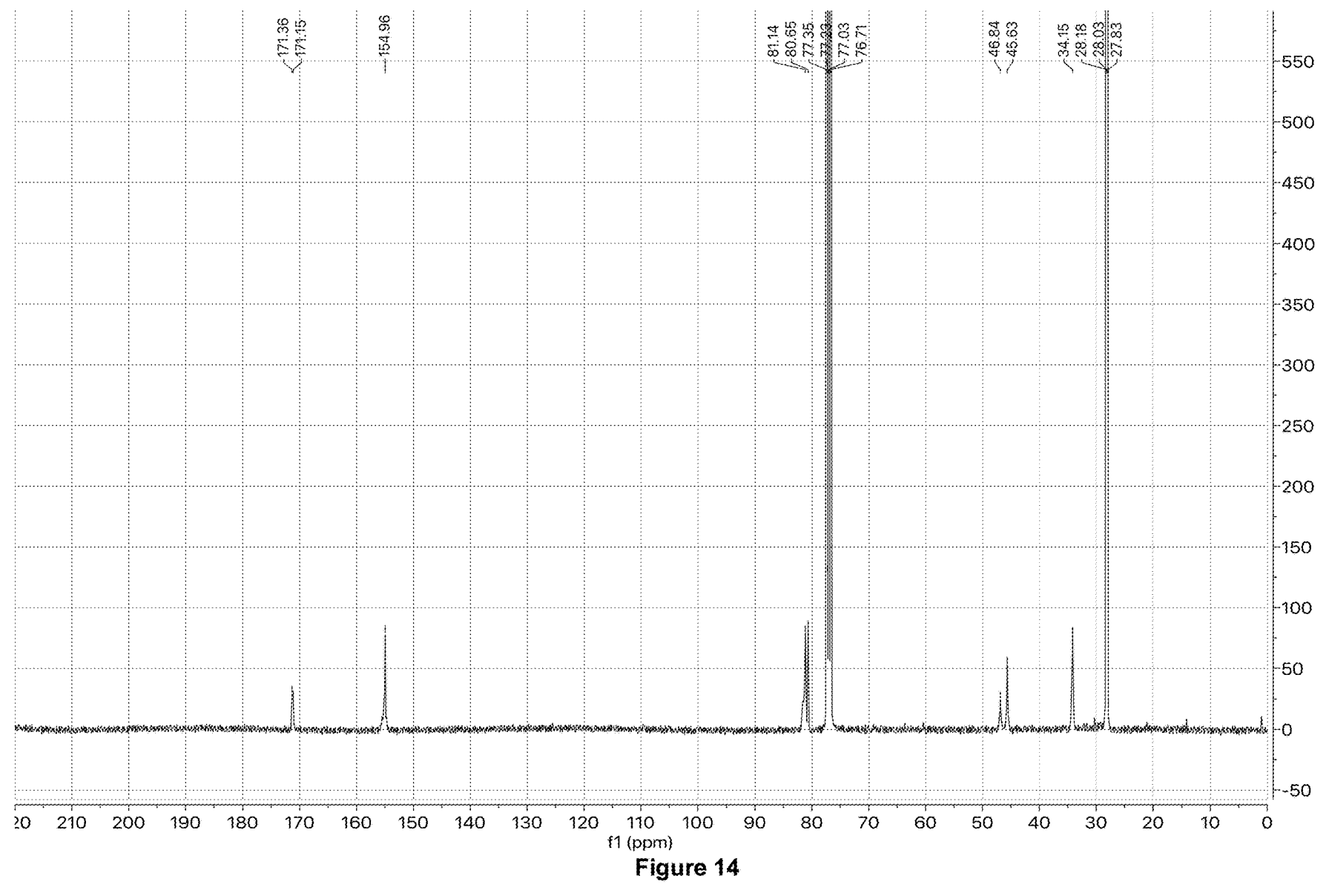

Synthesis of di-tert-butyl 1-(3-(tert-butoxy)-3-oxo-propyl) hydrazine-1,2-dicarboxylate To a solution of di-tert-butyl hydrazine-1,2-dicarboxylate (3.0 g, 12.9 mmol) in t-BuOH (15 mL) was added NaOH aq. (10%, 0.5 mL) and stirred for 10 mins at 21° C. After this time tert-butyl acrylate (2.0 g, 15.5 mmol) was added and the reaction was stirred for 16 h at 60° C. After this time the reaction mixture was concentrated in vacuo and the resultant residue was dissolved in EtOAc (50 mL), which was washed with H$_2$O (25 mL) and saturated NaCl aq. (25 mL). The organic phase was then dried (MgSO$_4$) and concentrated in vacuo. The crude residue was purified by flash column chromatography (10% EtOAc/petrol) to give di-tert-butyl 1-(3-(tert-butoxy)-3-oxopropyl) hydrazine-1,2-dicarboxylate (2.5 g, 50%) as a clear oil. $^1$H NMR (400 MHz, CDCl$_3$) δ 6.41 (br. s, 1H), 3.74 (br. t, J=6.9 Hz, 2H), 2.54 (t, J=6.9 Hz, 2H), 1.53-1.43 (m, 27H); $^{13}$C NMR (100 MHz, CDCl$_3$) (major rotamer) δ 171.4 (C), 171.1 (C), 155.0 (C), 81.5 (C), 81.1 (C), 80.7 (C), 45.6 (CH$_2$), 34.2 (CH$_2$), 28.2 (CH$_3$), 28.0 (CH$_3$); IR (thin film) 3319, 2978, 1708, 1456 cm$^{-1}$; LRMS (ES+) 361.32 (100, [M+H]$^+$); HRMS (ES+) calcd. for C$_{17}$H$_{32}$N$_2$NaO$_6$$^+$ [M+Na]$^+$ 383.2153, observed 383.2155. Spectra shown in FIGS. 13 and 14.

Figure 15:
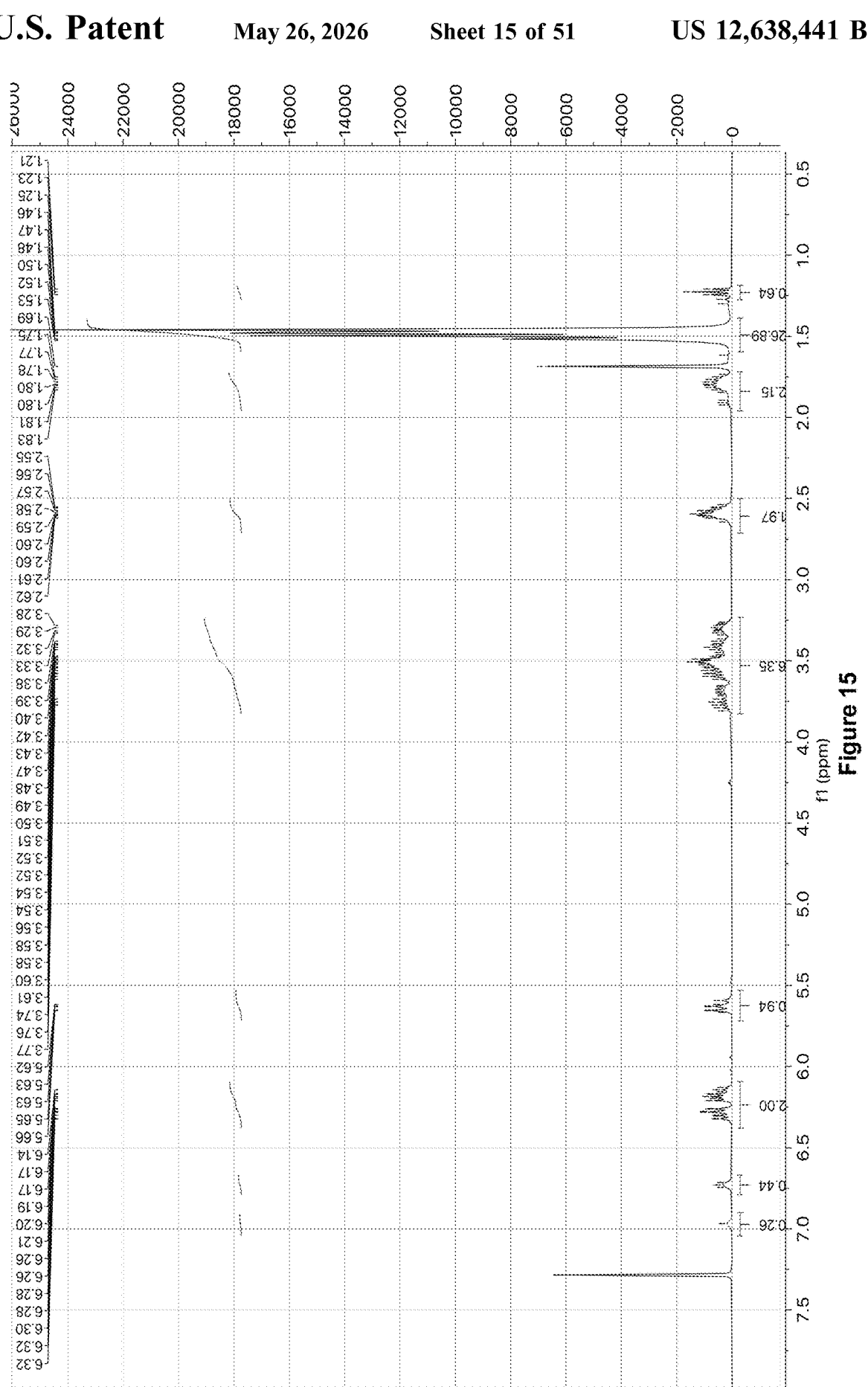
Figure 16:
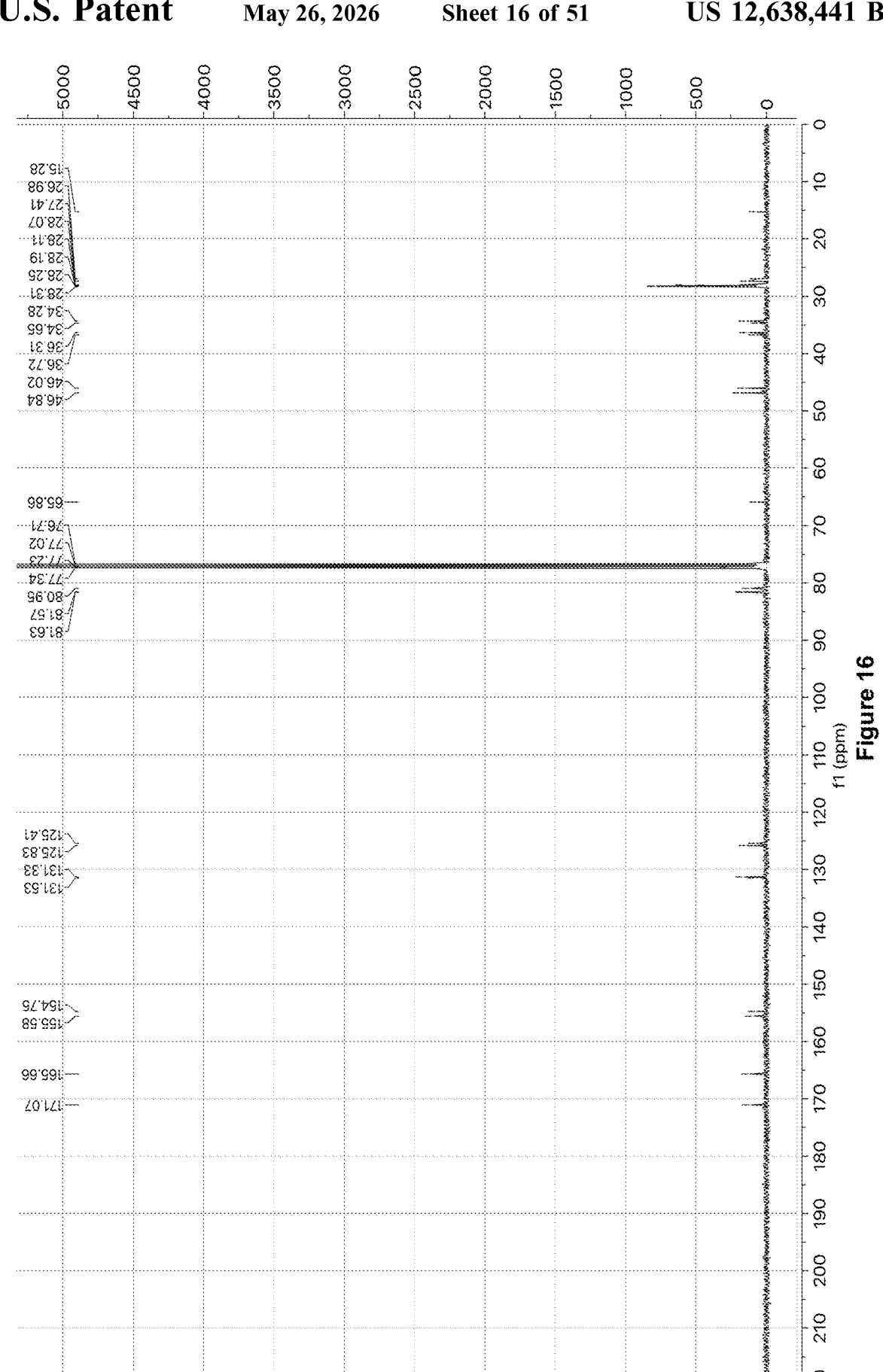

Synthesis of di-tert-butyl 1-(3-acrylamidopropyl)-2-(3-(tert-butoxy)-3-oxopropyl) hydrazine-1,2-dicarboxylate To a solution of di-tert-butyl 1-(3-(tert-butoxy)-3-oxopropyl) hydrazine-1,2-dicarboxylate 3 (2.3 g, 6.4 mmol) and N-(3-bromopropyl) acrylamide (1.8 g, 9.6 mmol) in DMF (40 mL) was added Cs$_2$CO$_3$ (4.2 g, 12.7 mmol) and stirred at 21° C. for 72 h. After this time the reaction mixture was diluted with H$_2$O (100 mL) and extracted with Et$_2$O (4×50 mL). The organic phases were combined and washed with saturated NaCl aq. (2×50 mL) and then dried (MgSO$_4$). The solution was then concentrated in vacuo and purified by flash column chromatography (10-90% EtOAc/petrol) to give di-tert-butyl 1-(3-acrylamidopropyl)-2-(3-(tert-butoxy)-3-oxopropyl) hydrazine-1,2-dicarboxylate (1.94 g, 65%) as a clear oil. $^1$H NMR (400 MHz, CDCl3) (major rotamer) δ 6.72 (br. s, 1H), 6.34-6.11 (m, 2H), 5.68-5.58 (m, 1H), 3.82-3.22 (m, 6H), 2.66-2.52 (m, 2H), 1.84-1.73 (m, 2H), 1.56-1.40 (m, 27H); $^{13}$C NMR (100 MHz, CDCl3) (major rotamer) δ 171.1 (C), 165.7 (C), 155.6 (C), 154.8 (C), 131.3 (CH), 125.8 (CH2), 81.6 (C), 81.6 (C), 81.0 (C), 46.8 (CH2), 46.0 (CH2), 36.3 (CH2), 34.3 (CH2), 28.3 (CH3), 28.3 (CH3), 28.1 (CH3); IR (thin film) 3291, 2977, 1708, 1628 cm$^{-1}$; LRMS (ES+) 472.56 (100, [M+H]$^+$); HRMS (ES+) calcd. for C$_{23}$H$_{42}$N$_3$O$_7$$^+$ [M+H]$^+$ 472.3017, observed 472.3047. Spectra shown in FIGS. 15 and 16.

Synthesis of 3-(2-(3-acrylamidopropyl)-4,5-dibromo-3,6-dioxo-3,6-dihydropyridazin-1 (2H)-yl) propanoic acid (4)

Figure 17:
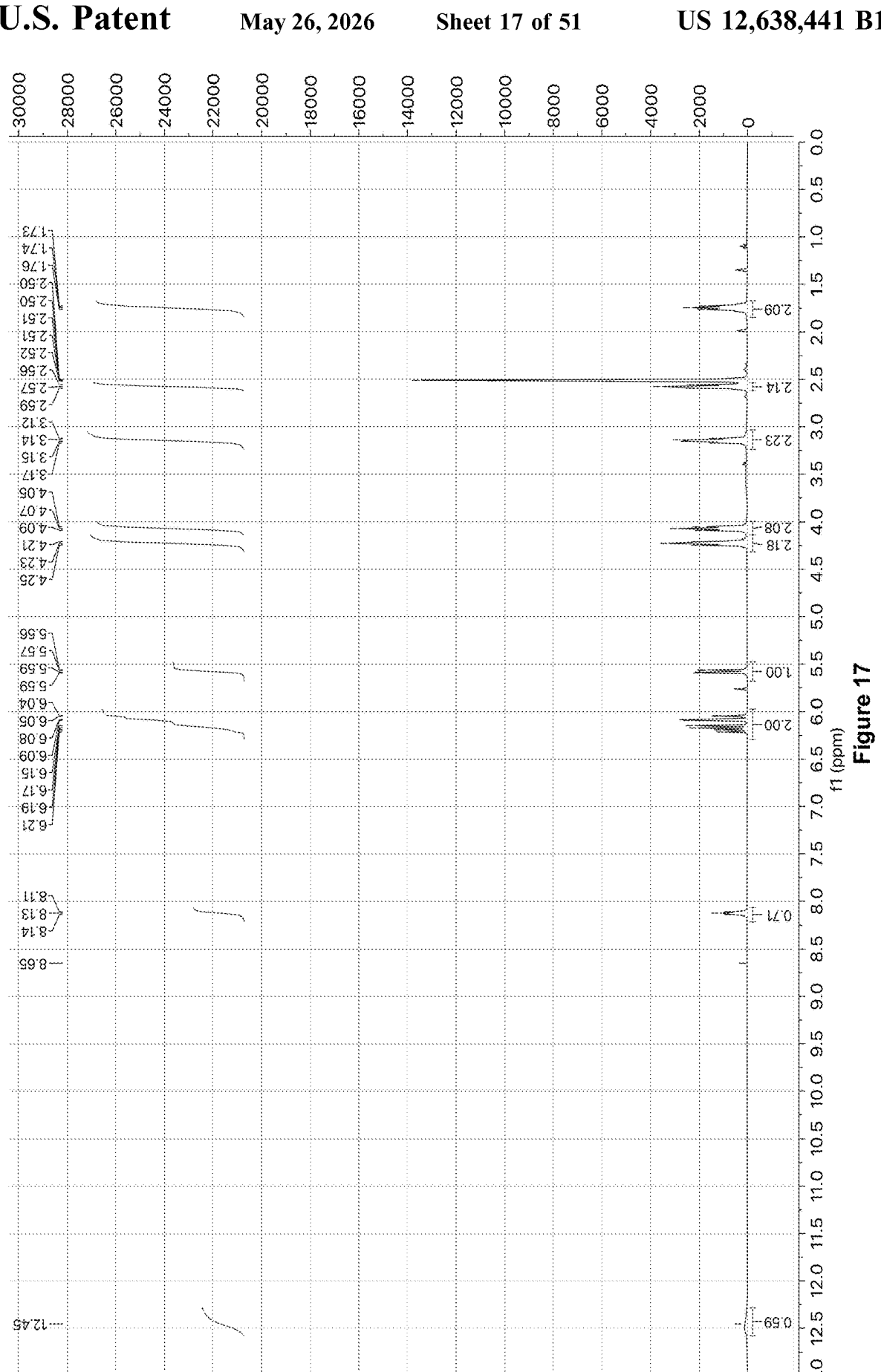
Figure 18:
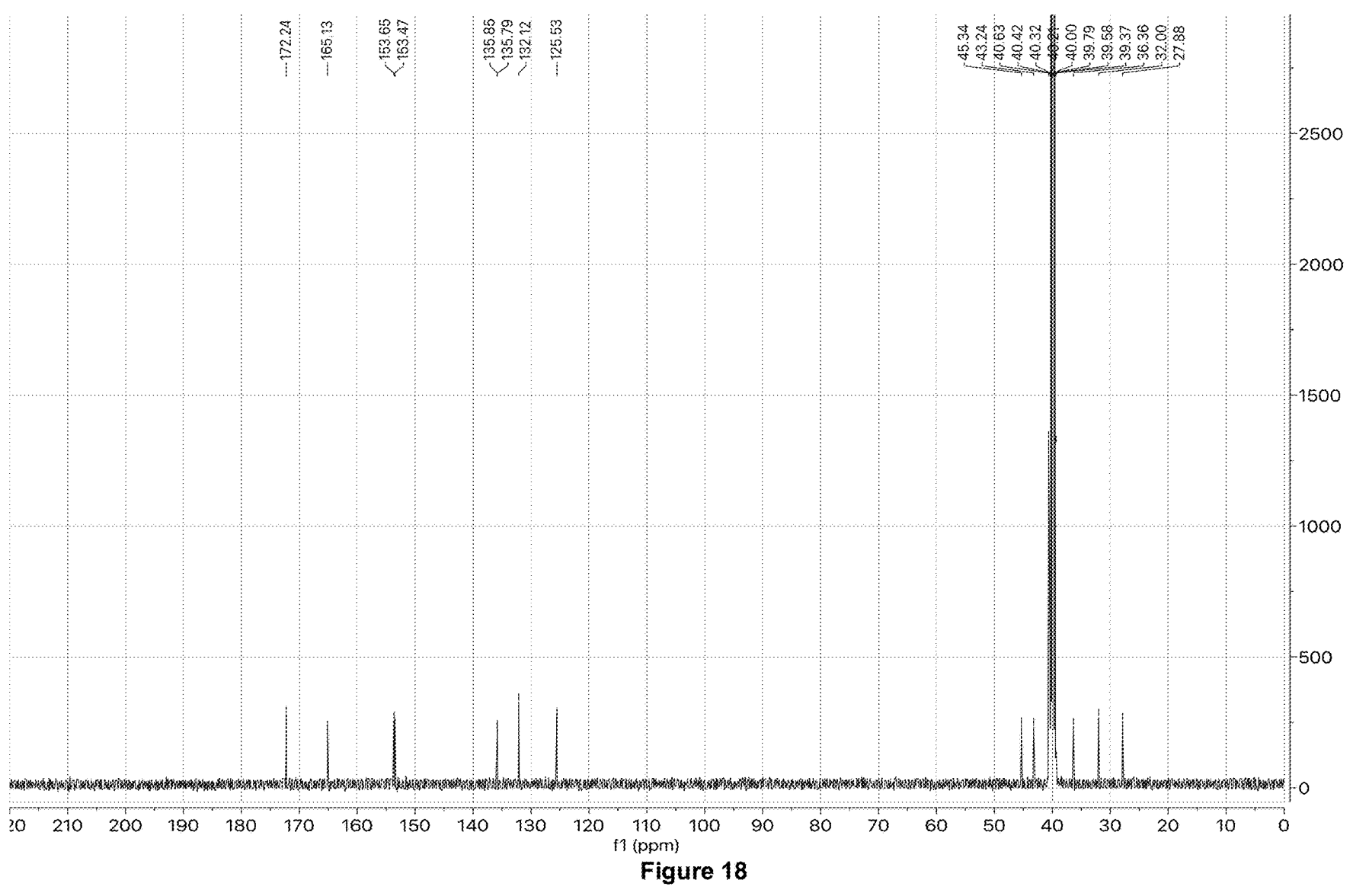

Dibromomaleic acid (1.2 g, 4.4 mmol) was dissolved in AcOH (50 mL) and heated under reflux (130° C.) for 30 min. To this solution, was added di-tert-butyl 1-(3-acrylamidopropyl)-2-(3-(tert-butoxy)-3-oxopropyl) hydrazine-1,2-dicarboxylate 3 (1.9 g, 4.0 mmol) and the reaction heated under reflux for a further 2 h. After this time, the reaction mixture was concentrated in vacuo and the crude residue purified by flash column chromatography (60-100% EtOAc/petrol) to give 3-(2-(3-acrylamidopropyl)-4,5-dibromo-3,6-dioxo-3,6-dihydropyridazin-1(2H)-yl)propanoic acid (458 mg, 1.01 mmol, 25%) as a pale yellow amorphous solid. 1H NMR (400 MHz, DMSO) δ 12.47 (br. s, 1H), 8.13 (t, J=5.7 Hz, 1H), 6.24-6.01 (m, 2H), 5.58 (dd, J=9.9, 2.4 Hz, 1H), 4.23 (t, J=7.2 Hz, 2H), 4.07 (t, J=7.2 Hz, 2H), 3.20-3.10 (m, 2H), 2.57 (t, J=7.2 Hz, 2H), 1.74 (p, J=7.2 Hz, 2H); $^{13}$C NMR (100 MHz, DMSO) δ 172.2 (C), 165.1 (C), 153.7 (C), 153.5 (C), 135.9 (C), 135.8 (C), 132.1 (CH), 125.5 (CH2), 45.3 (CH2), 43.2 (CH2), 36.4 (CH2), 32.0 (CH2), 27.9 (CH2); IR (thin film) 3331, 2951, 2669, 2522, 1714, 1650, 1542 cm$^{-1}$; LRMS (ES+) 454.20 (100, [M$^{80}$Br$^{79}$Br+H]$^+$); HRMS (ES+) calcd. for C$_{13}$H$_{16}$Br$_2$N$_3$O$_5$$^+$ [M$^{80}$Br$^{79}$Br+H]$^+$ 453.9431, observed 453.9419. Spectra shown in FIGS. 17 and 18.

Synthesis of 14-(2,2-dimethyl-4-oxo-3,8,11-trioxa-5-azatridecan-13-yl)-2,2-dimethyl-4,15-dioxo-3,8, 11,18,21,24-hexaoxa-5,14-diazaheptacosan-27-oic acid (bis-NH-Boc 7)

Figure 19:
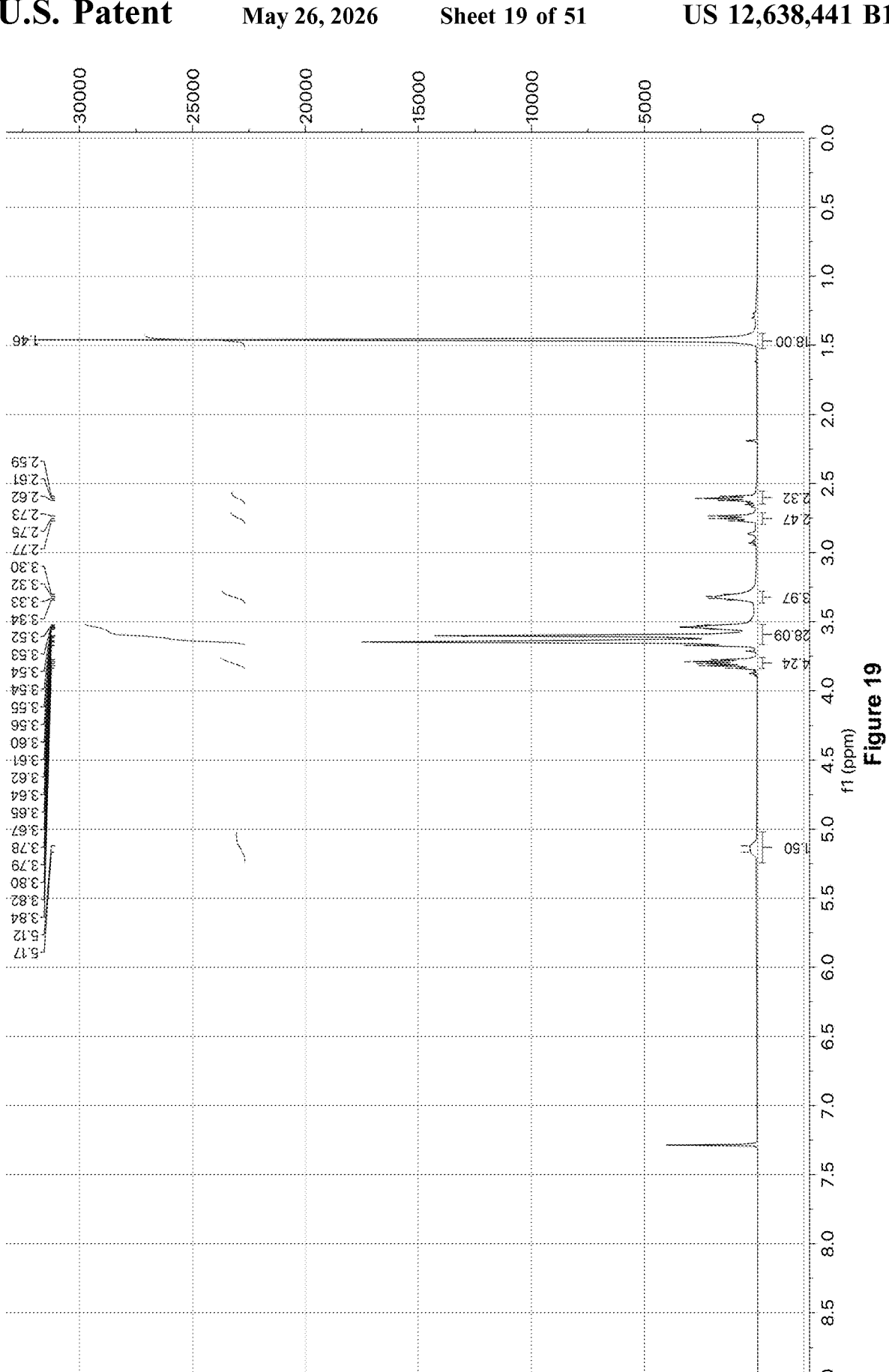
Figure 20:
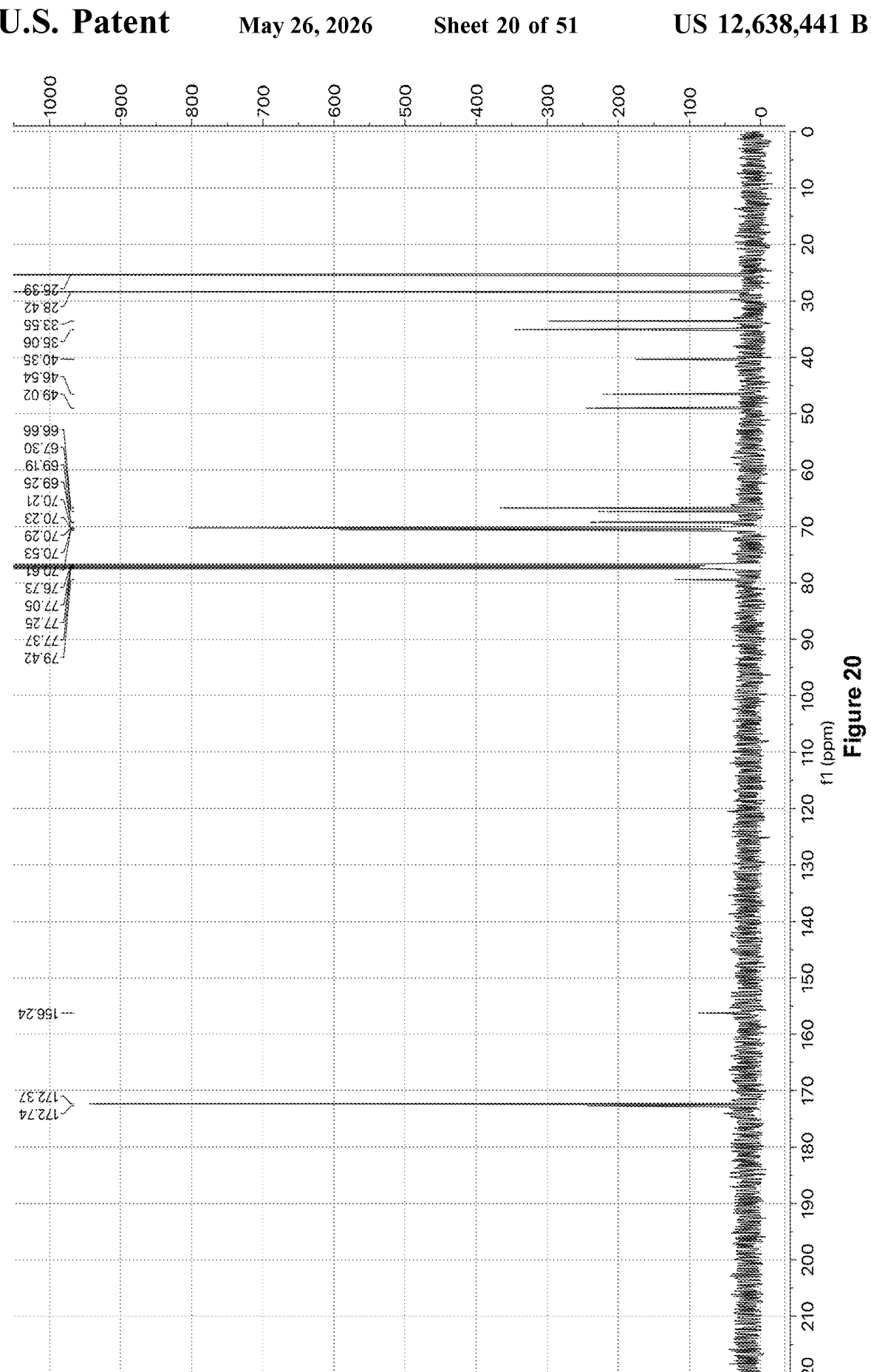

To a solution of di-tert-butyl (3,6,12,15-tetraoxa-9-aza-heptadecane-1,17-diyl)dicarbamate 5 (138 mg, 0.29 mmol) and $Et_3N$ (29.2 mg, 42 μL, 0.29 mmol) in DCM (5 mL) was added 3-(2-(2-(3-(2,5-dioxopyrrolidin-1-yl)-3-oxopropoxy) ethoxy)ethoxy)propanoic acid 6 (100 mg, 0.29 mmol) and stirred at 21° C. for 16 h. After this time, the reaction mixture was concentrated in vacuo and the crude residue was purified by flash column chromatography (0-10% MeOH/DCM) to give bis-NH-Boc (55 mg, 0.08 mmol, 27%) as a yellow oil: $^1H$ NMR (400 MHz, CDCl3) δ 5.15 (br. s, 2H), 3.84-3.76 (m, 4H), 3.68-3.51 (m, 28H), 3.36-3.26 (m, 4H), 2.75 (t, J=7.6 Hz, 2H), 2.61 (t, J=5.9 Hz, 2H), 1.46 (s, 18H); $^{13}C$ NMR (100 MHz, CDCl3) δ 172.8 (C), 172.5 (C), 156.1 (C), 79.3 (C), 70.7 (CH2), 70.6 (CH2), 70.3 (CH2), 70.3 (CH2), 70.2 (CH2), 69.4 (CH2), 69.2 (CH2), 67.3 (CH2), 66.8 (CH2), 49.0 (CH2), 46.5 (CH2), 40.4 (CH2), 35.2 (CH2), 33.6 (CH2), 28.4 (CH3); IR (thin film) 3360, 2975, 2931, 2872, 1707, 1522 $cm^{-1}$; LRMS (ES−) 710.92 (100, $[M–H]^-$); HRMS (ES+) calcd. for $C_{32}H_{62}N_3O_{14}^+$ $[M+H]^+$ 712.4226, observed 712.4254. Spectra shown in FIGS. 19 and 20.

Synthesis of 1-(2-(3-acrylamidopropyl)-4,5-di-bromo-3,6-dioxo-3,6-dihydropyridazin-1(2H)-yl)-13-(2-(2-(2-(3-(2-(3-acrylamidopropyl)-4,5-di-bromo-3,6-dioxo-3,6-dihydropyridazin-1(2H)-yl) propanamido)ethoxy)ethoxy)ethyl)-3,14-dioxo-7,10, 17,20,23-pentaoxa-4,13-diazahexacosan-26-oic acid (bis-PD 9)

To a solution of 3-(2-(3-acrylamidopropyl)-4,5-dibromo-3,6-dioxo-3,6-dihydropyridazin-1 (2H)-yl) propanoic acid (100 mg, 0.22 mmol) in THF (5 mL) was added DCC (50 mg, 0.24 mmol), and the reaction mixture was stirred for 30 mins at 0° C. After this time, N-hydroxysuccinimide (27 mg, 0.24 mmol) was added to the reaction mixture, which was then allowed to warm to 21° C. and stirred for 16 h. After this time, the reaction mixture was filtered and the filtrate was concentrated in vacuo. The crude residue was then purified by flash column chromatography (20-100% EtOAc/petrol) to give 2,5-dioxopyrrolidin-1-yl 3-(2-(3-acrylamidopropyl)-4,5-dibromo-3,6-dioxo-3,6-dihydropyridazin-1 (2H)-yl) propanoate (PD-NHS 2) (90 mg, 0.17 mmol, 75%) as a yellow gum: LRMS (ES+) 551.19 (100, [M$^{79}$Br$^{79}$Br$^{80}$Br $^{80}$Br+H]$^+$). Meanwhile, bis-NH-Boc underwent amine-deprotection: To a solution of bis-NH-Boc in DCM (2.5 mL) was added TFA (2.5 mL) and stirred at 21° C. for 30 min. After this time the reaction mixture was concentrated in vacuo to give bis-NH$_2$ 5: LRMS (ES–)

Figure 21:
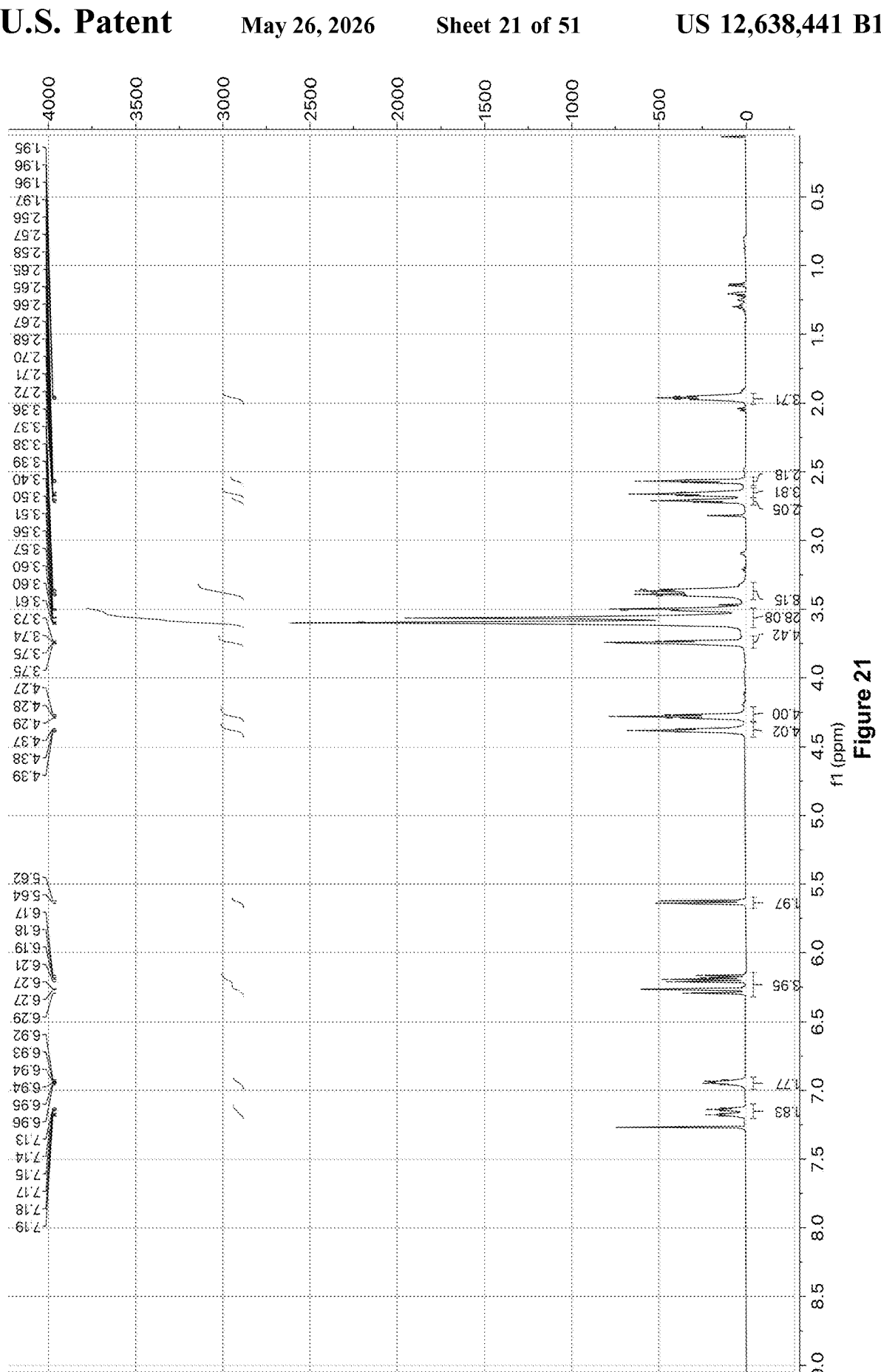
Figure 22:
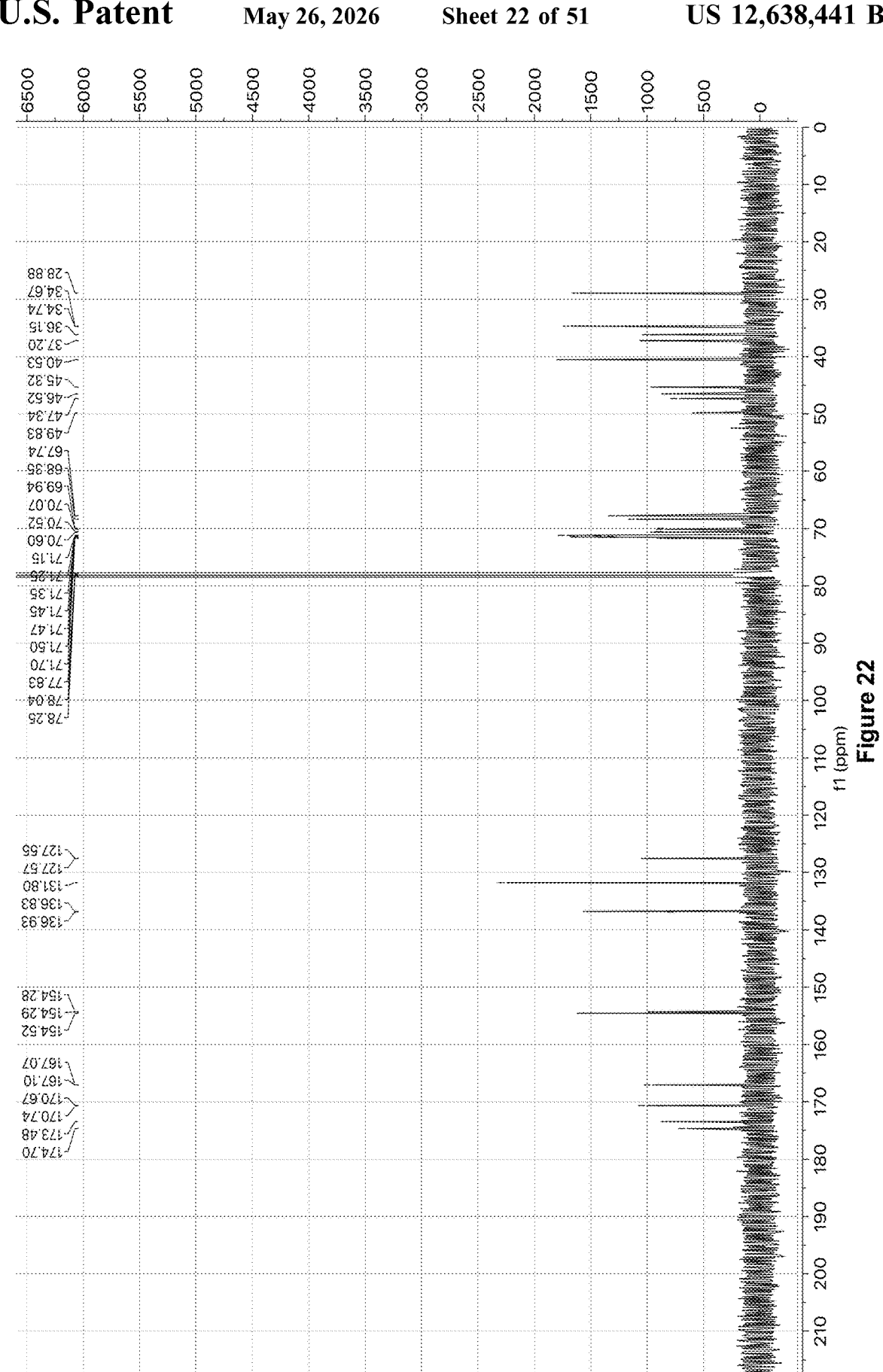

(CH), 127.6 (CH2), 71.7 (CH2), 71.5 (CH2), 71.5 (CH2), 71.5 (CH2), 71.4 (CH2), 71.3 (CH2), 71.2 (CH2), 71.2 (CH2), 70.6 (CH2), 70.5 (CH2), 70.1 (CH2), 69.9 (CH2), 68.4 (CH2), 67.7 (CH2), 49.8 (CH2), 47.3 (CH2), 46.5 (CH2), 45.3 (CH2), 40.5 (CH2), 37.2 (CH2), 36.2 (CH2), 34.7 (CH2), 28.9 (CH2); IR (thin film) 3352, 3032, 2941, 1710, 1629, 1536 cm$^{-1}$; LRMS (ES–) 1380.21 (100, [M$^{80}$Br$^{80}$Br$^{79}$B$^{79}$Br–H]$^-$); HRMS (ES+) calcd. for C$_{48}$H$_{72}$Br$_4$N$_9$O$_{18}^+$ [M$^{80}$Br$^{80}$Br$^{79}$B $^{79}$Br+H]$^+$ 1382.1682, observed 1382.1180. Spectra shown in FIGS. 21 and 22.

Synthesis of ((1R,8S,9s)-bicyclo[6.1.0]non-4-yn-9-yl)methyl (35-(2-(3-acrylamidopropyl)-4,5-dibromo-3,6-dioxo-3,6-dihydropyridazin-1 (2H)-yl)-23-(2-(2-(2-(3-(2-(3-acrylamidopropyl)-4,5-dibromo-3,6-dioxo-3,6-dihydropyridazin-1 (2H)-yl)propanamido)ethoxy)ethoxy)ethyl)-10,22,33-trioxo-3,6,13,16,19,26,29-heptaoxa-9,23,32-triazapentatriacontyl) carbamate (bis-PD1)

510.75 (100, [M–H]$^-$). Subsequently, to a solution of bis-NH$_2$ 5 (57 mg, 0.08 mmol) and Et$_3$N (16 mg, 22 μL, 0.16 mmol) in MeCN (5 mL) was added PD-NHS 2 (85 mg, 0.16 mmol) and stirred for 16 h at 21° C. After this time, the reaction mixture was concentrated in vacuo and the crude residue was purified by flash column chromatography (10-60% MeOH/EtOAc). The appropriate fractions were collected and concentrated in vacuo, the resulting residue was re-dissolved in DCM and filtered to remove excess silica. The filtrate was concentrated in vacuo to give bis-PD 6 (49 mg, 0.04 mmol, 46%) as a yellow gum: $^1$H NMR (600 MHz, CDCl$_3$) (major rotamer) δ 7.14 (t, J=5.6 Hz, 2H), 6.94 (dt, J=9.6, 6.0 Hz, 2H), 6.31-6.15 (m, 4H), 5.63 (d, J=10.3 Hz, 2H), 4.37 (t, J=7.2 Hz, 4H), 4.28 (t, J=7.1 Hz, 4H), 3.77-3.72 (m, 4H), 3.63-3.48 (m, 28H), 3.42-3.33 (m, 8H), 2.71 (t, J=6.7 Hz, 2H), 2.68-2.64 (m, 4H), 2.57 (t, J=6.2 Hz, 2H), 1.96 (p, J=7.1, 6.2 Hz, 4H); $^{13}$C NMR (150 MHz, CDCl$_3$) (major rotamer) δ 174.7 (C), 173.5 (C), 170.7 (C), 167.1 (C), 167. (C), 154.5 (C), 154.3 (C), 136.9 (C), 136.8 (C), 131.8

Figure 23:
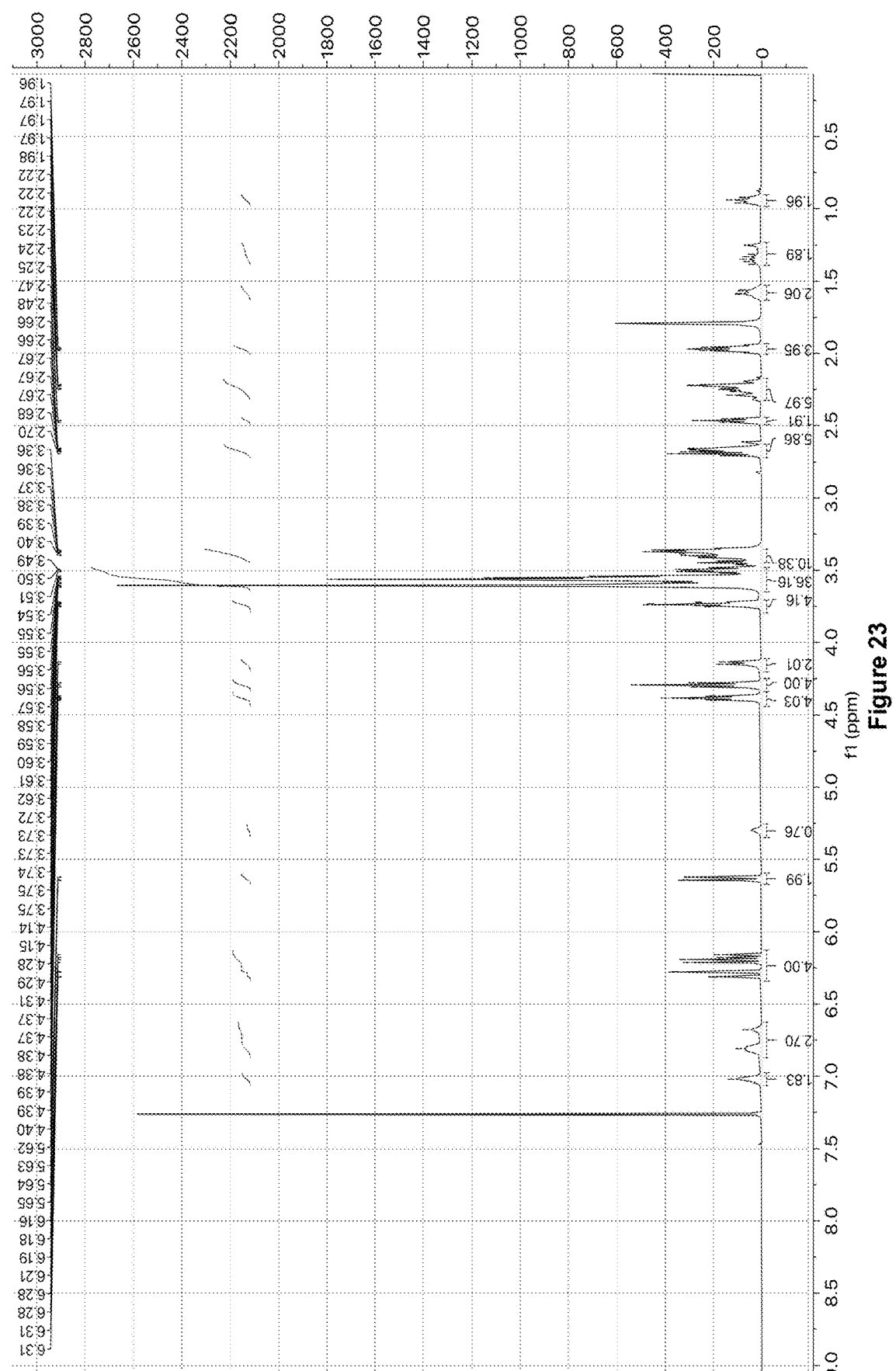
Figure 24:
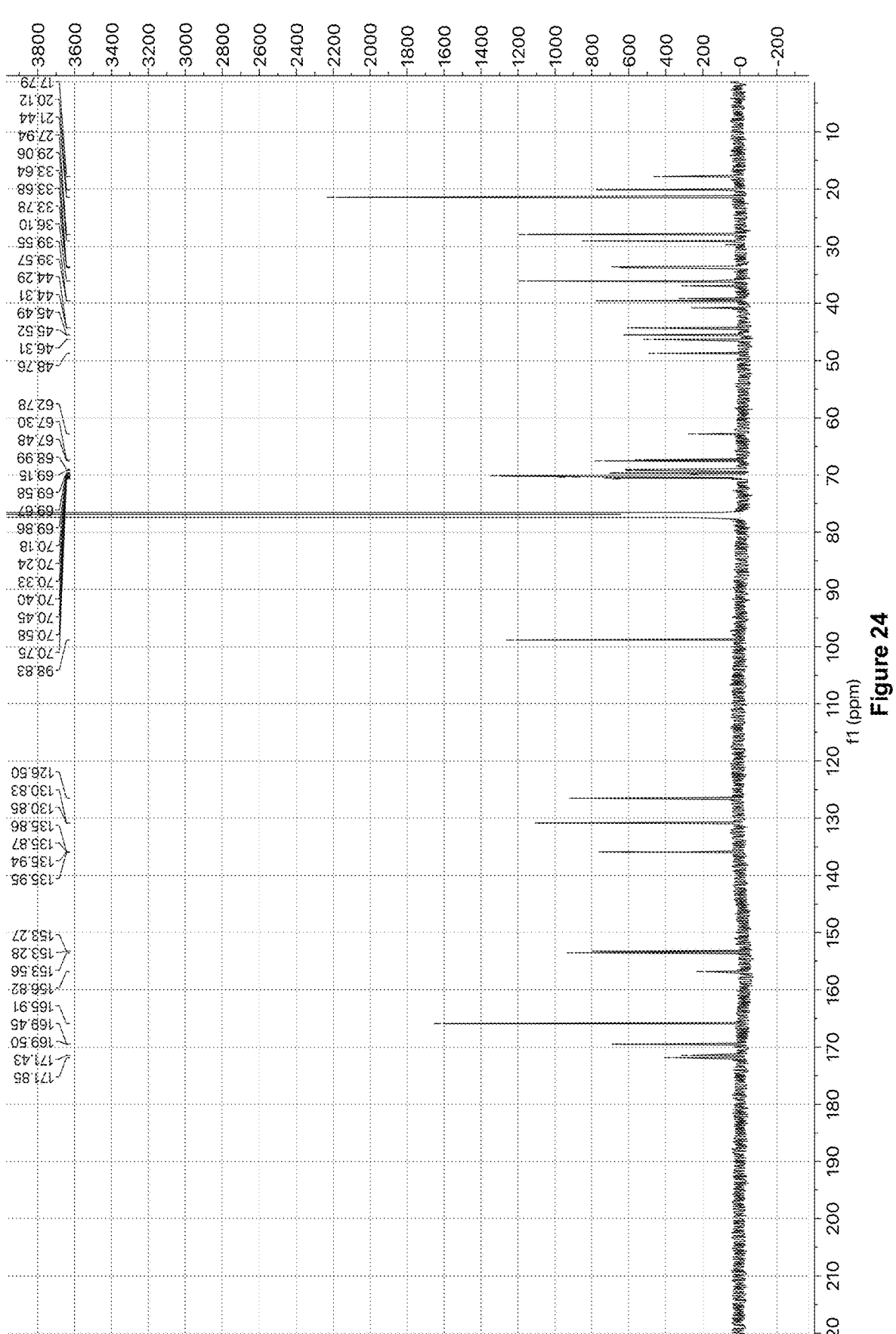

To a solution of bis-PD 6 (15 mg, 0.01 mmol) in DCM (3 mL) was added DCC (2.7 mg, 0.01 mmol) and stirred for 30 min at 0° C. After this time N-hydroxysuccinimide (1.5 mg, 0.01 mmol) was added to the reaction mixture, which was then allowed to warm to 21° C. and stirred for 16 h under argon. After this time the reaction mixture was cooled to –18° C. and filtered. To the filtrate was added ((1R,8S,9s)-bicyclo[6.1.0]non-4-yn-9-yl)methyl (2-(2-(2-aminoethoxy)ethoxy)ethyl) carbamate (3.5 mg, 0.01 mmol) and the reaction stirred at 21° C. for 16 h under argon. After this time, the reaction mixture was concentrated in vacuo and the crude residue was then purified by HPLC (0-100% MeOH/H$_2$O on C18) to give bis-PD 1 (12 mg, 7.11 μM, 65%) as yellow gum. $^1$H NMR (500 MHz, CDCl$_3$) δ 7.02 (s, 2H), 6.86-6.77 (m, 2H), 6.68 (s, 1H), 6.34-6.14 (m, 4H), 5.63 (dd, J=10.2, 1.7 Hz, 2H), 5.30 (s, 1H), 4.38 (t, J=7.2 Hz, 4H), 4.29 (t, J=7.1 Hz, 4H), 4.14 (d, J=7.8 Hz, 2H), 3.77-3.71 (m, 4H), 3.63-3.48 (m, 36H), 3.46-3.33 (m, 10H), 2.73-2.62 (m, 6H), 2.47 (t, J=6.0 Hz, 2H), 2.34-2.17 (m, 6H), 1.97 (t, J=7.1, 6.3 Hz, 4H), 1.64-1.54 (m, 3H), 1.39-1.23 (m, 2H), 0.94 (t, J=9.7 Hz, 2H); $^{13}$C NMR (major rotamer) (125 MHz, CDCl$_3$) δ 171.9 (C), 171.4 (C), 169.5 (C), 165.9 (C), 156.8 (C), 153.6 (C), 153.3 (C), 136.0 (C), 135.9 (C), 130.8 (CH), 126.5 (CH2), 98.8 (C), 70.8 (CH2), 70.6 (CH2), 70.5 (CH2), 70.4 (CH2), 70.3 (CH2), 70.2 (CH2), 70.2 (CH2), 69.7 (CH2), 69.6 (CH2), 69.2 (CH2), 69.0 (CH2), 67.5 (CH2), 67.3 (CH2), 62.7 (CH2), 48.8 (CH2), 46.3 (CH2), 45.5 (CH2), 44.3 (CH2), 40.8 (CH2), 39.6 (CH2), 39.2 (CH2), 37.0 (CH2), 36.1 (CH2), 33.8 (CH2), 33.7 (CH2), 29.1 (CH2), 27.9 (CH2), 21.44 (CH2), 20.1 (CH), 17.8 (CH); IR (thin film) 3296, 3085, 2870, 1635, 1546, 1442 cm$^{-1}$; LRMS (ES–) 1732.25 (100, [M$^{80}$Br$^{80}$Br$^{79}$B$^{79}$Br+ HCOO]$^-$); HRMS (ES+) calcd. for C$_{65}$H$_{98}$Br$_4$N$_{11}$O$_{21}$$^+$ [M$^{80}$Br$^{80}$Br$^{79}$B$^{79}$Br+H]$^+$ 1688.3626, observed 1688.5122. Spectra shown in FIGS. 23 and 24.

6.39-6.11 (m, 2H), 5.64 (dd, J=10.2, 1.6 Hz, 1H), 5.21 (br. s, 1H), 4.38 (t, J=6.9 Hz, 2H), 4.29 (t, J=6.9 Hz, 2H), 4.14 (d, J=8.1 Hz, 2H), 3.69-3.31 (m, 16H), 2.63 (t, J=6.9 Hz, 2H), 2.40-2.17 (m, 4H), 1.97 (t, J=6.3 Hz, 2H), 1.64-1.54 (m, 2H), 1.44-1.24 (m, 1H), 1.02-0.91 (m, 2H); $^{13}$C NMR (125 MHz, CDCl$_3$) δ 171.4 (C), 169.1 (C), 165.9 (C), 153.6 (C), 153.3 (C), 136.0 (C), 135.9 (C), 130.8 (CH), 126.6 (CH$_2$), 98.8 (C), 70.4 (CH$_2$), 70.2 (CH$_2$), 69.5 (CH$_2$), 63.7 (CH$_2$), 62.9 (CH$_2$), 45.5 (CH$_2$), 44.3 (CH$_2$), 40.7 (CH$_2$), 39.5 (CH$_2$), 36.0 (CH$_2$), 33.9 (CH$_2$), 29.1 (CH$_2$), 28.0 (CH$_2$), 21.5 (CH$_2$), 20.1 (CH), 17.8 (CH).

Figure 25:
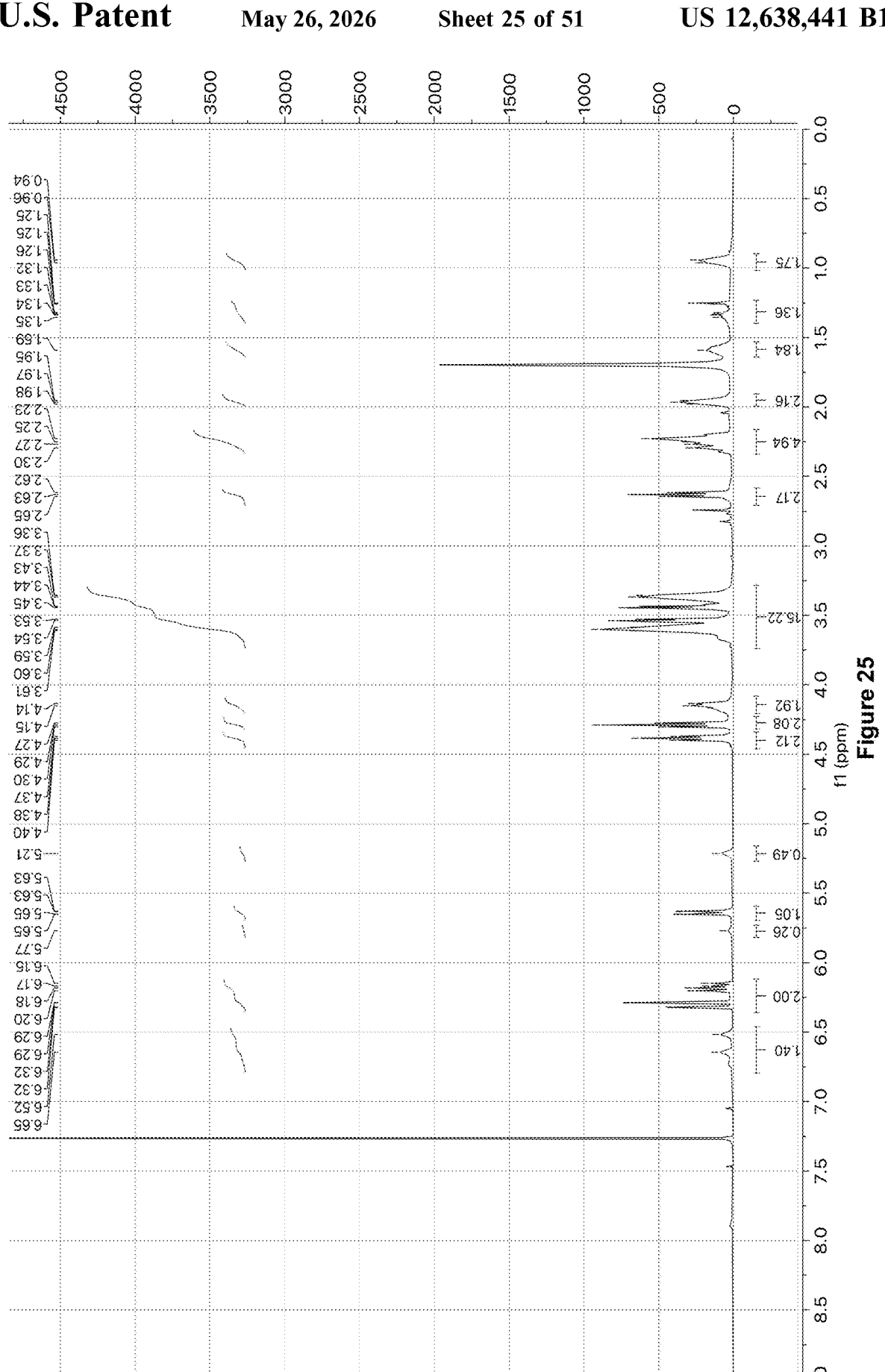
Figure 26:
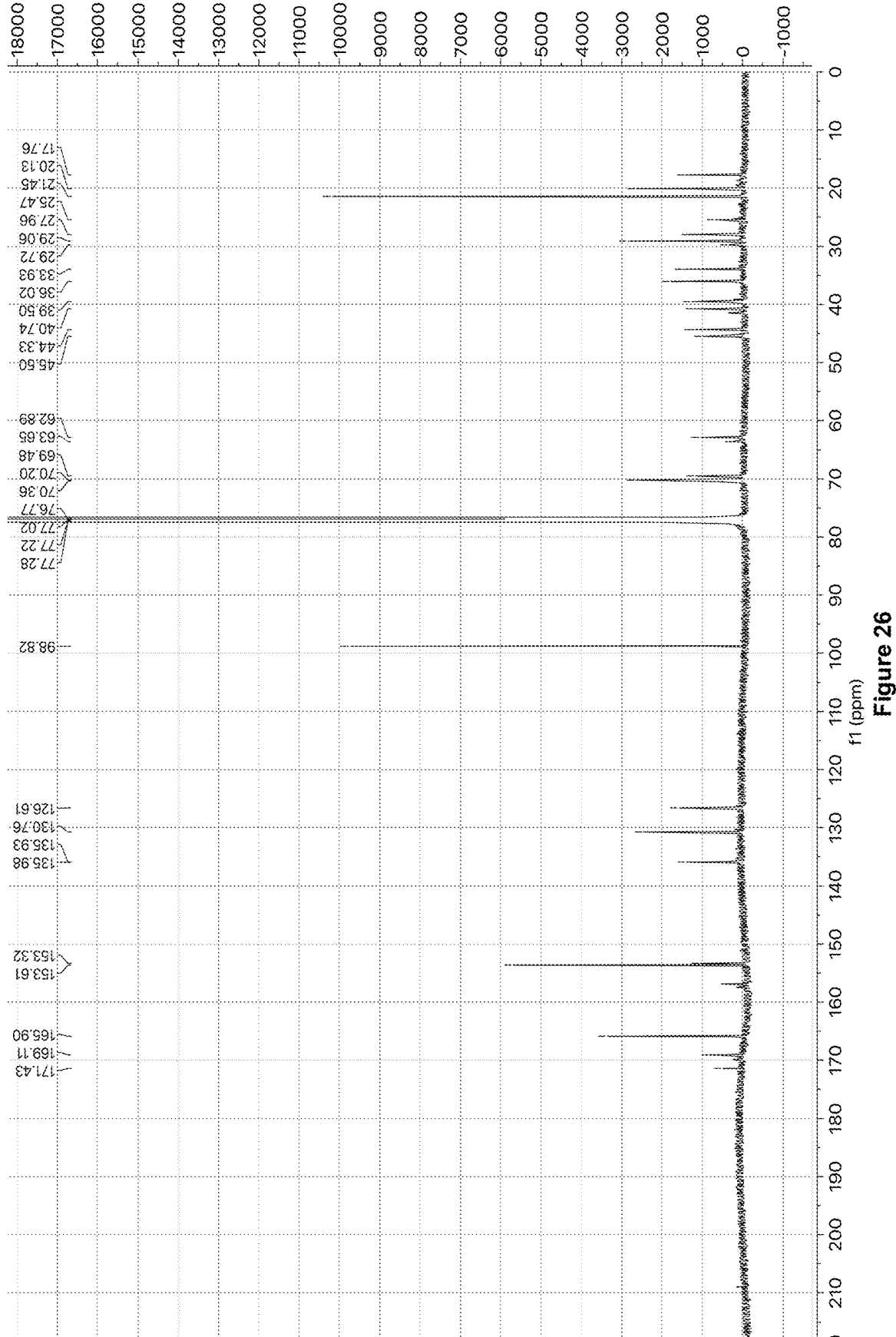

IR (thin film) 3304, 2923, 2195, 1702, 1630, 1542 cm$^{-1}$; LRMS (ES+) 760.41 (100, [M$^{80}$Br$^{79}$Br+H]$^+$); HRMS (ES+) calcd. for C$_{30}$H$_{41}$O$_8$N$_5$Br$_2$Na [M$^{79}$Br$^{79}$Br+H]$^+$ 780.1214, observed 780.1204. Spectra shown in FIGS. 25 and 26.

Figure 27:
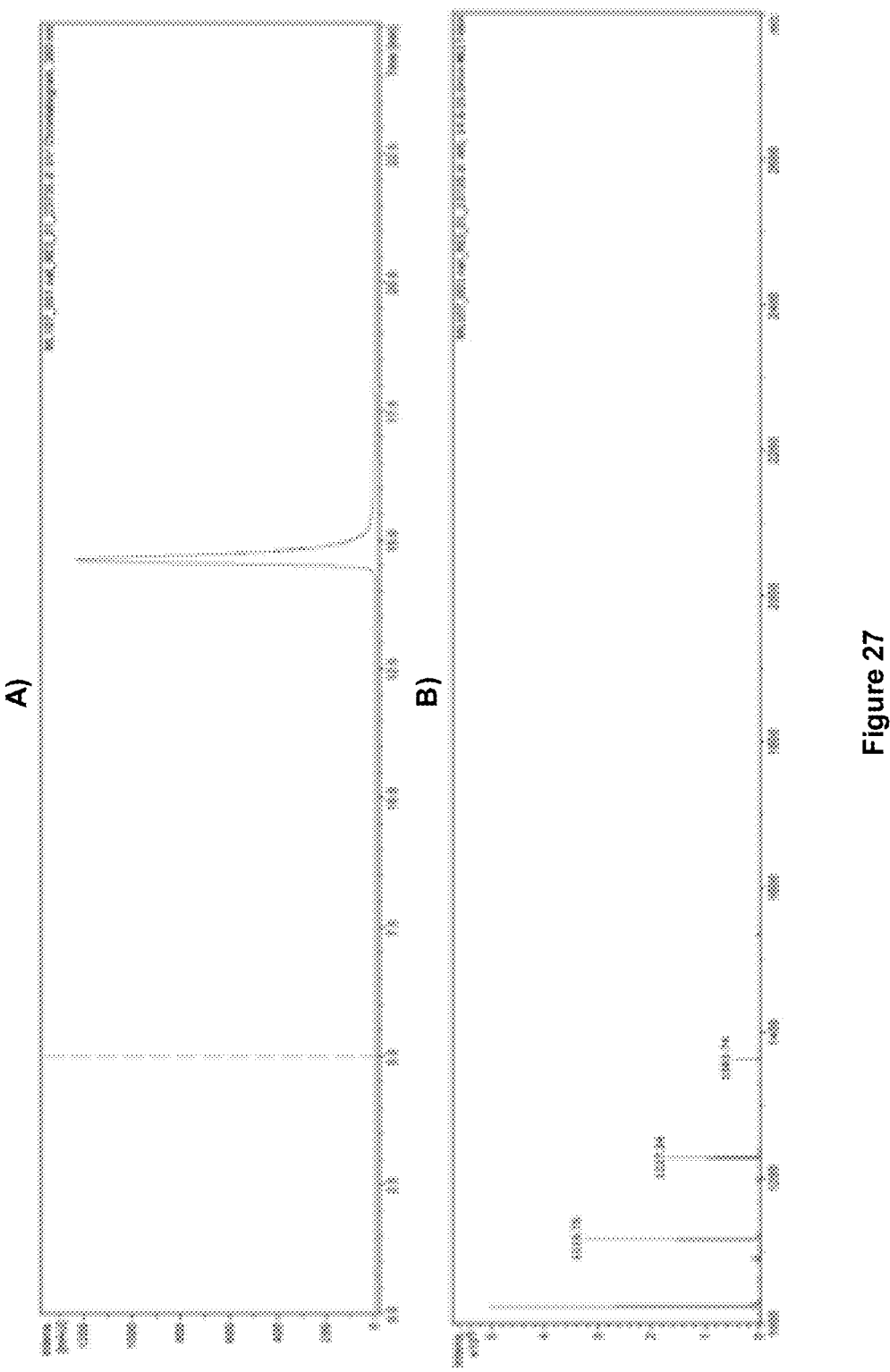
FIG. 27 shows LC-MS chromatogram and spectrum for unmodified oligo-azide and bis-PD 1 modified ON (sequence 1). A) Chromatogram of unmodified oligo-azide; B) Raw MS of unmodified oligo-azide; C) Chromatogram of bis-PD 1 modified ON (sequence 1); D) Raw MS of bis-PD 1 modified ON (sequence 1).
Figure 27:
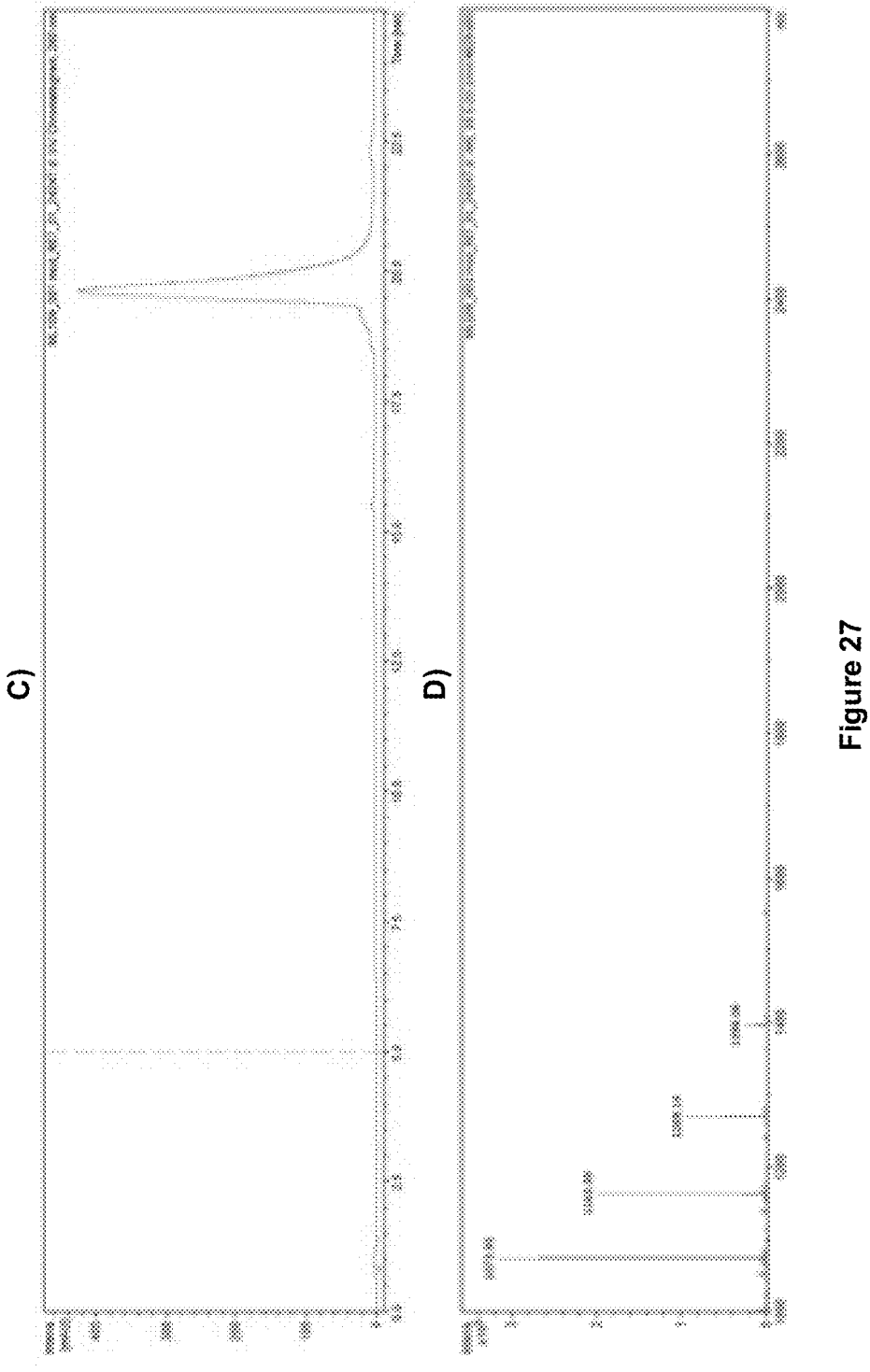
Figure 28:
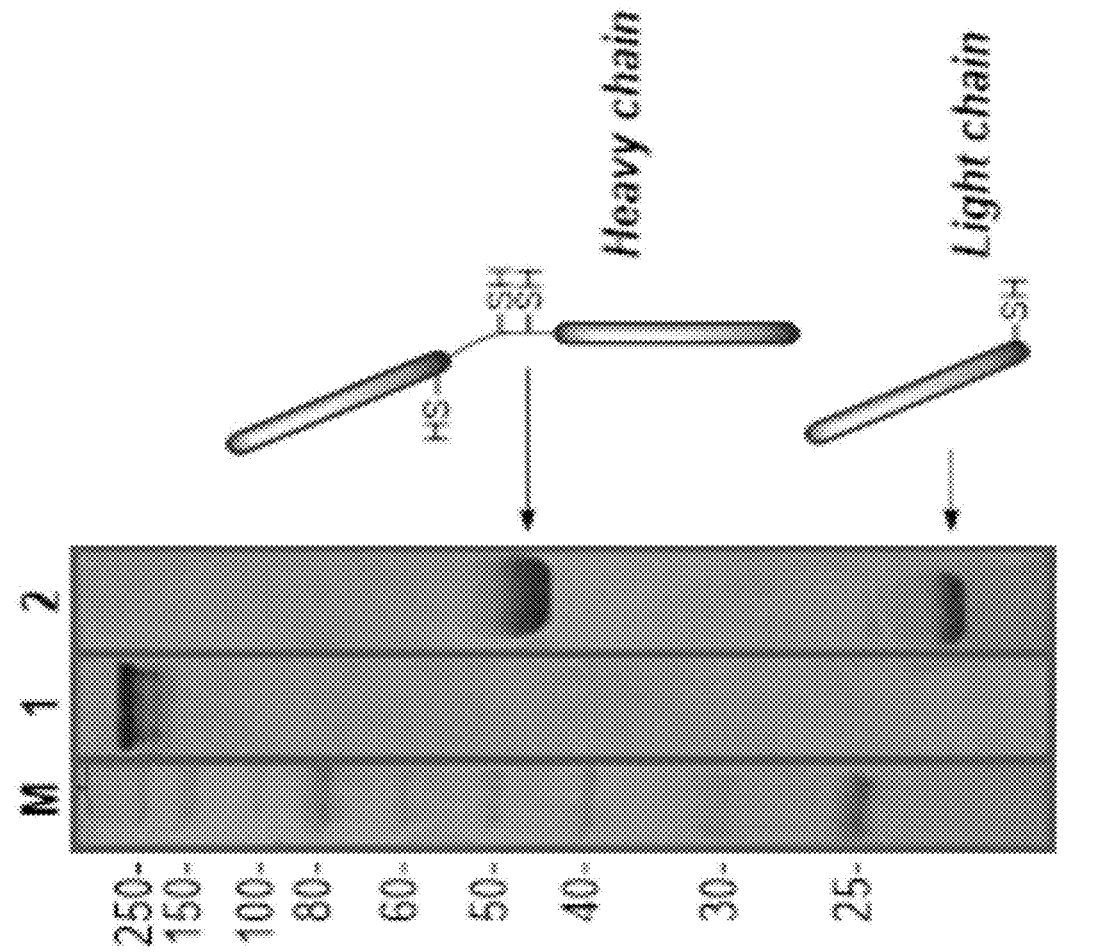
FIG. 28 shows SDS-PAGE of trastuzumab having undergone TCEP reduction. All re-bridged samples are subjected to reduction control, if no further fragmentation of samples is observed following incubation with TCEP, it can be inferred that the sample's disulfide bonds are saturated by re-bridging molecules. M) MW marker; 1) Unmodified trastuzumab; 2) Trastuzumab modified with TCEP only.
Figure 29:
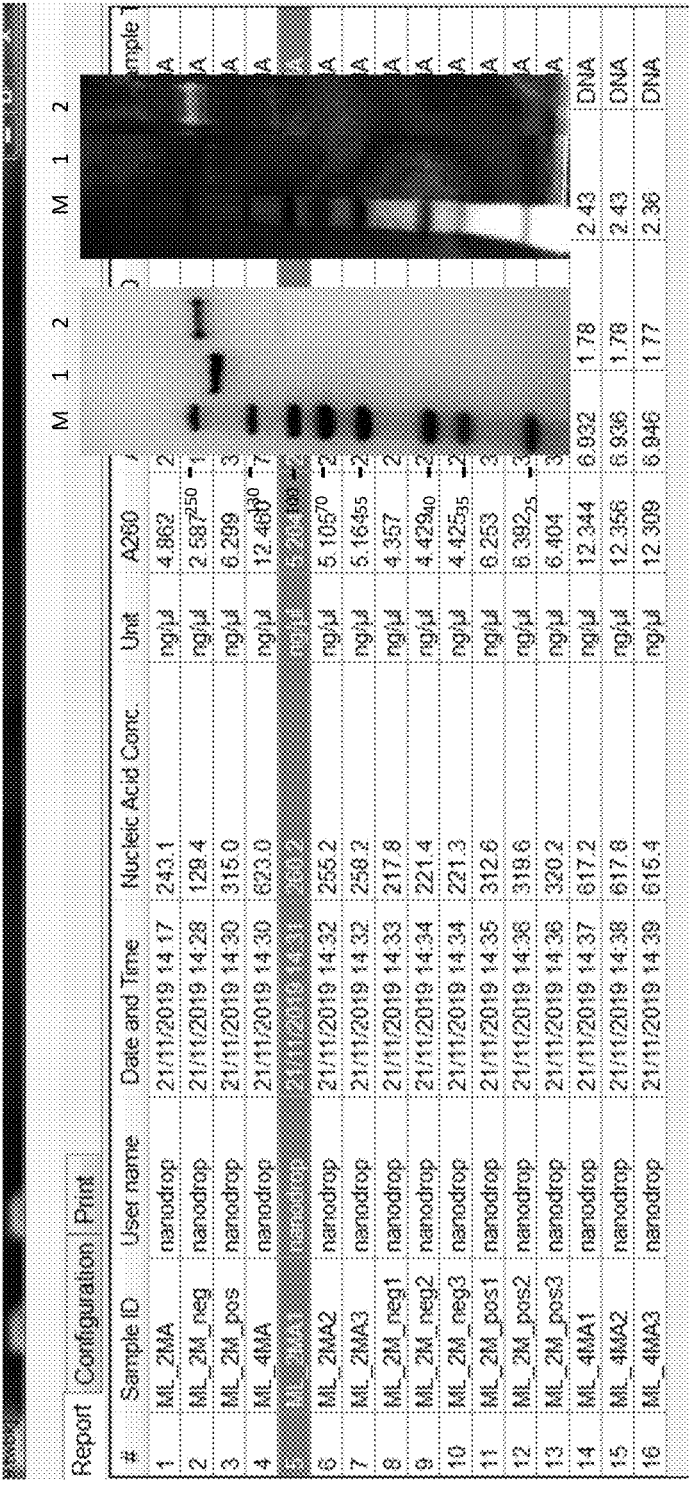
FIGS. 29 and 30: Trastuzumab (anti-HER2) with bis-PD 1 and ON sequence 1.
Figure 29:
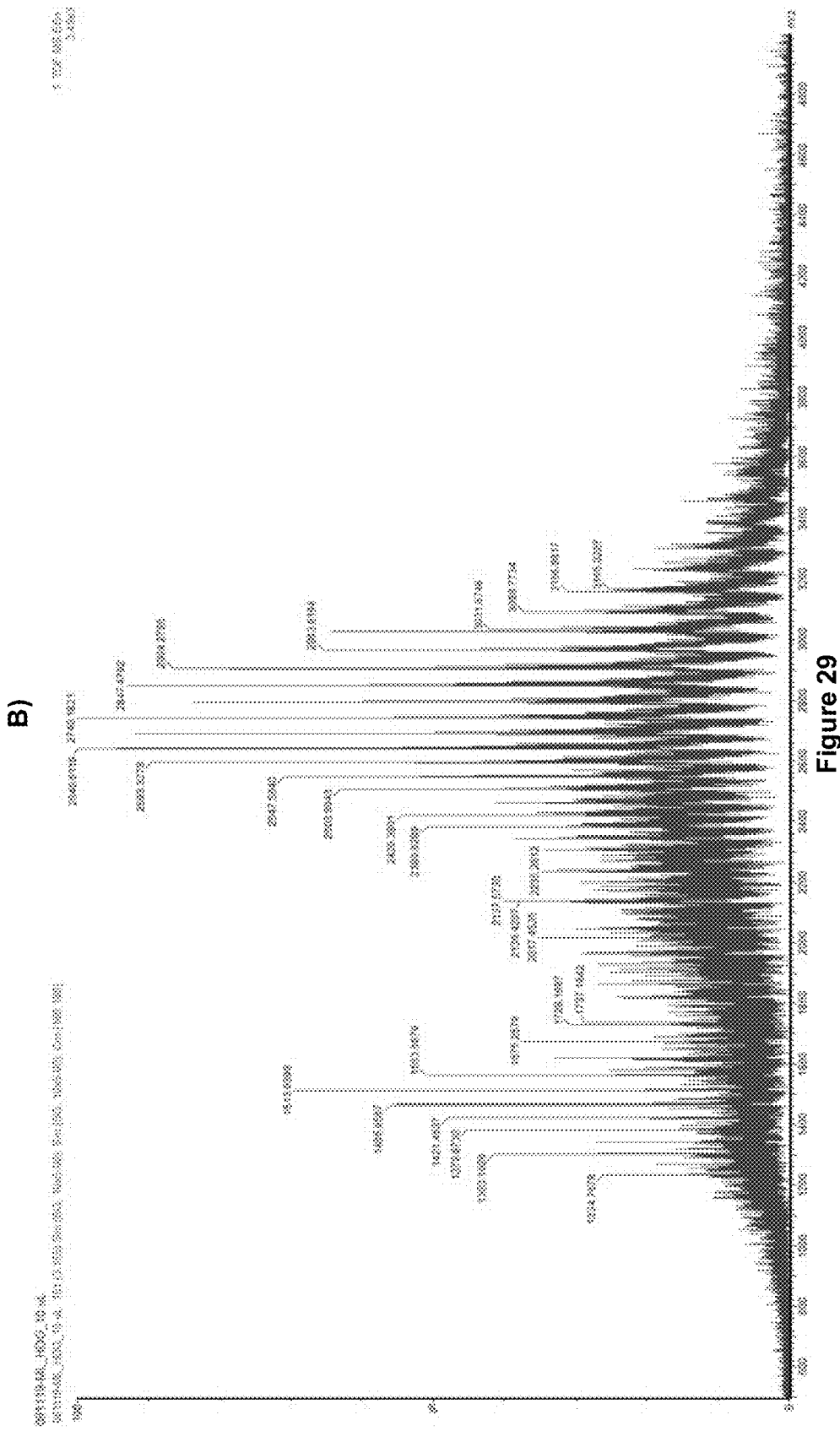
Figure 30:
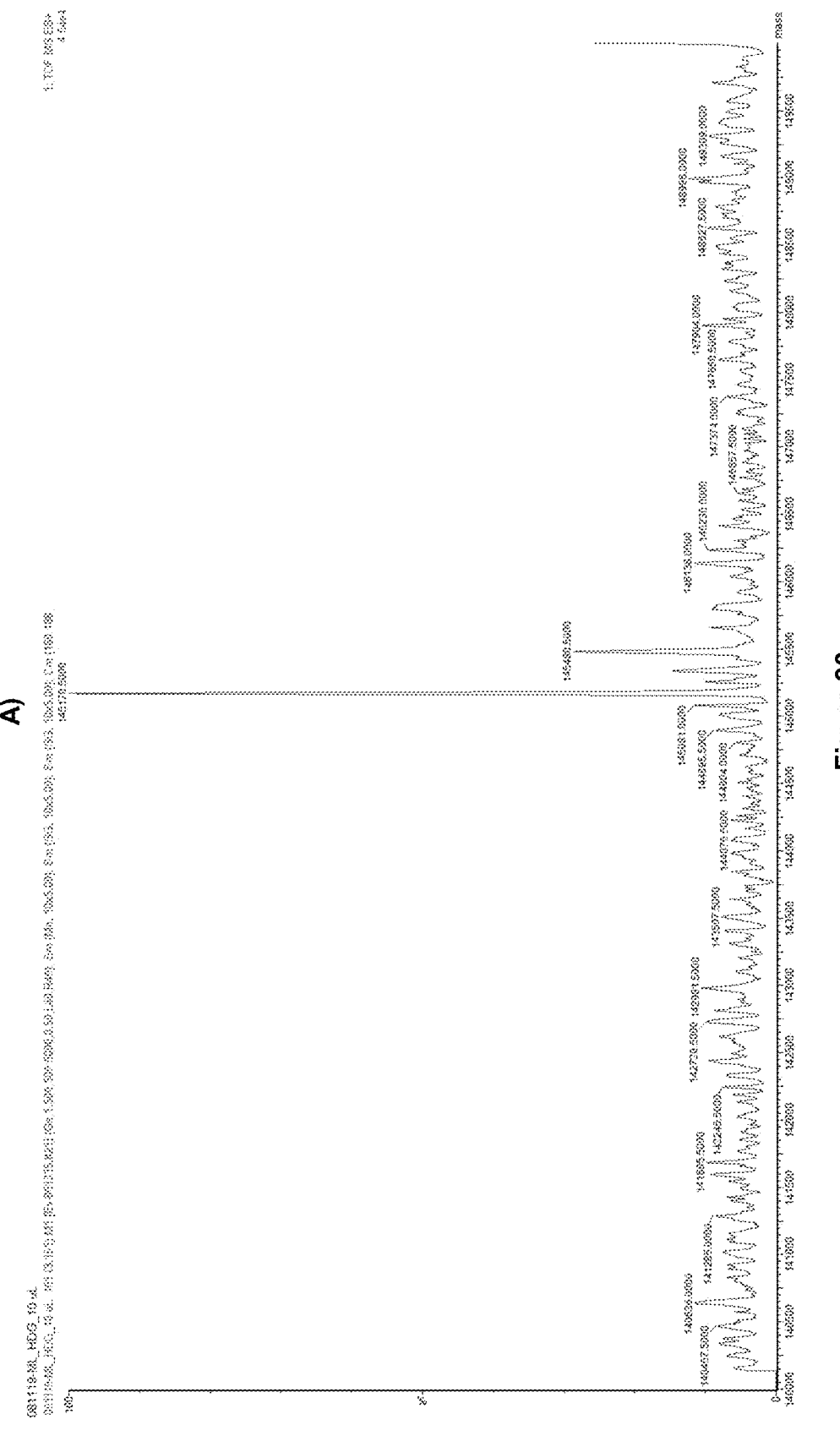
Figure 30:
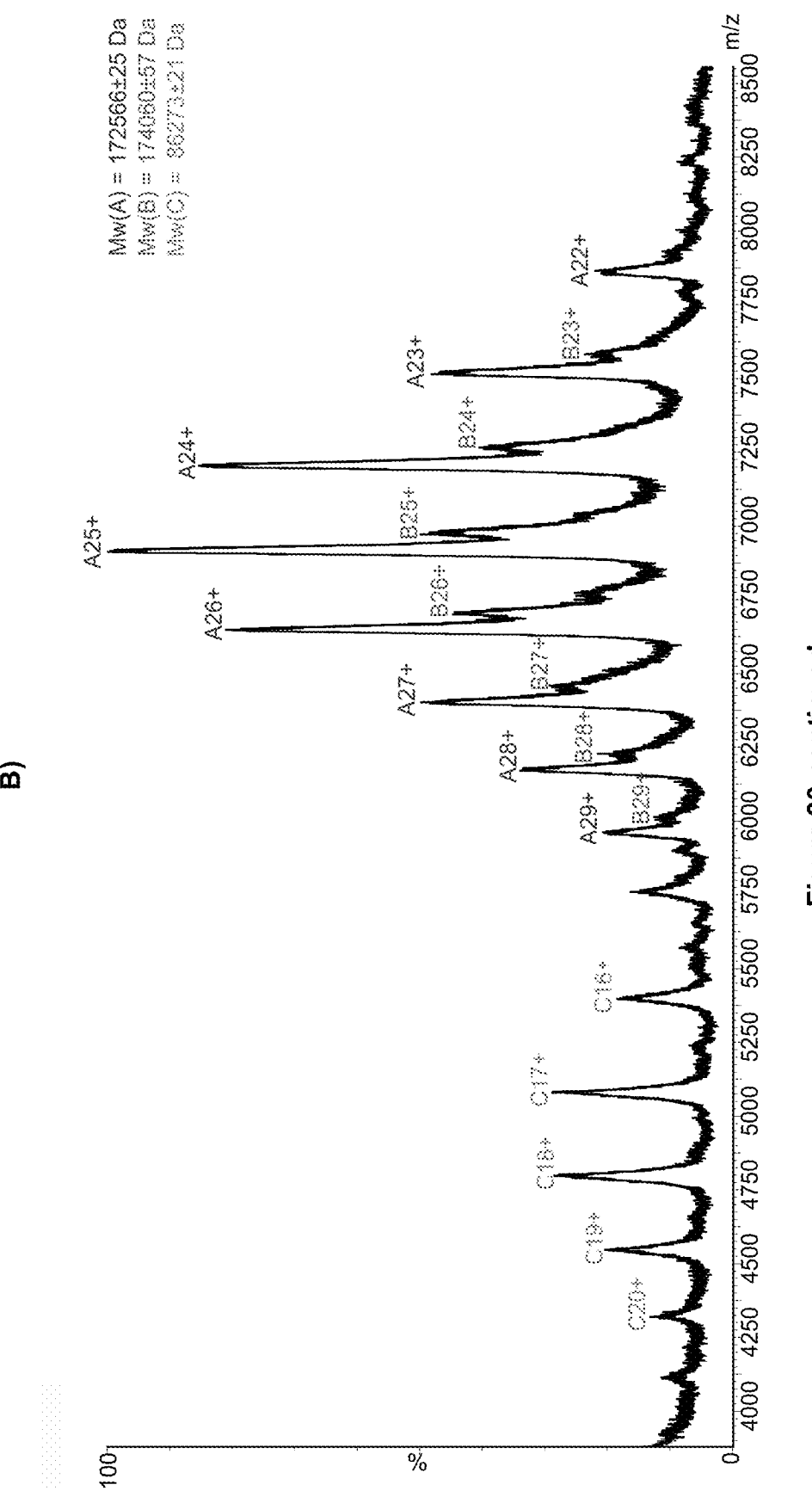
Figure 32:
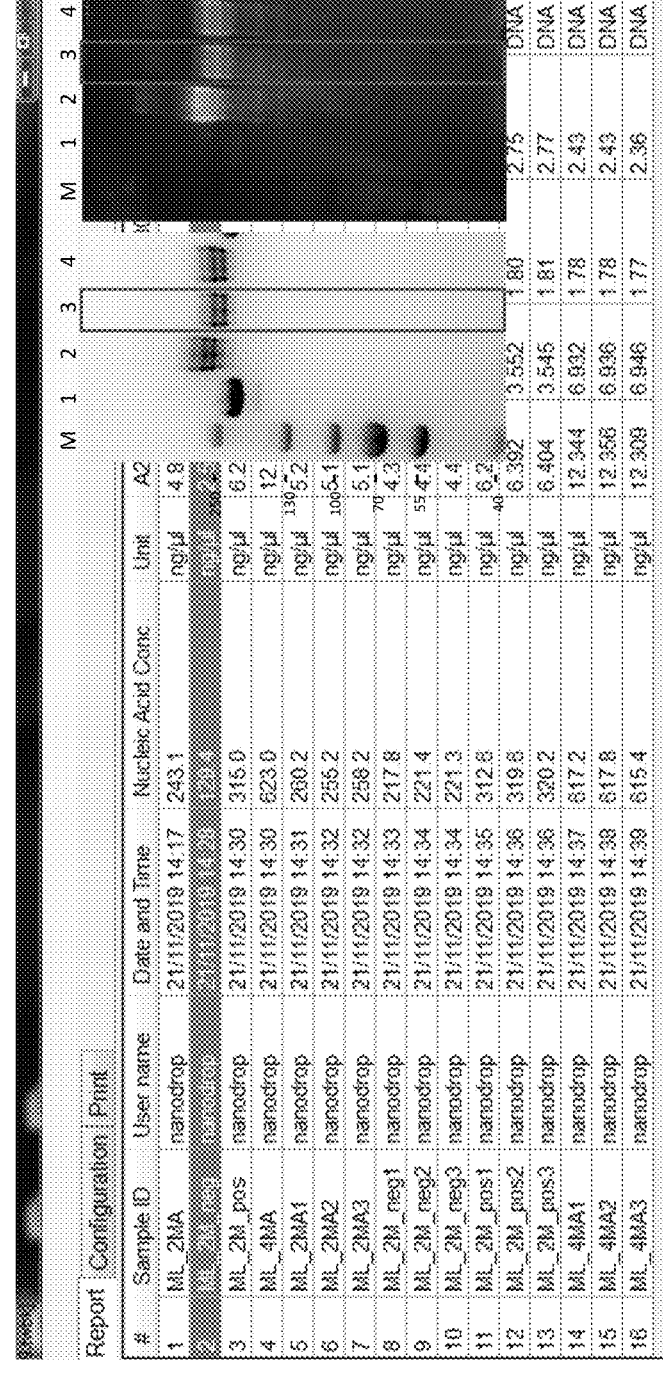
FIG. 32 shows A) UV-vis trace of trastuzumab with lysine modification showing an OAR of 2.5 (inset) SDS-PAGE of M) molecular weight marker; 1) unmodified trastuzumab; 2) trastuzumab with lysine modification OAR 2.5; 3) trastuzumab with lysine modification OAR 1.7; 4) trastuzumab with lysine modification OAR 1.8, shown stained with Coomassie blue (left) and GelRed (Right). B) UV-vis trace of trastuzumab with lysine modification showing an OAR of 1.7. C) UV-vis trace of trastuzumab with lysine modification showing an OAR of 1.8.
Figure 32:
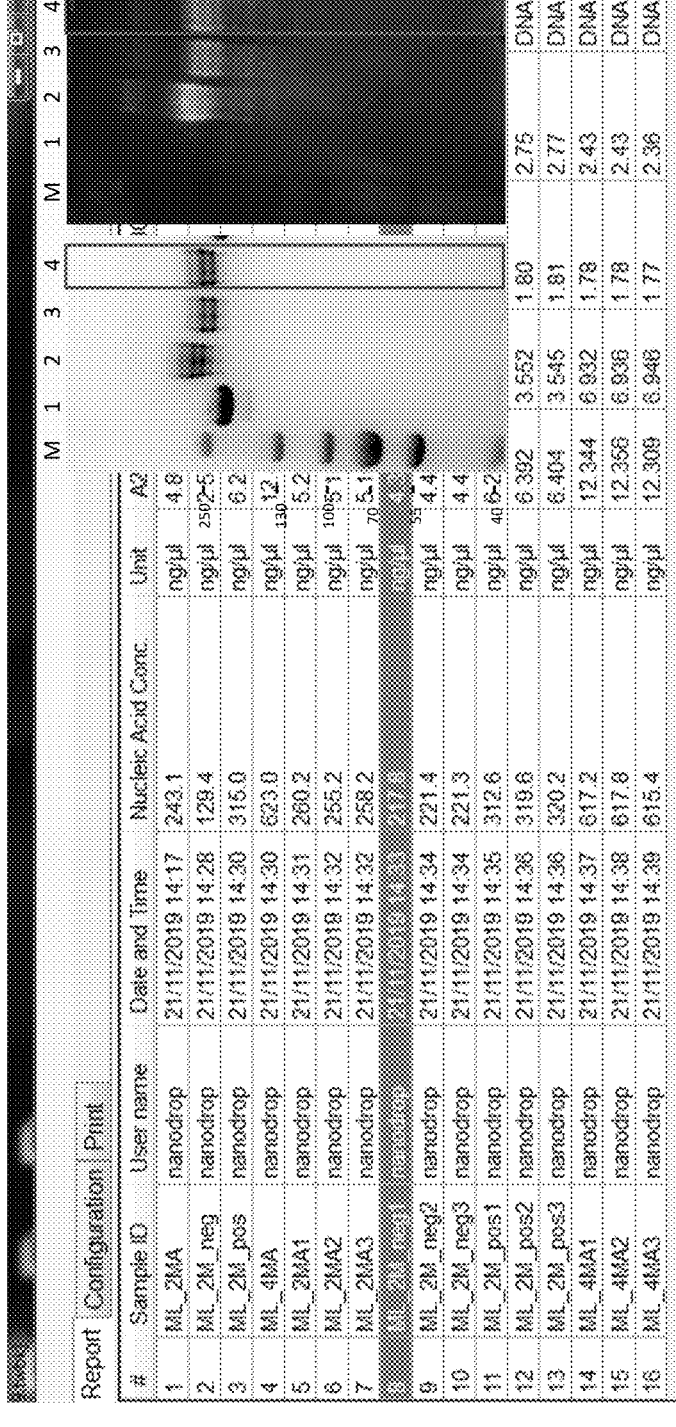
Figure 33:
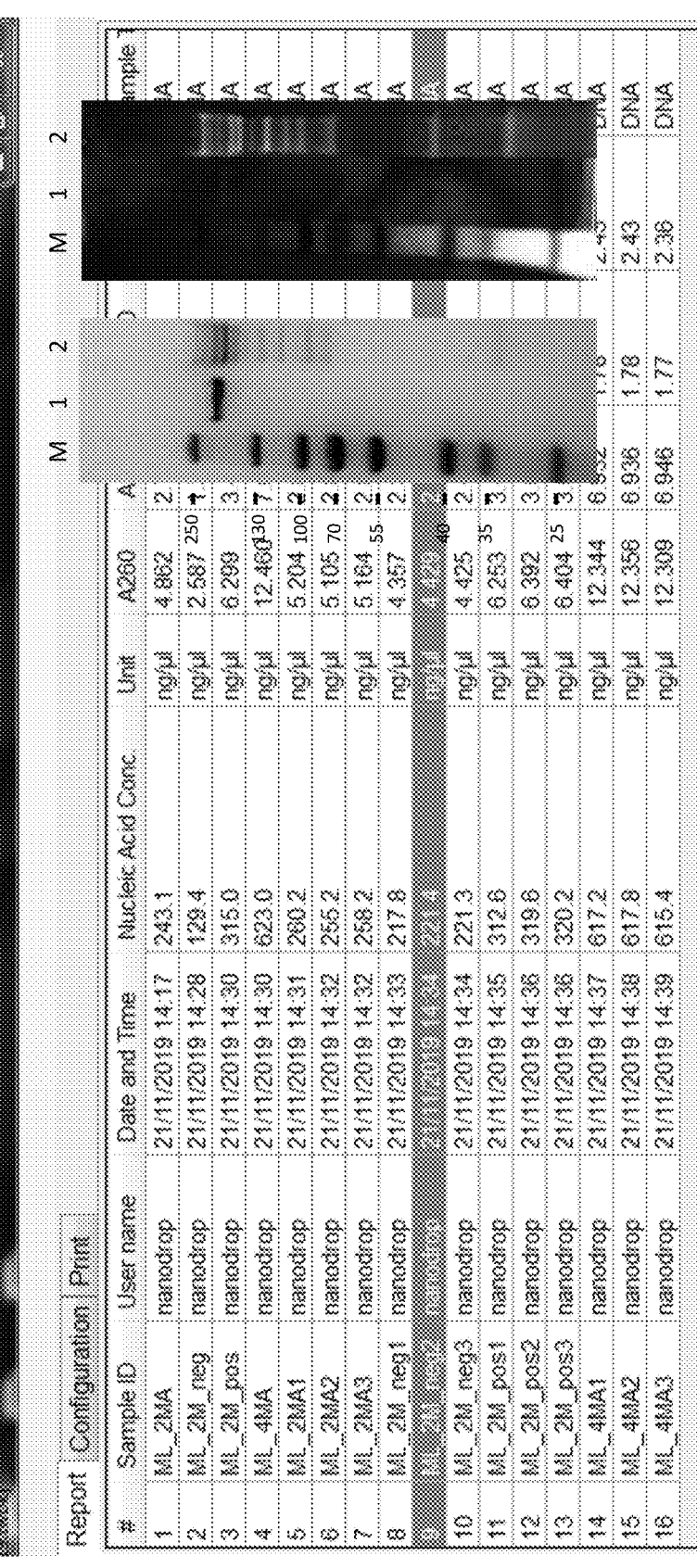
FIG. 33 shows A) UV-vis trace of trastuzumab with cysteine capping showing an OAR of 1.9 (inset) SDS-PAGE of M) molecular weight marker; 1) unmodified trastuzumab; 2) trastuzumab with cysteine capping OAR 1.9; shown stained with Coomassie blue (left) and GelRed (right).
Figure 34:
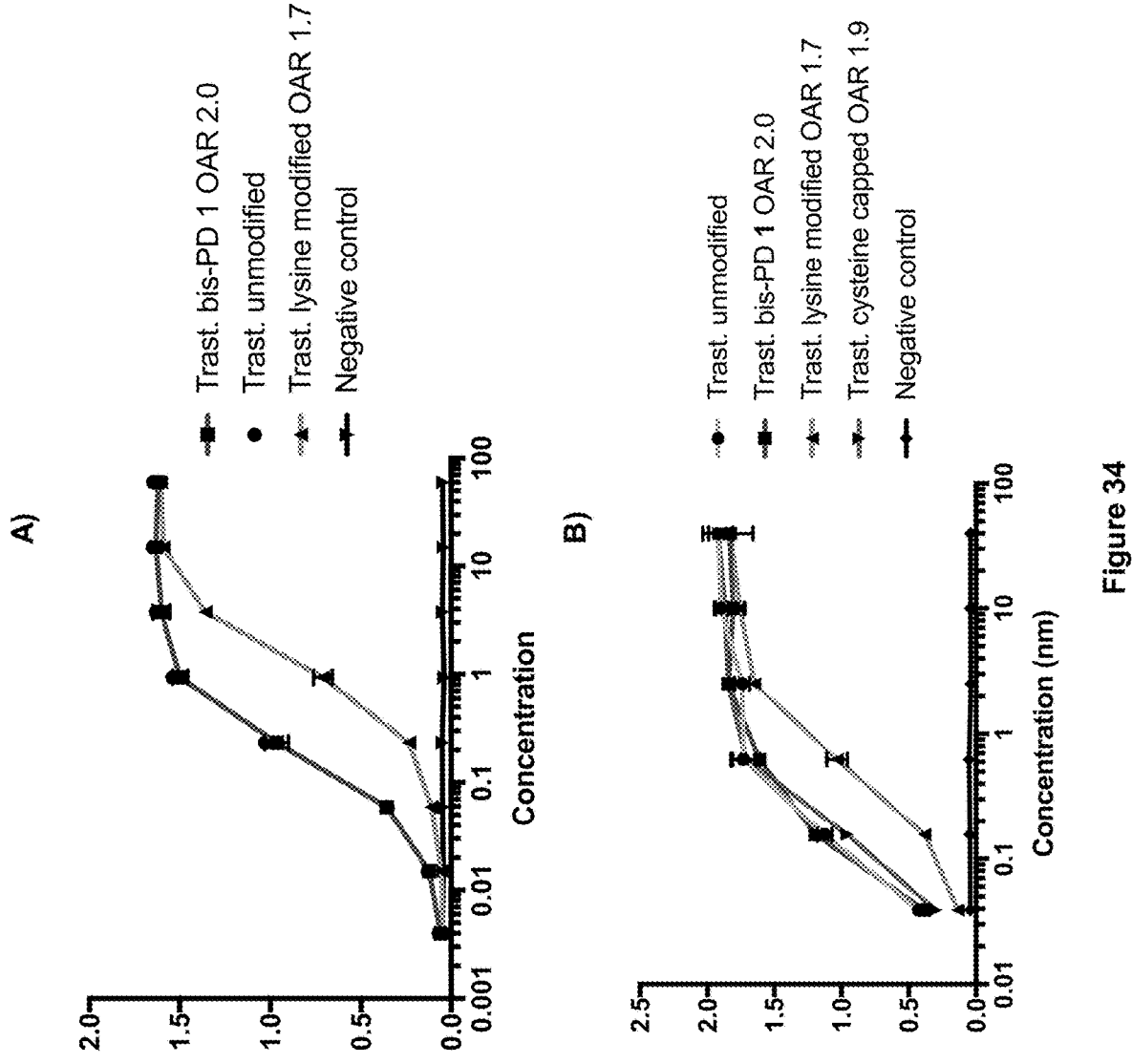
FIG. 34 shows: A) ELISA of trastuzumab modified with bis-PD 1 OAR 2.0 against unmodified trastuzumab and an OAR 1.7 AOC of trastuzumab made via lysine modification. B) ELISA of trastuzumab modified with bis-PD 1 OAR 2.0

Synthesis of ((1R,8S,9s)-bicyclo[6.1.0]non-4-yn-9-yl)methyl (2-(2-(2-(3-(2-(3-acrylamidopropyl)-4,5-dibromo-3,6-dioxo-3,6-dihydropyridazin-1(2H)-yl)propanamido)ethoxy)ethoxy)ethyl)carbamate To a solution of 3-(2-(3-acrylamidopropyl)-4,5-dibromo-3,6-dioxo-3,6-dihydropyridazin-1(2H)-yl)propanoic acid (100 mg, 0.22 mmol) in THF (5 mL) was added DCC (50 mg, 0.24 mmol), and the reaction mixture was stirred for 30 mins at 0° C. After this time, N-hydroxysuccinimide (27 mg, 0.24 mmol) was added to the reaction mixture, which was then allowed to warm to 21° C. and stirred for 16 h. After this time, the reaction mixture was filtered and the filtrate was concentrated in vacuo. The crude residue was then purified by flash column chromatography (20-100% EtOAc/petrol) to give 2,5-dioxopyrrolidin-1-yl 3-(2-(3-acrylamidopropyl)-4,5-dibromo-3,6-dioxo-3,6-dihydropyridazin-1(2H)-yl)propanoate (PD-NHS 2) (90 mg, 0.17 mmol, 75%) as a yellow gum: LRMS (ES+) 551.19 (100, [M$^{79}$Br$^{79}$Br$^{80}$Br $^{80}$Br+H]$^+$). To a solution of PD-NHS 2 (5.0 mg, 0.01 mmol) in MeCN (3 mL), was added ((1R,8S,9s)-bicyclo[6.1.0]non-4-yn-9-yl)methyl (2-(2-(2-aminoethoxy)ethoxy)ethyl) carbamate (2.9 mg, 0.01 mmol) and the reaction stirred for 16 h at 21° C. After this time the reaction mixture was concentrated in vacuo and the residue dissolved in CHCl$_3$ (10 mL). The organic phase was washed with H$_2$O (2×5 mL) and K$_2$CO$_3$ aq. (1×5 mL), dried (MgSO$_4$), and concentrated in vacuo. The crude residue was then purified by flash column chromatography (0-10% MeOH/EtOAc) to give ((1R,8S,9s)-bicyclo[6.1.0]non-4-yn-9-yl)methyl (2-(2-(2-(3-(2-(3-acrylamidopropyl)-4,5-dibromo-3,6-dioxo-3,6-dihydropyridazin-1 (2H)-yl)propanamido)ethoxy)ethoxy) ethyl)carbamate (4.9 mg, 0.06 mmol, 71%) as an amorphous yellow solid. $^1$H NMR (500 MHz, CDCl$_3$) θ 6.82 (br. s, 2H), Conjugation and Analysis of Biomolecules General Procedure for Synthesis of Oligo-PD Conjugates Bis-PD 1 (6.2 µL, 10 mM in DMSO, 3 eq.) was added to a solution of oligo-azide (125 µL, 2.0 mg/mL, 166 M) in H$_2$O (milli-Q™) and incubated for 4 h at 37° C. Excess reagents were removed through buffer exchange with a Zeba-Spin™ (Fisher, MWCO 7,000 Da) into fresh H$_2$O. Samples were then analysed by LCMS to assess conversion and overall yield was determined via UV-vis spectroscopy. For long term storage, samples were lyophilised and stored at −20° C. LCMS data shown in FIG. 27.

ON sequences used for exemplar mAbs (trastuzumab, SMA and E-Cad) were:

ON sequence 1 (used on Trastuzumab and SMA mAbs):
TTTTTGATCCGATTGGAACCGTCC-CAAGCGTTGCGCTAG (SEQ ID NO: 1)

ON sequence 2 (used on E-Cad mAb):
TTTTTGCTATCGTTCGTTCGAGGCCAGAGCAT-TCGCTAG (SEQ ID NO: 2)

General Procedure for Synthesis of Bis-PD 1-Re-Bridged AOCs (100 µg mAb Scale)

TCEP.HCl (2.0 µL, 10 mM, 30 eq.) in BBS (25 mM sodium borate, 25 mM NaCl, 0.5 mM EDTA, pH 8.0) was added to a solution of mAb (65 µL, 1.5 mg/mL, 10 µM) in BBS which had been pre-treated with oligo-bis-PD 1 (4.0 µL, 400 UM in BBS, 2.5 eq.) and stored at 4° C. for 10 min previously. The reaction mixture was then stored at 4° C. for 8 h. Excess reagents were removed by buffer exchange with a P-30 mini-BioSpin™ (Bio-Rad, MWCO 30,000 Da). The samples were analysed by SDS-PAGE gel and UV-Vis spectroscopy and, in the case of Trastuzumab, mass spectrometry, to determine an OAR.

Analysis of AOCs

SDS-PAGE analysis was conducted by running samples on Bio-Rad 4-12% GTX mini-Protean acrylamide gels, side by side with both a molecular weight ladder (PageRuler Plus™, Fisher), and an equivalent conjugate with a distribution of oligo loadings to serve as an OAR 'ladder'. Congruent migration of the AOC product with the corresponding loading in the OAR ladder showed the desired OAR had been achieved. For some commercially available Abs, bands to not resolve well enough to perform this validation, in which case TCEP reduction control (see below) and UV-vis spectroscopy must be relied upon.

A TCEP reduction control was also conducted on conjugates: TCEP.HCl (2 µL, 10 mM in BBS, 30 eq.) was added to the AOC product (70 µL, 1.4 mg/mL, 9.7 UM) in BBS. The reaction mixture was then incubated at 37° C. for 1 h. If there was no fragmentation observed it was concluded that no accessible inter-chain disulfide bonds were remaining in the AOC product, and that the AOC is fully re-bridged (control Trastuzumab reduction below).

For UV-vis spectroscopy; samples were measured at 260 nm using a calculated extinction coefficient specific to the ON used. Absorption for AOCs of a given concentration was measured against a background of a solution of unmodified Ab in the same buffer at the same concentration to compensate for protein absorption.

Trastuzumab-bis-PD 1-ON sequence 1-AOC was analysed by native-MS following deglycosylation with PNGase F Rapid™ (NEB labs). Expected mass: ca. 172,473 Da. Observed mass: $172,566 \pm 25$ Da. A small amount of an adduct at ca. +1,494 Da was observed, likely arising from incomplete deglycosylation of Fc-glycans. Another mass of $86,273 \pm 21$ Da can also be observed corresponding to half mAb (H+L+1ON) arising from non-native re-bridging in the mAb's hinge region; this fragment's intensity is enriched by MS analysis compared with the same sample analysed by SDS-PAGE, due to the smaller fragment being more readily ionised.

Procedure for Synthesis of Lysine Modified Trastuzumab AOC with ON Sequence 1

Propargyl-N-hydroxysuccinimidyl ester (1.5 µL, 2.5 mM in DMSO, 10 eq) was added to a solution of trastuzumab (20 µL, 2.9 mg/mL, 17.1 µM) in PBS (137 mM NaCl, 2.7 mM KCl, 8.0 mM $Na_2HPO_4$, 2.0 mM $K_2HPO_4$, pH 7.4) and incubated for 4 h at 37° C. Excess reagents were removed through buffer exchange with a Zeba-Spin™ (Fisher, MWCO 7,000 Da) into fresh PBS. To the resultant filtrate was added oligo-azide (3.3 µL, 4.9 mg/ml in $H_2O$, 400 M, 4 eq.), $CuSO_4$ (0.8 µL, 5 mM in PBS, 12 eq.), THPTA (0.8 µL, 25 mM in PBS, 50 eq.) and sodium ascorbate (6.7 µL, 100 mM in PBS, to make reaction mixture 20 mM) and the mixture incubated for 4 h at 37° C. After this time Excess reagents were removed through buffer exchange with a Zeba-Spin™ (Fisher, MWCO 7,000 Da) into fresh PBS and the sample analysed by UV-vis spectroscopy and SDS-PAGE. This reaction was repeated several times with OAR in the range of 1.7-2.5.

Procedure for Synthesis of Cysteine-Capped Trastuzumab AOC with ON Sequence 1

Succinimidyl 4-(N-maleimidomethyl)cyclohexane-1-carboxylate (19 µL, 20 mM in DMSO, 10 eq) was added to a solution of oligo-$NH_2$ (95 µL, 4.9 mg/mL, 400 µM) in PBS (137 mM NaCl, 2.7 mM KCl, 8.0 mM $Na_2HPO_4$, 2.0 mM $K_2HPO_4$, pH 7.4) and incubated for 16 h at 21° C. Excess reagents were removed through buffer exchange with a Zeba-Spin™ (Fisher, MWCO 7,000 Da) into fresh BBS (25 mM sodium borate, 25 mM NaCl, 0.5 mM EDTA, pH 8.0). Meanwhile, TCEP.HCl (1 µL, 20 mM in BBS, 60 eq.) was added to a solution of trastuzumab (20 µL, 2.9 mg/mL, 17.1 µM) in BBS and incubated for 2 h at 37° C. After this time, excess reagents were removed through repeated diafiltration using an Amicon™ Ultra-0.5 mL centrifugal filter (MWCO 3,000 Da). To the solution of reduced trastuzumab (30 µL, 1.8 mg/mL, 10.7 µM) in BBS was added the SMCC-modified oligo-$NH_2$ (2.8 µL, 386 µM, 3.4 eq) and the sample analysed by UV-vis spectroscopy and SDS-PAGE. OAR was calculated at 1.9.

General Procedure for ELISA of Trastuzumab AOCs

A CoStar High-bind 96 well plate was coated overnight at 4° C. with HER2 (0.25 µg/mL) in 50 mM sodium carbonate buffer pH=9.6, 100 µl). As a negative control one row was coated with only buffer. The solutions were removed and each well washed (3×PBS, 0.05% Tween). The wells were subsequently coated with a 2% BSA solution in PBS for one hour at room temperature. After this the wells were emptied and washed (4×PBS with 0.05% Tween). Solutions of unmodified trastuzumab and trastuzumab AOCs in Ab buffer (PBS pH 7.4, 0.05% Tween, 2% BSA) were prepared at 60 nM for ELISA 1 and 15 nM for ELISA 2. The dilutions were carried out with a dilution factor of ¼ for 8 points for ELISA 1 and 6 points for ELISA 2. 90 µl of each solution was placed into the wells, each in triplicate, and incubated for two hours at 21° C. As negative controls sodium carbonate buffer only and the antibodies at 60 nM in the absence of HER2 were also subjected to the same protocol. The solutions were removed and the wells washed (3×PBS, 0.05% Tween). Detection antibody (100 µL of anti-human IgG, Fab-specific-peroxidase solution, diluted 1:10,000 in Ab buffer) was added and left for one hour at 21° C. The solutions were removed and the wells washed (6×PBS with 0.05% Tween). Finally, a TMB solution (citrate buffer pH 5, 0.004% $H_2O_2$, 0.0096% TMB, 100 µL) was added to each well. After five minutes the reaction was stopped through addition of 0.2 M sulfuric acid (50 µL). Absorbance was measured at 450 nm and corrected by subtracting the average of negative controls. Protocol was adapted from a literature procedure[2].

REFERENCES FOR SYNTHESIS SECTION

1. Campbell, A. S. et al. Polymer-based protein engineering grown ferrocene-containing redox polymers improve current generation in an enzymatic biofuel cell. *Biosens. Bioelectron.* 86, 446-453 (2016).
2. Lee, M. T. W. et al. Enabling the controlled assembly of antibody conjugates with a loading of two modules without antibody engineering. *Chem. Sci.* 8, 2056-2060 (2017).

Example 2

1: Synthesis of Additional Antibody-[Bis-PD1]—Oligo Conjugates

Protocols:

Antibodies and Reagents

Primary antibody to CD44 (NBP1-41266) was purchased from Novus Biologics, whereas to CD31 (ab225883) was purchased from Abcam. Primary antibody to DNA/RNA G-Quadruplex (ab00174) was purchased from Absolute Antibody and primary antibody to cleaved caspase-3 (D175 SA1E) and Histone 3 (4499BF) were purchased from Cell Signaling Technology. Hoechst 33342 and 4',6-diamidino-2-phenylindole (DAPI), as well as the secondary antibodies conjugated to Alexa Fluor 488 or Alexa Fluor 568 and Alexa Fluor 647, were purchased from Life Technologies.

Functionalised oligonucleotides were purchased from Integrated DNA technologies (IDT)

For immunostaining, sections were allowed to return to room temperature, for 1 h. After this time, sections were heated on a heating block for 30 min at 60° C., washed in dd $H_2O$ for 10 min, at room temperature, before being emerged in HIER buffer (10 mM TRIS, 1 mM EDTA, pH=9.2) and List of antibodies and associated ONs

| Antibody | ONs conjugated to bis-PD | Sequence of ON |
|---|---|---|
| Histone H3 (D1h2) XP(R) | proFISH_read1 (1) | /5AzideN/AGAGGCGGCCAATACAAGCCGG GATGTATTGAAGGAGGATAGAGGCGGCC AATACAAGCC (SEQ ID NO: 3) |
| Cleaved Caspase-3 | proFISH_read3 (3) | /5AzideN/AGAGGCGGCCAATACAAGCCAG AGTGAGTAGTAGTGGAGTAGAGGCGGCC AATACAAGCC (SEQ ID NO: 4) |
| Anti-CD44 | proFISH_read4 (4) | /5AzideN/AGAGGCGGCCAATACAAGCCTG TGATGGAAGTTAGAGGGTAGAGGCGGCC AATACAAGCC (SEQ ID NO: 5) |
| Anti-DNA/RNA G-quadruplex (BG4) | proFISH_read8 (8) | /5AzideN/AGAGGCGGCCAATACAAGCCAG GTTAGGTTGAGAATAGGAAGAGGCGGCC AATACAAGCC (SEQ ID NO: 6) |
| Anti-CD31 | proFISH_read14 (14) | /5AzideN/AGAGGCGGCCAATACAAGCCGA TGATGTAGTAGTAAGGGTAGAGGCGGCC AATACAAGCC (SEQ ID NO: 7 |

General Procedure for Synthesis of Bis-PD Re-Bridged AOCs (100 μg mAb Scale)

TCEP.HCl (2.0-4.0 μL, 10 mM, 30-60 eq.) in BBS (25 mM sodium borate, 25 mM NaCl, 0.5 mM EDTA, pH 8.0) was added to a solution of mAb (65 μL, 1.5 mg/mL, 10 UM) in BBS which had been pre-treated with corresponding oligo-bis-PD (4.0 μL, 400 M in BBS, 2.5 eq.) and stored at 4° C. for 10 min previously. The reaction mixture was then stored at 4° C. for 8-16 h. Excess reagents were removed by buffer exchange with a P-30 mini- BioSpin™ (Bio-Rad, MWCO 30,000 Da). The samples were analysed by SDS-PAGE gel and UV-Vis spectroscopy to determine an Oligo-Antibody ratio.

Results: SDS-Page Gels Showing Antibody Conjugation

SDS-page gels showing antibody conjugation are shown in FIGS. 35 to 40.

2: Validation of Binding Pattern of New Conjugated Antibodies

Protocols

Immunofluorescence Staining on Histological Sections (15 Um) Collected by Serial Two Photon Microscopy.

All animal procedures were conducted in accordance with the UK Animal Scientific Procedures Act (ASPA). Procedures were performed in an authorized establishment (CRUK Cambridge Institute, University of Cambridge) under the authority of Project License PAD85403A, by operators in possession of a personal animal use license and fully trained.

Tumours were generated in immune-compromised mice (NSG strain) by injecting 60,000 cells from the Balb/C triple-negative like tumour cell line (4t1) in the abdominal fat pad. Tumours were collected at 21 days post-injection and fixed in 4% para-formaldehyde in phosphate buffered saline for 24 h at room temperature. Fixed samples were embedded in 4% oxydised agarose and re-embedded in a proprietary monomer solution produced by Tissuevision Inc (Newton, MA, USA), before sectioning and imaging on a Tissuecyte 1000 Serial two-photon tomography system. Sectioning was conducted at 15 micron thickness and stored at 4C.

subsequently heated for 30 min at 95° C. After this time, sections were washed in PBS for 5 min for 3 times and then blocked with blocking buffer (3% BSA, 0.3% Triton X-100 in PBS) for 30 min at room temperature, in a humid chamber. After this time, native/conjugated primary antibody (150 μl, 5 μg/mL, diluted in antibody dilution buffer –3% BSA, 0.3% Triton X-11 in PBS) was added to section slides, which were subsequently covered with a rectangular coverslip and incubated in a humid chamber for 16 h, at 4° C. After this time, slides were washed in PBST (PBS+0.1% Tween 20) for 5 minutes, 3 times, on a rocker. Subsequently, 150 μl of complementary secondary antibody (1:500, diluted in antibody dilution buffer) was added, slides were covered with coverslip and incubated for 2 h at room temperature in a humid chamber. After this time, slides were washed for 5 minutes, 3 times with PBST, and were subsequently counterstained with Hoechst 33342 solution (1:1000 in PBS) for 10 minutes. Finally, slides were washed with PBST on a rocker for 5 minutes and sample was imaged on a Leica DMI4000 microscope equipped with a Lumencor SOLA SE 365 using a 20X objective and DAPI, mCherry and Cy5 filter sets.

Results:

The immunohistochemistry staining comparing native antibodies with oligonucleotide-conjugated antibodies is shown in FIGS. 41 to 45.

3. Full proFISH Staining, 4 Cycles

Protocols

ProFISH Staining

STPT Sections on functionalised coverslips were contained in a 6 cm TC dish and washed in dd $H_2O$ for 10 min, before being heated on a heating block at 60° C. for 30 min. After this, 5 mL of HIER buffer (pre-heated at 95° C.) was added and sections were incubated in an oven (pre-heated at 95° C.) for 30 min. After this time, sections were washed 3 times in PBS for 10 min each on a rocker (set on slow), 5 mL of blocking buffer was added and sections were further incubated for 1 h at room temperature, on a rocker. ON conjugated primary antibodies were diluted to 5 µg/mL in antibody dilution buffer to achieve a total volume of 80 µl, which was then added as a drop to a parafilm sheet. Then, coverslip was flipped upside down (with the tissue section facing the drop) and section incubated into a humid chamber, for 16 h at 4° C. After this time, coverslips were removed from the parafilm bed, moved into a 6 cm TC dish and washed 3 times with PBST, 10 min each, on a rocker. Subsequently, 1 ml of gel slick was added to a large glass slide (one for each section) and spread with a kimwipe, to produce a hydrophobic surface, whilst coverslips were washed in gel buffer (4% Acryl:Bis 19:1, 0.3 M NaCl, 60 mM Tris HCl, in DEPC-treated water) for 5 min, 2 times, on a rocker. Then, a 60 µl drop of gel buffer (+APS 0.5%, TEMED 0.5%) was added to the now siliconized glass plate for 2 min. After this time, the coverslip was removed from the dish and flipped onto the drop of gel and sections were allowed to polymerise for 1 h, in a dark chamber. Once the gel was set, the coverslip was lifted from the glass plate and moved to a new 6 cm TC dish, where 5 mL of digestion buffer (2×SSC, 2% SDS, 0.5% v/v Triton X-100, 1:100 proteinase K) was added and section incubated at 37° C., for 16 h. After this time, sections were re-incubated with freshly prepared digestion buffer at 37° C., for another 24 h. Subsequently, digestion buffer was removed, and sections were washed with 5 mL 2×SSC, 4 times for 30 min each, on a rocker, before leaving another wash in 2×SSC for another 16 h, at 4° C. After this time, coverslips were firstly washed with 2×SSC 3 times for 10 min, then washed with 5 mL hybridisation buffer (2×SSC, 10% ethylene carbonate) for 5 minutes, at room temperature, on a rocker, and posteriorly incubated with readout probes mix (10 nM of first 2 ON probes Atto 565 and Cy5+1:1000 SYTO-16 dye in hybridisation buffer) for 15 min in a dark chamber, on a rocker.

During this time, more readout probes were also prepared for next cycles (without SYTO-16, 10 nM probe concentration, in pairs, Atto 565 and Cy5 probes).

Readout probes are DNA oligonucleotides with a sequence complementary to the oligonucleotides conjugated to each antibody, modified at the 5' end with a fluorescent group (Atto 565 or Cy5) conjugated via a disulphide cleavable linker (obtained from Biomers GmBh, Germany)

ProFISH Imaging

Cyclic imaging was done on a modified Leica Dmi8 microscope equipped with a high-power light engine (Omicron BriXXHub) with lasers lines at 488 nm, 561 nm and 647 nm. A custom fluidic system was used to automate the readout staining cycles used to detect each antibody, based on a Bioptechs FCS2 chamber connected to a Gilson Minipuls 3 pump and to a series of valves (Hamilton MVP) controlled by a custom python script.

Four cycles were performed, with either one or two antibodies being imaged in each by hybridizing their conjugated oligonucleotides with fluorescently conjugated readout probes.

In each fluidic cycle, the sample was incubated with an anti-fade solution including glucose oxidase, catalase, glucose and Trolox (6-hydroxy-2,5,7,8-tetramethylchroman-2-carboxylic acid), and imaged in the GFP, Atto565 and Cy5 channels using the 488 nm, 561 nm and 647 nm laser. Following the imaging cycle, fluorescence was stripped by incubating the sample for 15 minutes with 50 mM TCEP in 2×SSC, and washing twice for 7 minutes with 2×SSC/10% Ethylene Carbonate. The following two antibodies were then visualized by hybridizing the next two readout probes at a concentration of 10 nM in 2×SSC/10% Ethylene carbonate for 15 minutes.

Results:

The results of 4 cycles of proFISH are shown in FIG. 46.

The invention claimed is:

1. A compound of formula I, or a salt thereof:

(I)

wherein:

$Z_1$ and $Z_2$ are each independently selected from hydrogen, (1-6C)alkyl and a group:

$-L_a\text{-}PG_a$ wherein $L_a$ is (2-10C)alkylene and $PG_a$ is a polymerisable group;

with the proviso that at least one of $Z_1$ or $Z_2$ is a group $-L_a\text{-}PG_a$;

$R_1$, $R_2$, $R_3$ and $R_4$ are each independently selected from —Br, —Cl, —I, and a group of formula A:

A wherein $R_5$ is selected from —$CO_2H$, —$CO_2Me$, —$NO_2$ and —CN, or a group of formula B:

—O—$S(O)_2$—$R_6$ wherein $R_6$ is selected from (1-6C)alkyl and phenyl optionally substituted with methyl;

$L_1$ is (1-5C)alkylene or —$[CH_2CH_2O]_{1\text{-}16}$—$[CH_2]_{2\text{-}5}$—;

$Q_1$ is absent or selected from:

(i) —$C(O)NR_a$—;

(ii) —$NR_aC(O)$—;

(iii)

(iv)

(v) —C(O)O—; and (vi) —OC(O)—;

wherein $R_a$ is selected from hydrogen and methyl;

$L_2$ is (1-5C)alkylene;

$P_1$ is a polymeric moiety having the formula:

-[Monomer A]$_a$- wherein a is 1 to 16;

Monomer A is selected from:

(i) —$OCH_2CH_2$—;

(ii)

and (iii)

$P_2$ is a polymeric moiety having the formula:

-[Monomer B]$_b$- wherein b is 2 to 16;

Monomer B is selected from:

(i) —$CH_2CH_2O$—;

(ii)

and (iii)

$L_3$ is absent or (1-5C)alkylene;

$Q_2$ is absent or selected from:

(i) —$C(O)NR_b$—;

(ii) —$NR_bC(O)$—;

(iii)

(iv)

(v) —OC(O)—; and (vi) —C(O)O—;

wherein $R_b$ is selected from hydrogen and methyl;

$L_a$ is (1-5C)alkylene;

$P_3$ is a polymeric moiety having the formula:

-[Monomer C]$_c$— wherein
  c is 1 to 16;
  Monomer C is selected from:
    (i) —CH$_2$CH$_2$O—;

(ii)

O; and

—CH$_2$—CH—

(iii)

C(O)CH$_3$;

—CH$_2$—CH$_2$—N—

L$_5$ is (1-5C)alkylene;
Q$_3$ is absent or selected from:
  (i) —C(O)NR$_c$—;
  (ii) —NR$_c$C(O)—;

(iii)

;

(iv)

;

(v) —C(O)—;
  (vi) —C(O)O—;
  (vii) —OC(O)—; or
  (viii) —O—C(O)NR$_c$—;
  (ix) —NR$_c$C(O)—O—:
  (x) —NR$_c$—;
  (xi) —O—:
  (xii) —NR$_c$C(O)NR$_c$—;
  (xiii) —S—;
  (xiv) —S(O)—;
  (xv) —S(O)$_2$—;
  (xvi) —S(O)$_2$NR$_c$—; and
  (xvii) —NR$_c$S(O)$_2$—;
  wherein R$_c$ is selected from hydrogen and methyl;
P$_4$ is absent or a polymeric moiety having the formula:
  -[Monomer D]$_d$- wherein
  d is 1 to 16;
  Monomer D is selected from:
    (i) —CH$_2$CH$_2$O—;

(ii)

O; and

—CH$_2$—CH—

(iii)

C(O)CH$_3$;

—CH$_2$—CH$_2$—N—

L$_6$ is (1-5C)alkylene;
Q$_4$ is a group of the formula:

-Q$_{4e}$-L$_7$-Q$_{4b}$- wherein Q$_{4a}$ is selected from:
    (i) —C(O)NR$_d$—;
    (ii) —NR$_d$C(O)—;

(iii)

;

(iv)

;

(v) —C(O)—;
    (vi) —C(O)O—;
    (vii) —OC(O)—;
    (viii) —O—C(O)NR$_d$—;
    (ix) —NR$_d$C(O)—O—;
    (x) —NR$_d$—;
    (xi) —O—;
    (xii) —NR$_d$C(O)NR$_d$—;
    (xiii) —S—;
    (xiv) —S(O)—;
    (xv) —S(O)$_2$—;
    (xvi) —S(O)$_2$NR$_d$—; and
    (xvii) —NR$_d$S(O)$_2$—;
    wherein R$_a$ is selected from hydrogen and methyl;
  L$_7$ is absent or (1-5C)alkylene;
    Q$_{4b}$ is absent when L$_7$ is absent or, when L$_7$ is a
      (1-5C)alkylene, Q$_{4b}$ is absent or selected from:
      (i) —C(O)NR$_e$—;
      (ii) —NR$_e$C(O)—;

(iii)

;

(iv)

;

(v) —C(O)—;
      (vi) —C(O)O—;
      (vii) —OC(O)—;
      (viii) —O—C(O)NR$_e$—;
      (ix) —NR$_e$C(O)—O—;
      (x) —NR$_e$—;
      (xi) —O—;
      (xii) —NR$_e$C(O)NR$_e$—;
      (xiii) —S—;
      (xiv) —S(O)—;
      (xv) —S(O)$_2$—;
      (xvi) —S(O)$_2$NR$_e$—; and
      (xvii) —NR$_e$S(O)$_2$—;

wherein $R_e$ is selected from hydrogen and methyl; and R is a biorthogonal handle.

2. The compound of claim 1 or a salt thereof, wherein $L_a$ is (3-10C)alkylene and $PG_a$ is —NH—CO—CH=CH$_2$.

3. The compound of claim 1 or a salt thereof, wherein $Q_1$ is absent or selected from:

(i) —C(O)NR$_a$—;

(ii) —NR$_2$C(O)—;

(iii)

(iv)

and (v) —C(O)O—;

wherein $R_a$ is selected from hydrogen or methyl.

4. The compound of claim 1 or a salt thereof, wherein a is 2 to 12; and Monomer A is —OCH$_2$CH$_2$—.

5. The compound of claim 1 or a salt thereof, wherein b is 2 to 12; and Monomer B is —CH$_2$CH$_2$O—.

6. The compound of claim 1 or a salt thereof, wherein $Q_2$ is absent or selected from:

(i) —C(O)NR$_a$—;

(ii) —NR$_a$C(O)—;

(iii)

; and (iv)

;

wherein $R_a$ is selected from hydrogen and methyl.

7. The compound of claim 1 or a salt thereof, wherein c is 2 to 8 and Monomer C is —CH$_2$CH$_2$O—.

8. The compound of claim 1 or a salt thereof, wherein $Q_3$ is absent or selected from:

(i) —C(O)NR$_c$—;

(ii) —NR$_c$C(O)—;

(iii)

;

(iv)

;

(v) —C(O)—; and (vi) —C(O)O—;

wherein $R_c$ is hydrogen or methyl.

9. The compound of claim 1 or a salt thereof, wherein $Q_4$ is a group of the formula:

$$\text{-}Q_{4e}\text{-}L_7\text{-}Q_{4b}\text{-}$$

wherein $Q_{4a}$ is selected from:

(i) —C(O)NR$_d$—;

(ii) —NR$_d$C(O)—;

(iii)

;

(iv)

;

(v) —C(O)—;

(vi) —C(O)O—;

(vii) —OC(O)—;

(viii) —O—C(O)NR$_d$—;

(ix) —NR$_d$C(O)—O—;

(x) —NR$_d$—;

(xi) —O—; and (xii) —NR$_d$C(O)NR$_d$—;

wherein $R_d$ is selected from hydrogen or methyl;

$L_7$ is absent or (1-5C)alkylene;

$Q_{4b}$ is absent when $L_7$ is absent or, when $L_7$ is a (1-5C) alkylene, $Q_{4b}$ is absent or selected from:

(i) —C(O)NR$_e$—;

(ii) —NR$_e$C(O)—;

(iii)

;

(iv)

;

(v) —C(O)—;

(vi) —C(O)O—;

(vii) —OC(O);

(viii) —O—C(O)NR$_e$—;

(ix) —NR$_e$C(O)—O—;

(x) —NR$_e$—;

(xi) —O—; and (xii) —NR$_e$C(O)NR$_e$—;

wherein Re is selected from hydrogen and methyl.

10. The compound of claim 1 or a salt thereof, wherein R is a group with a structure selected from:

11. The compound of claim 1 or a salt thereof, wherein Q₄-R forms a group selected from:

64

12. A compound, or a salt thereof, of the formula:

13. A conjugate comprising a protein or peptide probe having at least one di-sulphide bond and a payload; wherein the protein or peptide probe is connected to the payload by a compound of formula (I) according to claim 1, or a salt thereof.

14. A conjugate according to claim 13, wherein the protein or peptide probe is an antibody.

15. A conjugate according to claim 13, wherein the payload is selected from the group consisting of an oligo-nucleotide, a pharmacologically active agent, a fluorophore, a bioluminescent group, a radio-isotope or radio-labelled moiety, a polymer, a dendrimer, a peptide and a lipid.

16. A conjugate according to claim 13, wherein the protein or peptide probe is an antibody and the payload is a detection moiety.

17. A method of detecting a protein of interest in a biological sample, the method comprising:

incubating the biological sample with a conjugate according to claim 13 wherein the payload is a detection moiety and allowing the protein or peptide probe to bind with the protein of interest;

removing unbound conjugate; and assaying for the presence of the detection moieties within the sample;

wherein the presence of detection moieties within the sample indicates that the protein of interest is present in the sample.

18. A method of detecting and locating protein molecules and native nucleic acid molecules of interest in a biological sample, the method comprising:

incubating the biological sample with a conjugate according to claim 13 wherein the payload is a detection moiety and allowing the protein or peptide probe to bind with the protein of interest;

removing unbound conjugate;

contacting the biological sample with a monomeric solution;

polymerising the monomeric solution to produce a polymer matrix that is bound to the biological sample and to the polymerizable group of the conjugate;

digesting proteins within the biological sample;

assaying for the presence of the detection moiety within the polymer matrix; and detecting the presence of a native nucleic acid present in the polymer matrix by a fluorescence in-situ hybridisation technique; wherein the presence of detection moieties in the polymer matrix indicates that the protein of interest was present in the biological sample and the location of the detection moieties in the polymer matrix indicates the location of the protein of interest within the biological sample; and wherein the location of the native nucleic acid molecules in the polymer matrix indicates the location of the native nucleic acid molecules in the biological sample.

19. A method of detecting a protein of interest in a biological sample by expansion microscopy, the method comprising:

incubating the biological sample with a conjugate according to claim 13 wherein the payload is a detection moiety and allowing the protein or peptide probe to bind with the protein of interest;

removing unbound conjugate;

contacting the biological sample with a monomeric solution;

polymerising the monomeric solution to produce a polymer matrix that is bound to the biological sample and to the conjugate via the polymerizable group of the conjugate;

hydrating the polymer matrix such that it expands; and performing microscopy to detect the presence of the visualisable detection moieties within the sample.

20. A conjugate according to claim 15, wherein:

(i) the pharmacologically active agent is a drug or biologic; and/or (ii) the polymer is PEG.

\* \* \* \* \*